(12) United States Patent
Shahoian et al.

(10) Patent No.: US 10,932,988 B2
(45) Date of Patent: Mar. 2, 2021

(54) MALE AND FEMALE SEXUAL AID WITH WIRELESS CAPABILITIES

(71) Applicant: Sparq Laboratories, LLC, Tiburon, CA (US)

(72) Inventors: Erik J. Shahoian, Sonoma, CA (US); John McCoy, Novato, CA (US); Lawrence E. Miller, Scotts Valley, CA (US); David P. Bim-Merle, Chicago, IL (US); Francois W. Brahic, San Francisco, CA (US); Kuan Li, Sunnyvale, CA (US); David J. Gutierrez, Apex, NC (US); Michael K. Wong, Sunnyvale, CA (US); Darrel Q. Pham, San Jose, CA (US)

(73) Assignee: Sparq Laboratories, LLC, Tiburon, CA (US)

( * ) Notice: Subject to any disclaimer, the term of this patent is extended or adjusted under 35 U.S.C. 154(b) by 0 days.

(21) Appl. No.: 16/923,012

(22) Filed: Jul. 7, 2020

(65) Prior Publication Data

US 2020/0330320 A1 Oct. 22, 2020

Related U.S. Application Data

(63) Continuation of application No. 15/575,164, filed as application No. PCT/US2016/033183 on May 19, 2016.
(Continued)

(51) Int. Cl.
*A61H 19/00* (2006.01)
*A61F 5/00* (2006.01)
(Continued)

(52) U.S. Cl.
CPC ............... *A61H 19/44* (2013.01); *A61F 5/00* (2013.01); *A61F 5/451* (2013.01); *A61F 6/00* (2013.01);
(Continued)

(58) Field of Classification Search
CPC ........ A61H 19/40; A61H 19/44; A61H 19/50; A61H 21/00; A61H 23/00; A61H 19/34; A61H 19/32; A61H 19/30
See application file for complete search history.

(56) References Cited

U.S. PATENT DOCUMENTS 2,781,041 A 2/1957 Weinberg
4,102,335 A 7/1978 Woodward et al.
(Continued)

FOREIGN PATENT DOCUMENTS

CN 203154258 U 8/2013
EP 1945123 A1 7/2008
(Continued)

OTHER PUBLICATIONS

3M: Scotch® Electrical Semi-Conducting Tape 13 (Datasheet): 4 pgs.; Sep. 2012; retrieved from the internet Aug. 18, 2014 from: http://multimedia.3m.com/mws/mediawebserver?mwsld.SSSSSuH8gc7nZxlUNx_Um8TSevUqe17zHvTSevTSeSSSSSS-&fn=78-8141-5824-2_R1.pdf.

*Primary Examiner* — Christine H Matthews
(74) *Attorney, Agent, or Firm* — Shay Glenn LLP

(57) ABSTRACT

Described herein are interactive devices that mimic a portion of a human male and a female genitalia. The male device includes a unique bead drive assembly for providing an extending and retracting motion. Also included on the male device is a massager sub-assembly able to inflate and deflate while being able to slide along a shaft of the male device. The female device includes a clamshell constrictor having
(Continued)

an inflation mechanism that is able to provide a squeezing motion as well as being able to slide back and forth within the body of the female device. Also disclosed herein are method of communication and interaction between a pair of interactive devices or multiple interactive devices. Finally, methods of managing interactive sessions between multiple interactive devices are also described.

15 Claims, 38 Drawing Sheets

Related U.S. Application Data

(60) Provisional application No. 62/163,740, filed on May 19, 2015, provisional application No. 62/182,326, filed on Jun. 19, 2015.

(51) Int. Cl.
| | |
|---|---|
| *G06F 16/68* | (2019.01) |
| *A61F 6/00* | (2006.01) |
| *A61F 5/451* | (2006.01) |
| *H04W 12/04* | (2021.01) |
| *A61H 15/00* | (2006.01) |
| *H04W 12/08* | (2021.01) |
| *A61F 6/06* | (2006.01) |
| *H04L 29/06* | (2006.01) |
| *G06F 16/903* | (2019.01) |
| *G06F 16/23* | (2019.01) |
| *A61H 7/00* | (2006.01) |
| *A61H 23/00* | (2006.01) |
| *A61H 9/00* | (2006.01) |
| *G16H 20/30* | (2018.01) |

(52) U.S. Cl.
CPC ............ *A61F 6/06* (2013.01); *A61H 15/0078* (2013.01); *A61H 19/34* (2013.01); *G06F 16/68* (2019.01); *H04W 12/04033* (2019.01); *H04W 12/08* (2013.01); *A61H 7/002* (2013.01); *A61H 7/007* (2013.01); *A61H 9/0057* (2013.01); *A61H 19/32* (2013.01); *A61H 23/008* (2013.01); *A61H 2015/005* (2013.01); *A61H 2015/0042* (2013.01); *A61H 2201/0103* (2013.01); *A61H 2201/1207* (2013.01); *A61H 2201/1463* (2013.01); *A61H 2201/1628* (2013.01); *A61H 2201/5012* (2013.01); *A61H 2201/5023* (2013.01); *A61H 2201/5064* (2013.01); *A61H 2201/5082* (2013.01); *A61H 2201/5097* (2013.01); *A61H 2230/00* (2013.01); *A61H 2230/50* (2013.01); *A61H 2230/60* (2013.01); *G06F 16/2358* (2019.01); *G06F 16/903* (2019.01); *G16H 20/30* (2018.01); *H04L 63/06* (2013.01)

(56) References Cited

U.S. PATENT DOCUMENTS

| | | |
|---|---|---|
| 4,407,275 A | 10/1983 | Schroeder |
| 5,331,974 A | 7/1994 | Sook |
| 5,501,650 A | 3/1996 | Gellert |
| 5,836,865 A | 11/1998 | Ritchie et al. |
| 5,889,672 A | 3/1999 | Schuler et al. |
| 5,956,484 A | 9/1999 | Rosenberg et al. |
| 6,028,531 A | 2/2000 | Wanderlich |
| 6,113,532 A | 9/2000 | Yap |
| 6,179,797 B1 | 1/2001 | Brotz |
| 6,275,213 B1 | 8/2001 | Tremblay et al. |
| 6,336,907 B1 | 1/2002 | Done et al. |
| 6,368,268 B1 | 4/2002 | Sandvick |
| 6,423,017 B2 | 7/2002 | Brotz |
| 6,551,450 B1 | 4/2003 | Thomas et al. |
| 6,569,083 B1 | 5/2003 | Kassman |
| 6,592,516 B2 | 7/2003 | Lee |
| 6,651,668 B1 | 11/2003 | Piarril |
| 6,658,325 B2 | 12/2003 | Zweig |
| 6,741,895 B1 | 5/2004 | Gatni et al. |
| 6,793,619 B1 | 9/2004 | Biumental |
| 6,890,293 B2 | 5/2005 | Kobayashi |
| 7,044,924 B1 | 5/2006 | Roth et al. |
| 7,046,151 B2 | 5/2006 | Dundon |
| 7,096,090 B1 | 8/2006 | Zweig |
| 7,174,238 B1 | 2/2007 | Zweig |
| 7,438,681 B2 | 10/2008 | Kobashikawa et al. |
| 7,577,476 B2 | 8/2009 | Hochman et al. |
| 7,608,037 B2 | 10/2009 | Levy |
| 7,720,572 B2 | 5/2010 | Ziegler et al. |
| 7,762,945 B2 | 7/2010 | Blumenthal |
| 7,812,820 B2 | 10/2010 | Schuler et al. |
| 7,846,114 B2 | 12/2010 | Webster et al. |
| 7,938,789 B2 | 5/2011 | Imboden et al. |
| 8,012,082 B1 | 9/2011 | Lefew |
| 8,016,778 B2 | 9/2011 | Brown et al. |
| 8,255,299 B2 | 8/2012 | Cambridge |
| 8,308,631 B2 | 11/2012 | Kobashikawa et al. |
| 8,313,424 B2 | 11/2012 | Gabrielidis |
| 8,378,794 B2 | 2/2013 | Alarcon |
| 8,382,656 B1 | 2/2013 | Brown |
| 8,409,120 B2 | 4/2013 | Knyrim |
| 8,419,611 B1 | 4/2013 | Hatami |
| 8,449,451 B2 | 5/2013 | Dawe |
| 8,505,086 B2 | 8/2013 | Norman et al. |
| 8,508,469 B1 | 8/2013 | Rosenberg et al. |
| 8,734,323 B2 | 5/2014 | Staffolani |
| 8,751,044 B2 | 6/2014 | Eriksson |
| 8,753,300 B2 | 6/2014 | Deshpande |
| 8,758,282 B2 | 6/2014 | Malhi et al. |
| 8,813,198 B2 | 8/2014 | Louboutin et al. |
| 8,936,544 B2 | 1/2015 | Shanoian et al. |
| 8,994,800 B2 | 3/2015 | Brockway et al. |
| 10,045,906 B2 | 8/2018 | Shahoian et al. |
| 2002/0065477 A1 | 5/2002 | Boyd et al. |
| 2002/0133103 A1 | 9/2002 | Williams et al. |
| 2003/0009119 A1 | 1/2003 | Kamm et al. |
| 2003/0036678 A1 | 2/2003 | Abbassi |
| 2003/0083544 A1 | 5/2003 | Richards et al. |
| 2003/0195441 A1 | 10/2003 | Firouzgar |
| 2004/0097852 A1 | 5/2004 | Boyd et al. |
| 2004/0132439 A1 | 7/2004 | Tyagi et al. |
| 2005/0049453 A1 | 3/2005 | Faulkner |
| 2006/0095158 A1 | 5/2006 | Lee et al. |
| 2006/0247682 A1 | 11/2006 | Gerber et al. |
| 2007/0055188 A1 | 3/2007 | Avni et al. |
| 2007/0123748 A1 | 5/2007 | Meglan |
| 2007/0126593 A1 | 6/2007 | Nan |
| 2007/0150104 A1 | 6/2007 | Jong et al. |
| 2007/0179336 A1* | 8/2007 | Knyrim ............... A61H 21/00 600/38 |
| 2008/0139080 A1 | 6/2008 | Zheng |
| 2008/0299869 A1 | 12/2008 | Hsu |
| 2009/0069730 A1* | 3/2009 | Knyrim ............. A61H 23/0254 601/134 |
| 2010/0041944 A1 | 2/2010 | Levy |
| 2010/0174137 A1 | 7/2010 | Shim |
| 2010/0174217 A1 | 7/2010 | Budnik et al. |
| 2010/0191048 A1 | 7/2010 | Kulikov |
| 2010/0268021 A1 | 10/2010 | Standfast et al. |
| 2011/0087337 A1 | 4/2011 | Forsell |
| 2011/0218395 A1 | 9/2011 | Stout |
| 2011/0245743 A1 | 10/2011 | Eddy |
| 2012/0022323 A1 | 1/2012 | Forsell |
| 2012/0071800 A1* | 3/2012 | Knyrim ................. A61H 19/44 601/113 |
| 2012/0215141 A1 | 8/2012 | Peddicord |
| 2012/0215189 A1 | 8/2012 | Wu |
| 2012/0232335 A1 | 9/2012 | Eisenberg et al. |
| 2012/0256864 A1 | 10/2012 | Miki |
| 2012/0259171 A1 | 10/2012 | Shmakov |

(56) References Cited

U.S. PATENT DOCUMENTS

| | | |
|---|---|---|
| 2012/0293435 A1 | 11/2012 | Miki |
| 2012/0316481 A1 | 12/2012 | Purdy et al. |
| 2013/0090524 A1 | 4/2013 | McNamara |
| 2013/0222280 A1 | 8/2013 | Sheynblat et al. |
| 2013/0226050 A1 | 8/2013 | Lee |
| 2013/0331745 A1 | 12/2013 | Sedic |
| 2014/0039252 A1 | 2/2014 | Martens et al. |
| 2014/0066699 A1 | 3/2014 | Golan |
| 2014/0107542 A1 | 4/2014 | Schubert et al. |
| 2014/0171734 A1 | 6/2014 | Kassman |
| 2014/0207032 A1 | 7/2014 | Dematio et al. |
| 2014/0207280 A1 | 7/2014 | Duffley et al. |
| 2014/0235938 A1 | 8/2014 | Schnurr |
| 2014/0243591 A1 | 8/2014 | Weller |
| 2014/0366105 A1 | 12/2014 | Bradley et al. |
| 2015/0133833 A1 | 5/2015 | Bradley et al. |
| 2018/0140502 A1 | 5/2018 | Shahoian et al. |

FOREIGN PATENT DOCUMENTS

| | | |
|---|---|---|
| EP | 2777679 A1 | 9/2014 |
| EP | 2777680 A1 | 9/2014 |
| EP | 2842360 A1 | 3/2015 |
| EP | 2863859 A1 | 4/2015 |
| FR | 2942713 A1 | 9/2010 |
| JP | 2006-149566 | 8/2006 |
| WO | WO98/14147 A1 | 4/1998 |
| WO | WO99/37267 A1 | 7/1999 |
| WO | WO00/15172 A1 | 3/2000 |
| WO | WO2007/033333 A1 | 3/2001 |
| WO | WO2007/047169 A2 | 4/2007 |
| WO | WO2009/048376 A1 | 4/2009 |
| WO | WO2010/032162 A1 | 3/2010 |
| WO | WO2012/101289 A1 | 8/2012 |
| WO | WO2013/175473 A1 | 11/2013 |
| WO | WO2014/131110 A1 | 9/2014 |
| WO | WO2014/138504 A2 | 9/2014 |
| WO | WO2015/060717 A1 | 4/2015 |

\* cited by examiner

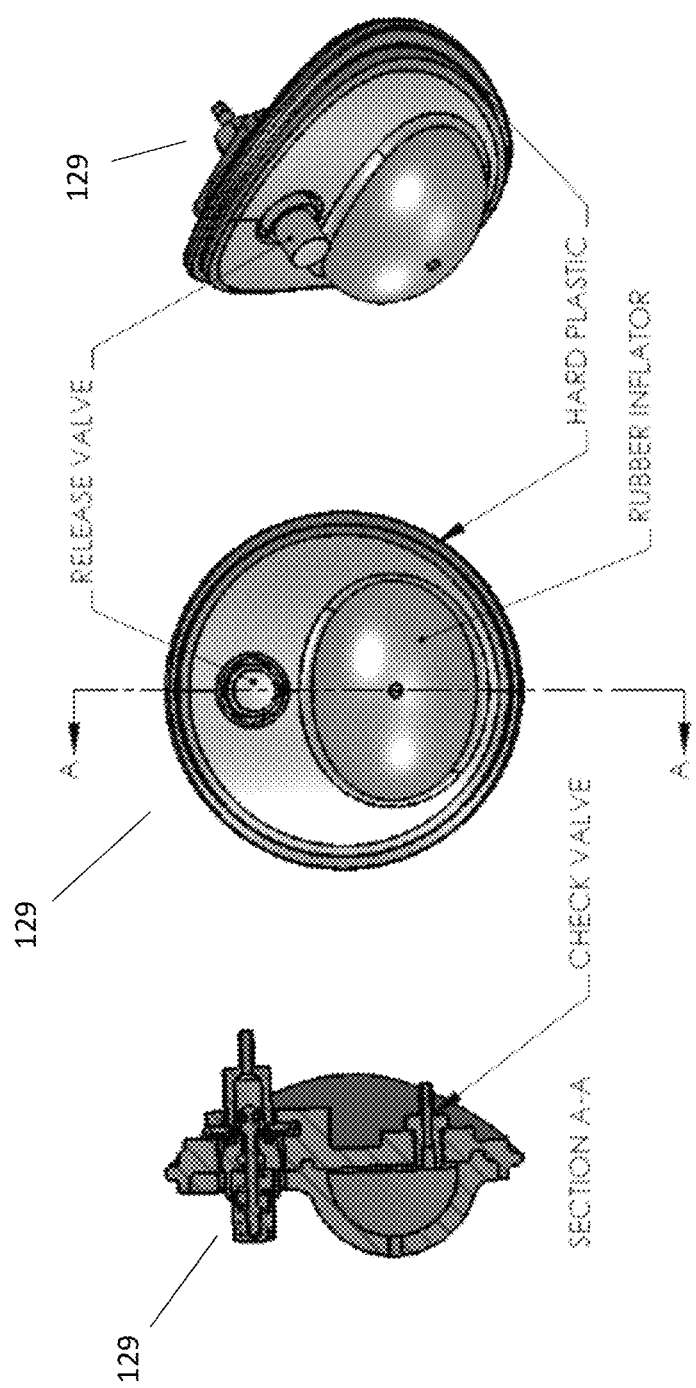

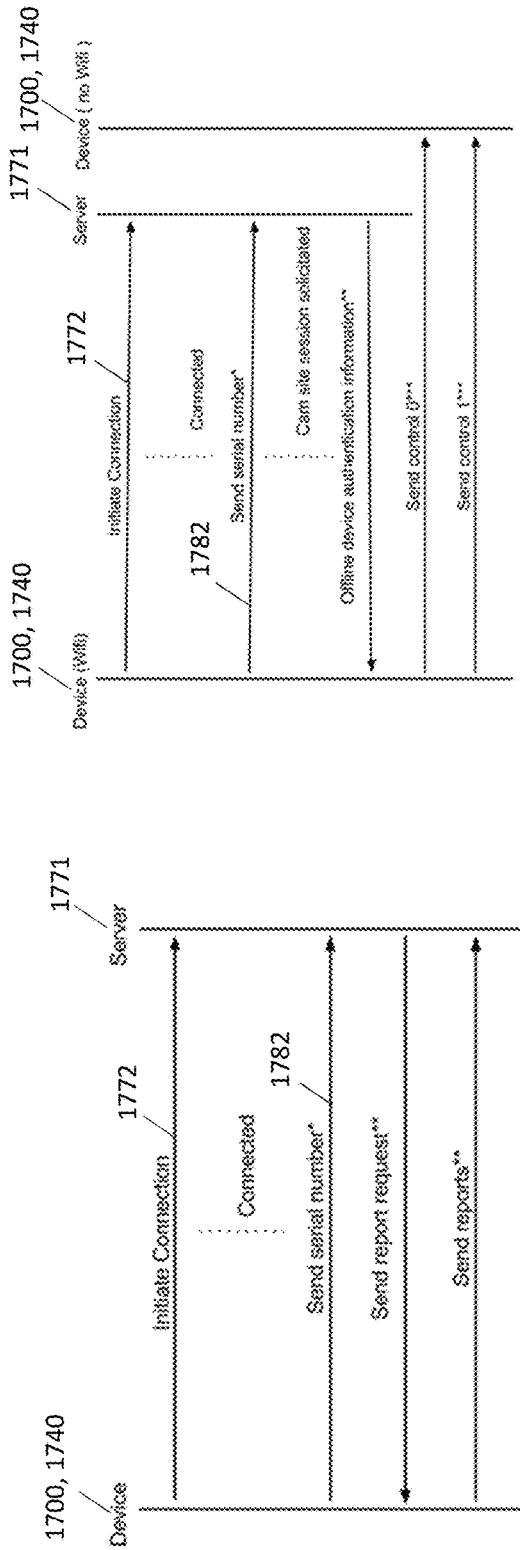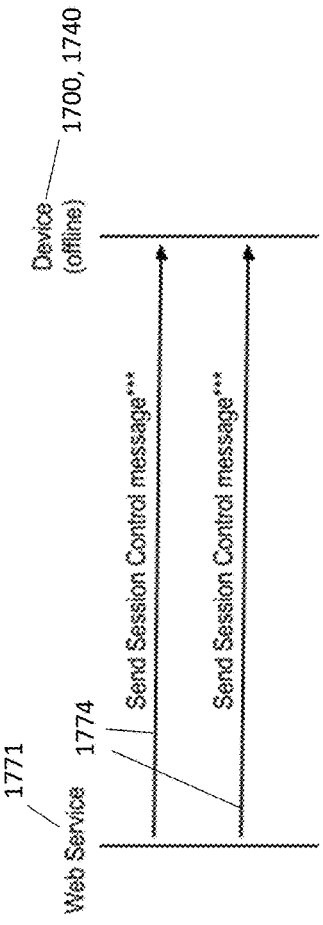
FIG. 17A
FIG. 17B
FIG. 17C

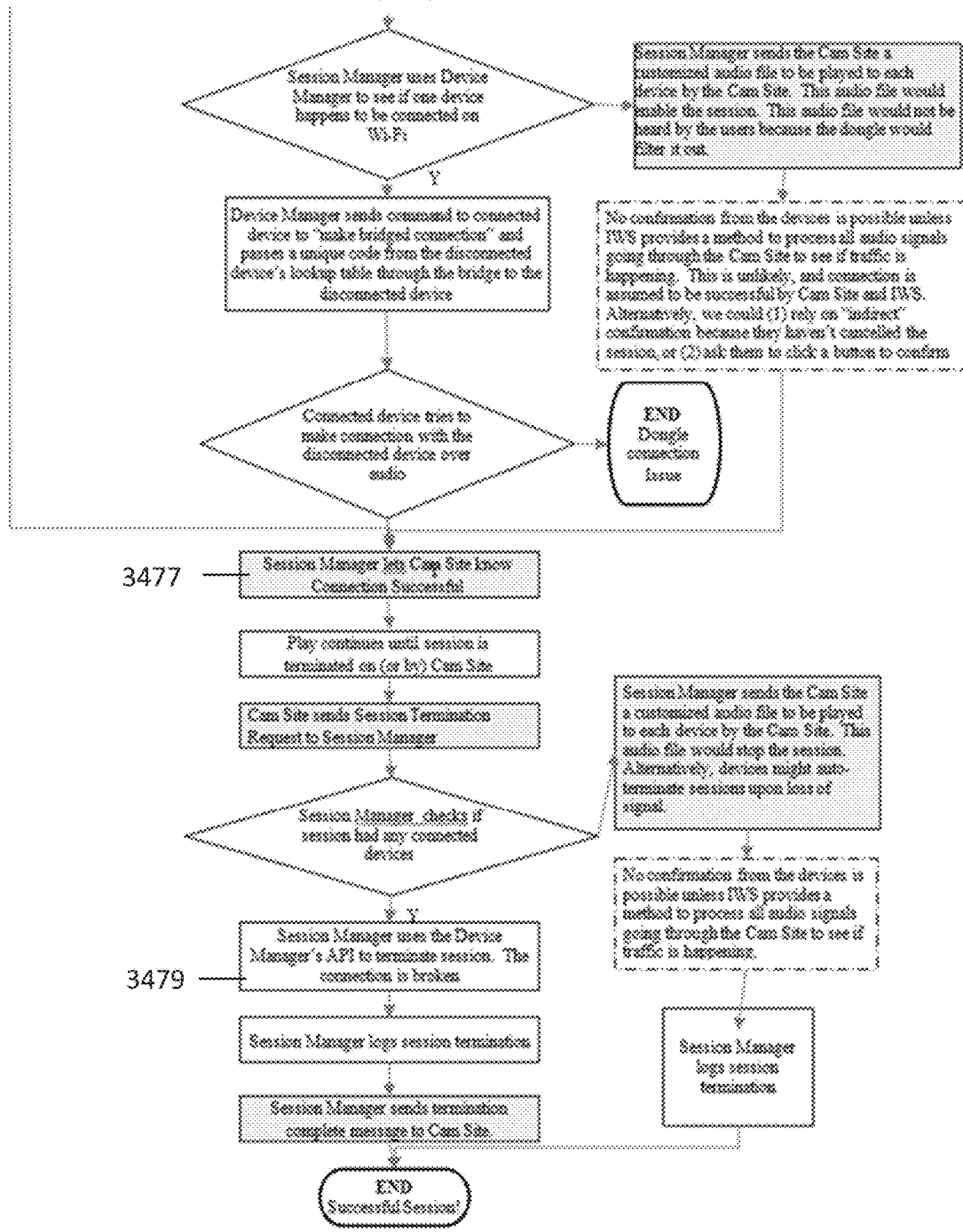

MALE AND FEMALE SEXUAL AID WITH WIRELESS CAPABILITIES

CROSS REFERENCE TO RELATED APPLICATIONS

This patent application is a continuation of U.S. patent application Ser. No. 15/575,164, filed Nov. 17, 2017, titled "MALE AND FEMALE SEXUAL AID WITH WIRELESS CAPABILITIES," now U.S. Patent Application Publication No. 2018/0140502, which is a national phase application under 35 U.S.C. 371 of International Patent Application No. PCT/US2016/033183, filed May 19, 2016, titled "MALE AND FEMALE SEXUAL AID WITH WIRELESS CAPABILITIES," now International Publication No. WO 2016/187375, which claims priority to U.S. Provisional Patent Application Nos. 62/163,740, filed May 19, 2015, titled "MALE AND FEMALE SEXUAL AID WITH WIRELESS CAPABILITIES," and 62/182,326, filed Jun. 19, 2015, and titled "MALE AND FEMALE SEXUAL AID WITH WIRELESS CAPABILITIES," the disclosures of which are herein incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are male and female masturbatory devices. This invention also relates to male and female sexual aids that can be used individually or interactively with one or more participants operated over a network.

BACKGROUND

Sexual aids include masturbatory devices are used by either genders to increase pleasure and intimacy. One type of sexual aid is a male masturbatory device. Many such devices are available on the market today. The majority of male masturbatory devices on the market include a mechanism for providing reciprocating motion such as what is described in WO1996007375. These devices have also been known to include a pressure component largely through components placed along the surrounding walls of the device that can push toward the cavity intended to hold a male penis as is the case with the device described in U.S. Pat. No. 8,647,255. Other devices on the market, such as U.S. Applications 20050049453 and 20110245743 provide an inflatable component intended to provide pressure and a sense of movement along the length of the cavity. A drawback with such stimulation mechanisms is that they do not adequately mimic the smooth stroke motion of real intercourse or manual manipulation. Thus, there is a need in the current male masturbatory market for a device that provides a realistic constriction around a range of phallus diameters, as well as provide a realistic stroke sensation to the phallus contained-within the device.

Sexual aids also include artificial erect penises which may be referred to as dildos. Like other kinds of sexual aids, a variety of dildos are on the market including ones that are mechanized. Issues with mechanical dildos is the unnatural reciprocating movement of the device that provides a far-from-natural feel or where the dildo has an un-natural stiffness that may lead to uncomfortable fit. Thus there is a need in the dildo market, for a realistic-feeling dildo that provides for natural reciprocating motion.

Furthermore, Sexual stimulation aids have been primarily used by individuals either on themselves and others while in the presence of each other in the latter case. In more recent years, advancements in telecommunication, and wider availability of wireless technology has led to more products on the market that allow individuals to control a sexual aid remotely. In these latter scenarios, the user, the person controlling the device that is then able to remotely actuate outputs on a sexual device being used by a recipient. This haptic technology, where touch sensation is translated by applying forces, such as vibration to a portion of a user's body. This area of utilizing remote robotics-type action outputs and sensor inputs in the area of sexual aids has been called teledildonics. While the area of remotely-controlled robotics has seen much advancement in the medical, military, and gaming areas just to name a few, teledildonics has lagged behind these other fields. It is an object of the disclosure to improve haptic communication and output in sexual aids.

SUMMARY OF THE DISCLOSURE

The present invention relates devices that simulate portions of the male and female genitalia where the devices are able to interact wirelessly.

In general, a male device is able to mimic a portion of the male genitalia region. One embodiment of the male device includes a main body region, a tubular body region disposed on the main body, and a bead drive mechanism contained within the tubular body and the main body and able to travel between the two regions.

The tubular body of the male device is a semi-rigid shaft that is in the shape of human male penis. The tubular body including a shaft, a massager sub-assembly, and a sheath. The term "tubular body" as used herein refers to a tube having the approximate shape and size of human male genitalia such as the penis. Tubular body may also include the shaft, glans, meatus, testicles, root (e.g. radix), and so forth. The tubular body includes a proximal end and a distal end, where the proximal end corresponds to the base of penis and the distal end of the tubular body corresponds to the tip of the penis.

The shaft is attached to the main body at a proximal end and is able to flex and bend (in a manner comparable to a real penis). The term "shaft" as used herein refers to the long portion or length of the tubular body. In some cases, the term shaft may refer to the entire length of the tubular body. Shaft may also be used to refer to a portion of the tubular body distinguishable from the tip of the tubular body and its base. A pliable sheath covers the shaft. The sheath is inflatable to mimic a range of different penis sizes.

Also disposed on the shaft is a massager sub-assembly. The massager sub-assembly is coupled to the shaft, the massager sub-assembly is movable proximally and distally along the shaft. The massager sub-assembly is also able to expand and contract which may be under the user or other party's control. The term "massager subassembly" used herein refers to any additional arrangement disposed on the shaft of the male device that is able to provide a simulating output. The massager sub-assembly may have the same material as that of the shaft or be of different material to provide a variation in feel. The massager sub-assembly can provide a general massaging effect such as vibration, pulsations or heat to the area that it contacts. The massager sub-assembly may also provide pressure against the surfaces that it comes into contact with. The massager sub-assembly may also be able to rotate with respect to the shaft. In some examples, the massager sub-assembly is made of a rigid core that is in contact with the shaft. The outer surface of the massager subassembly is composed of inflatable portions or balloons. The inflatable portions can be manually inflated to the desired girth. The massager sub-assembly is disposed on the length of the shaft. The sheath may also include internal corrugations configured to allow smooth compression and expansion when the massager sub-assembly inflates and deflates. The sheath may have a diameter range 3 cm to about 5 cm. In some examples, the massager subassembly is able to extend and retract along the shaft of the device. "Extend and retract" herein generally means moving along the shaft of the male device where expending means moving to a more distal position with respect to the base of the shaft and retracting means moving to a position closer to the proximal end of the tubular body.

The male device includes a bead drive mechanism. The bead drive mechanism functions to replicate the thrust and stiffness components of an erect penis. The bead drive mechanism includes a bead chain that is able to extend and retract within the tubular body through a drive gear. The term "bead drive mechanism" broadly can refer to a drive mechanism that utilizes beads or a series of bead to actuate a particular motion or action. More particularly, the "bead drive mechanism" here refers to an array of beads that are arranged in a line or single axis that is able to move along the single axis. The bead drive mechanism may include a series of beads strung on a flexible filament such as a wire. It is also possible that the string of bead are connected to each other through magnetic forces; in that case, no string or wire may be needed. A compressed spring preloads the series of beads and keeps the bead assembly in compression and still allows the chain to bend locally about the cable's fulcrum.

A drive gear is coupled to the bead assembly and is able to actuate the bead assembly about the longitudinal axis of the shaft. The term "drive gear" used here in can refer to any mechanism that is able to drive the bead assembly. Drive gear can be any mechanism that includes a toothed or ridged gear that couples to another gear or element for engaging and transmitting rotary motion. Drive gear may include straight-cut gear, helical or worm gear, herringbone gear, bevel gear, spiral teeth gear, or one with internal gears. The gear drive may also refer to a mechanism that does not use a wheel and is able to produce a reciprocating motion by other means.

The massager sub-assembly may be coupled to the bead drive mechanism. Also coupled to the bead drive mechanism is a position sensor. The position sensor reports back on the relative position or configuration of the bead assembly. The relative position of the bead assembly will be important in an interactive scenario. The term "bead chain sensor" used herein refers to a sensor that is generally able to detect the location of the bead chain at a particular point and extrapolate the position of the bead chain with respect to the rest of tubular body. The bead chain sensor may be physically coupled to the bead assembly and/or the drive gear. For example, where the bead chain sensor is able to "count" the beads that have moved past it in a particular direction. It may also be possible to have a bead chain sensor that does not come into contact with the actual bead chain or bead drive, for example, an optical sensor.

The main body is attached to the proximal end of the tubular body at an angle between 30 degrees and 130 degrees. The main body also includes a covering anchoring the sheath having a capture lip. The main body region includes a clitoral stimulator. As the name suggests, the clitoral stimulator is intended to contact a region on a female user's body that corresponds to her clitoris when she uses the male device. The clitoral stimulator may be any mechanism that provides a stimulating output to the region directly adjacent to it. For example, vibrations, pulsations, kneading motion, and other outputs may be provided. The clitoral stimulator may be manually controlled by the user during use of the male device in a non-interactive mode. In other examples, the clitoral stimulator may also be operated as part of an interactive session where an outside party may control the vibrator as part of controlling the outputs of the overall male device.

The majority of the systems control for the male device is contained within the main body. The systems control includes a printed circuit board assembly. The printed circuit board assembly coordinates the control of the male device functions. The printed circuit board assembly may include a microcontroller, a power amplifier, battery management components, components for the wireless communication, and analog control components.

Also disposed on the male device main body are user controls. User controls include buttons, key pads, switches, and toggles for affecting the output of the male device. An on/off switch is disposed on the body of the male device. Other user controls may include control for adjusting the position of the massager sub-assembly. Also, a user may control the amount of inflation to the balloon component of the massager sub-assembly. Finally, there may be user controls on the device for selecting different operating modes for the male device.

Also described below are methods of actuating a device for mimicking a portion of the male genitalia. The methods include inflating a massager sub-assembly that is coupled to a shaft of the device. The massager sub-assembly and shaft may be covered by a sheath that forms an elongated tubular body. The massager sub-assembly may be driven distally or proximally within the elongated tubular body by actuating a bead drive to turn a drive gear that is engaged with one or more beads of a bead chain. There may be controls on the device to drive the massager sub-assembly. The bead chain may contain a plurality of adjacent beads and is coupled to the massager sub-assembly. The male device is able to detect a configuration of the bead chain within the tubular body and determine a position of the massager sub-assembly with the tubular body based on the configuration of the bead chain. A user may further employ the male device by grasping a main body of the device when driving the massager sub-assembly. Here, the main body is attached to a proximal end of the tubular body at an angle of between 30 degrees and 130 degrees. Finally, methods described also include wirelessly transmitting instructions to the device to control driving the massager sub-assembly.

The counterpart of the male device is an interactive female device, where the female device is designed to mimic a portion of the female genitalia for providing sexual stimulation. The female device includes a tubular body having a proximal end, a distal end, and an interior space. The female device also includes a flexible sleeve within a proximal end of the interior space of the tubular bod and having a proximal-facing opening where the sleeve forms an open cavity within the proximal end of the tubular body. The female device also includes a clamshell constrictor between the sleeve and the tubular body where the clamshell constrictor includes a first elongated concave surface to expand or constrict the inner diameter of the cavity. The female device includes a constriction actuator gear that is able to pivot the first elongated concave surface relative to the second elongated concave surface to expand or constrict the inner diameter of the cavity. Finally, the female device includes a stroke driver that is coupled to the clamshell constrictor and able to reciprocate the clamshell constrictor proximally and distally within the tubular body.

The tubular body with an opening and cavity disposed on one end. The cavity is expandable to accommodate a range of penis sizes. The cavity is lined with a removable flexible sleeve. The term "flexible sleeve" used herein refers to a covering that lines the cavity. In the broadest sense, the "flexible sleeve" can be constructed from any pliable material conceived of and readily available. In narrower terms, the "flexible sleeve" comprises a durable, flexible material that replicates the feel of human skin. It may also be desirable for the "flexible sleeve" to be made from materials that are largely impermeable. The sleeve is stretchable and pliable. In some examples, the sleeve may have corrugations that afford stretching.

The female device also includes a constrictor assembly that has two degrees of freedom: movement along the longitudinal axis of the shaft and a constrictor action on the cavity. In this example, the constrictor assembly is supported by guide shafts that run along the length of the female device. The guide shaft may be between the tubular body and the sleeve, wherein the clamshell constrictor reciprocates along the guide shaft. A stroke actuation assembly is able to push and pull the constrictor assembly along the length of the cavity.

In this example, the constricting action is realized with a clamshell constrictor, where the clamshell constrictor is able to alter the inner diameter distance to effectuate a constriction against the object contained within. The term "clamshell constrictor" as used herein refers to any two elongated concave surfaces that face each other and are able to alter the inner distance between the two elongate concave surfaces. The clamshell constrictor may be between the sleeve and the tubular body, the clamshell constrictor having a first elongated concave surface extending proximally to distally along an inner wall of the tubular body opposite from the first elongated concave surface. In other examples, the clamshell constrictor are two pieces of aligned elongated concave surfaces that face each other having a hinged side and an unattached side that is able to periodically reduce the inner diameter between the two elongated concave surfaces that corresponds to a squeezing or constricting action. The first concave surface may be hinged to a sled that is coupled to the stroke driver and configured to be driven proximally and distally within the tubular body.

The clamshell constriction motion is controlled via a constriction actuator. The constriction actuator gear may be configured to pivot the first elongated concave surface relative to the inner wall to expand or constrict the inner diameter of the cavity. The constriction actuator may be any assembly that is able to provide a constricting or squeezing motion to the clamshell constrictor. The clamshell constrictor also includes a first and a second inflatable balloon disposed on the first and the second elongated concave surface respectively. The constriction actuator may be a single stage gear having a pinion and sector gear, where the sector gears are arranged for driving the pinion The portion of shell that will be in contact with the cavity includes balloons that can be inflated to a firmness that will provide the desired amount of constriction about the cavity. The inflatable balloon coupled to the clamshell constrictor and configured to constrict the inner diameter of the cavity when the inflatable balloon is inflated. A user will be able to adjust the amount of constriction using user controls located on the female device. The female device may include an inflation control on the tubular body, the inflation control coupled to an inflatable balloon between the tubular body and the sleeve and configured to adjust the inner diameter.

The female device also includes a stroke actuator. The stroke actuator is able to move the clamshell constrictor within the cavity along the longitudinal axis of the device, repetitively extending proximally and distally within the cavity. In other words, the female device may include a reciprocation control on the tubular body, the reciprocation control communicating with the stroke driver to drive reciprocation of the clamshell constrictor proximally and distally within the tubular body. The stroke actuator may include a belt drive and a rack and pinion driving that provides translational motion when the belt drive is rotated.

In some examples, some of the user controls for both the male and female device may be controlled with an external audio dongle. The external audio dongle will be able to interface with the female or male device using for example, a plug. In those cases where an audio dongle is used, some or all of the manual user controls for the male and female devices may be moved to the audio dongle. Further, the female device may include control circuitry within the tubular body, the control circuitry including a wireless communication circuit, wherein the control circuitry is configured to wirelessly receive a reciprocation control instruction for controlling the stroke driver.

Both the male and female devices can be used in either with or without a network connection. In the former case, a user can turn on the device and use the male or female device by playing pre-loaded programs on either device. The use may also the manual user controls to adjust the corresponding actuators to arrive at setting that are most pleasurable to them. In some examples, both devices will be able to save certain settings of the user's choosing. In an interactive mode, both the male and female devices need to be authenticated and registered. Both the male and female devices will search for available wireless connections. If a wireless connection is available, the user can authenticate and register their device with a Service Provider and then be able to interact with other registered and authenticated devices. Typically, when the interactive devices are first turned on, they may act as its own access point and connect to an available wireless-enabled device for the purpose of authenticating and registering the device. The wireless-enabled device will then be prompted to load a webpage where the user may enter an authenticating code. In the case where an audio dongle is used, the user may enter the device information though keys, buttons, switches on the device or use the external audio dongle for inputting the authenticating information. Also provided is a dedicated webpage where a second digital address and access code may be entered. The second digital address is typically the address of a locally-available wireless network. The wireless-enabled device is then able to display a dedicated webpage of the service provider. The interactive device is able to receive the second digital address and access code from the wireless-enabled device, turn off its capabilities as an access point, and connect to the locally-available wireless network. In other examples, the male or female device may be registered or authenticated using an audio signal.

In an interactive mode, a first user may control the interactive device of a second user. In some modes, the ability to control each other's interactive devices is reciprocal. In an interactive session mode, a second interactive device or a plurality of interactive devices are able to periodically communicate session codes between the first interactive device and the second interactive device or a plurality of interactive devices. In other interactive sessions, session codes are communicated between the interactive devices and the remote server (service provider). The remote server (service provider) is able to send control instructions to the interactive devices and the interactive device is able to transmit to the remote server operational information. The interactive devices are able to send authenticating communication between one or more other interactive devices using specific keys or codes. The specific keys or codes are associated with each interactive device's serial number. The serial numbers for all interactive devices may be stored with the remote server. In some instances, the remote server may monitor the connectivity quality of the interactive devices. Further, in the interactive mode, each interactive device is able to send periodic signals indicating that the interactive device is still active within the session. When the remote server detects that a particular interactive device is inactive within a session, it may terminate the session if the session only contained two interactive devices. Finally, interactive devices may interact with each other through a third-party websites.

In some modes, only one user is able to control the interactive device of the other and not vice versa. In the interactive mode, the male and female devices can function in a monogamous mode or in a multi-user mode. In the monogamous mode, a first interactive device may only interact with a second interactive device that it has been paired with. In a multi-user mode, the interactive devices may be able to connect with and interact with any available interactive device that has accepted a session request.

Also disclosed herein are methods for wirelessly communicating and controlling the activity of a sex toy, which includes: initiating a wireless access point capability for the sex toy, where the wireless access point capability of the sex toy has a first digital address and wirelessly accessing, using a wireless-enabled device, the sex toy via the first digital address, providing, from the sex-toy, a dedicated webpage including an input for receiving a second digital address and an access code, wherein the second digital address comprises the address of a locally-available wireless network, displaying the dedicated webpage, receiving at the sex toy, the second digital address and access code from the wireless-enabled device, and connecting the sex toy to the locally-available wireless network using the received second digital address and access code.

The method also includes being able to disconnect the wireless-enabled device from the sex-toy before connecting the sex toy to the locally available wireless network. A user would also be able to turn off the wireless access point capability before connecting the sex toy to the locally-available wireless network. The interactive devices will also be able to connect to a remote server through the locally-available network and registering the sex toy on the remote server.

In interactive mode, methods also include connecting to a second sex toy by providing the first digital address to the second sex toy. The first interactive device may then establishing a session with a second sex toy or a plurality of other sex toys, where session codes are communicated periodically between the sex toy and the second sex toy or the plurality of other sex toys. The interactive devices may send, from a remote server, session codes to one or more sex toys within the session. The interactive device may also wirelessly receive control instructions for operating the interactive device from a remote server. The interactive device may wirelessly receive, from a second interactive device that is wirelessly connected to the first interactive device, control instructions for operating the first interactive device. The interactive device may wirelessly transmit from the interactive device, to a remote server, operational information for the interactive device.

Methods also include authenticating the interactive device using a common key, wherein the common key is an identifier known by a remote server to which the interactive device is wirelessly connected. Methods may include authenticating communication between the interactive device and one or more other interactive devices, using a specific key, wherein the specific key is linked to a serial number for the interactive device and wherein the serial number is stored with a remote server. Methods can also include wirelessly connecting the sex toy through the local-available wireless network to a remote server that is configured to prevent, allow or prevent and allow recording or playing back of a session using the sex toy.

Methods for the interactive device interacting with other devices also include being configured to terminate the session if the sex toy or a second sex toy communicating with the sex toy fails to provide a signal indicating that it is still active within the session. The interactive devices are also configured to communicate with a second sex toy only after confirming that the second sex toy is monogamously paired with the sex toy.

In some cases, a company website may provide remote monitoring of connectivity quality between the sex toy and a second sex toy. A company website may also facilitate, using a remote server running a third-party website, communication between the sex toy and a second sex toy or device.

Methods also include wirelessly communicating and controlling the activity of an interactive device. The interactive device is able to initiate a wireless access point capability for the interactive device, where the wireless access point capability of the interactive device has a first digital address. A user may wirelessly access, the interactive device via the first digital address using a wireless-enabled device. A company website may provide, from the interactive device, a dedicated webpage including an input for receiving a second digital address and an access code, wherein the second digital address comprises the address of a locally-available wireless network. The user may then view the displayed dedicated webpage. The interactive device may then receive the second digital address and access code from the wireless-enabled device. Once authenticated, the interactive device may turn off the wireless access point capability. The interactive device may then connect to the locally-available wireless network using the received second digital address and access code; and wirelessly receive, at the sex toy, command instructions for operating the sex toy from a remote device.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 4B and 4D show cross-sections of two sleeve designs. FIGS. 4C and 4E show side views of a first and a second sleeve embodiment.

FIG. 5 show a cross-sectional, front, and offset side view of an inflator on the female device.

FIG. 17A is a diagram showing an example of the interactive device interacting with a server.

FIG. 17B is a diagram showing a connected interactive device authenticating an offline device and communicating over audio.

FIG. 17C is a diagram of a web server to interactive device communication over audio encrypted with a device specific key.

FIG. 26 is a block diagram showing a device communication processor and components that it interacts with.

DETAILED DESCRIPTION

Figure 1:
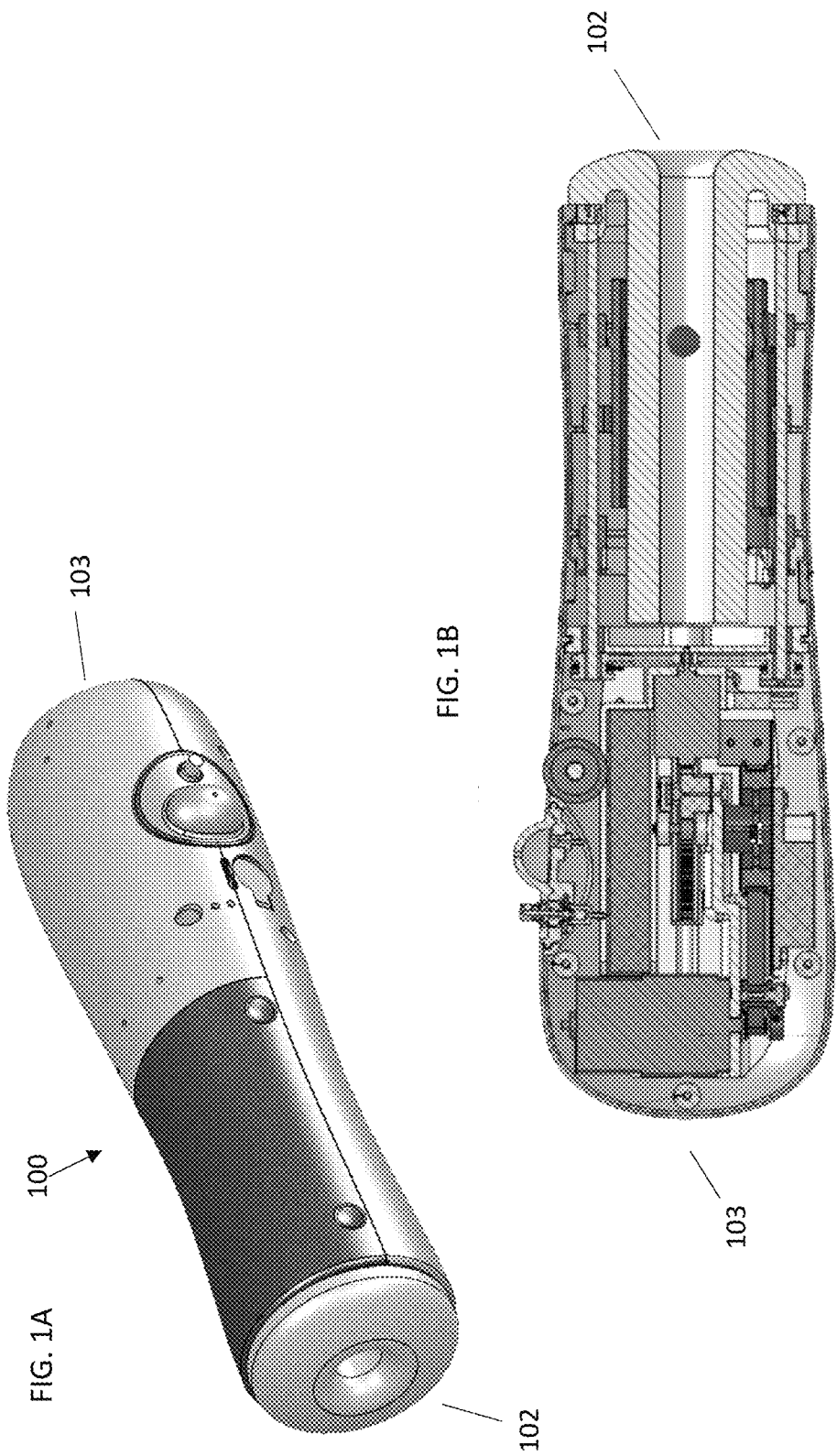
FIG. 1A is a pictorial of the female device.
FIG. 1B is a cross-section along the longitudinal axis of the female device.
Figure 2:
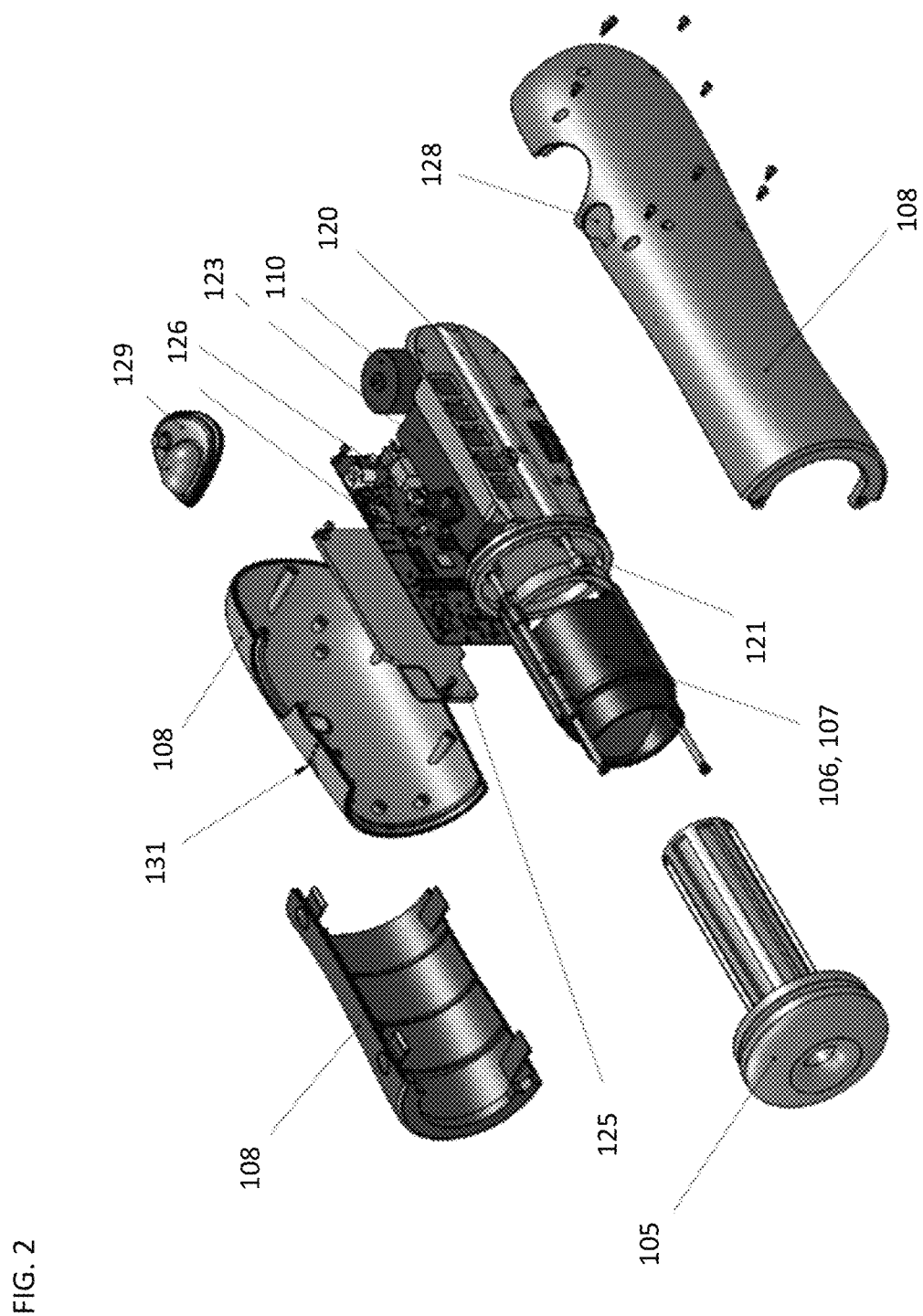
FIG. 2 is an exploded view of the female device.
Figure 3:
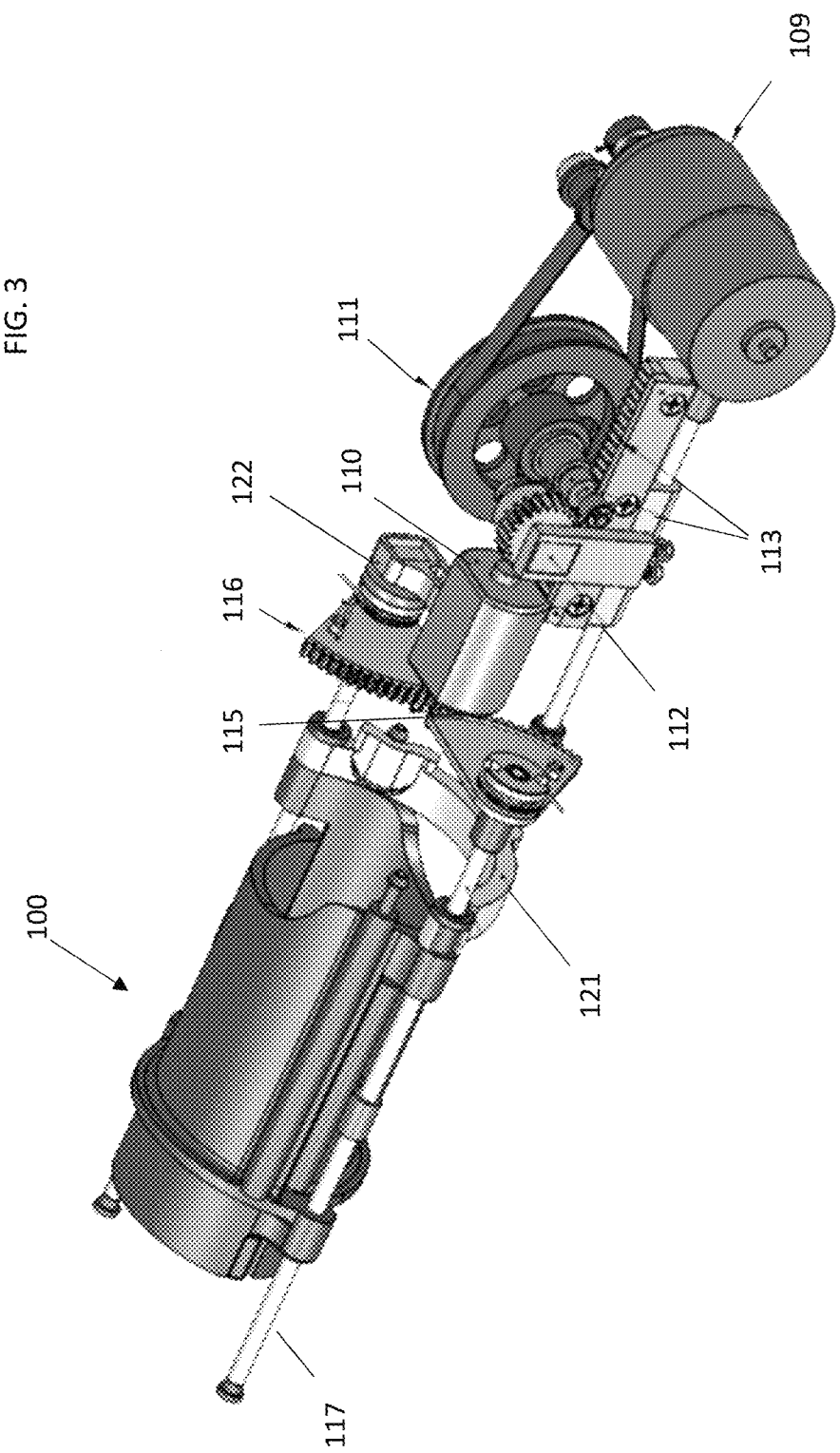
FIG. 3 is a view of the female device without outer coverings.
Figure 4C:
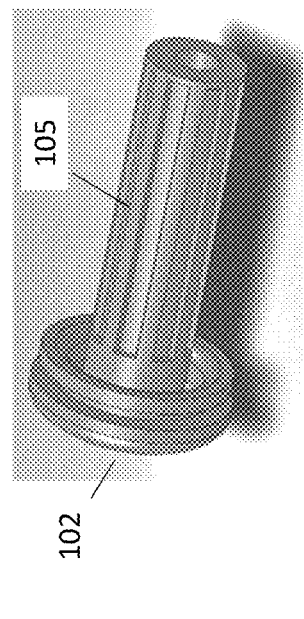
FIG. 4A-4E show various embodiments of a sleeve.
Figure 4E:
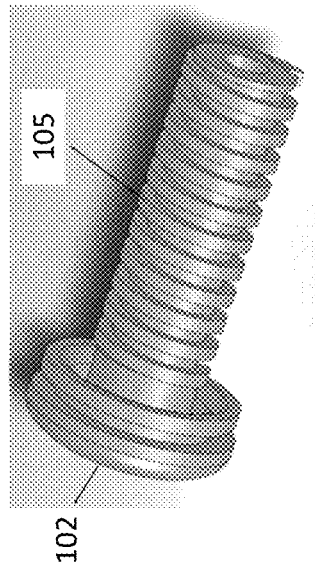
Figure 4B:
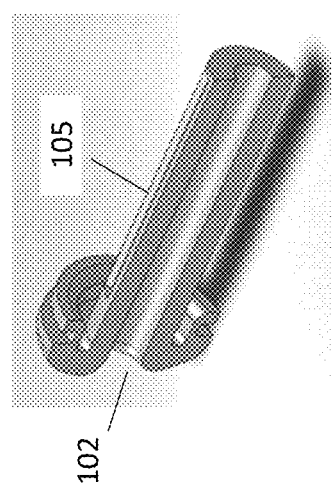
Figure 4D:
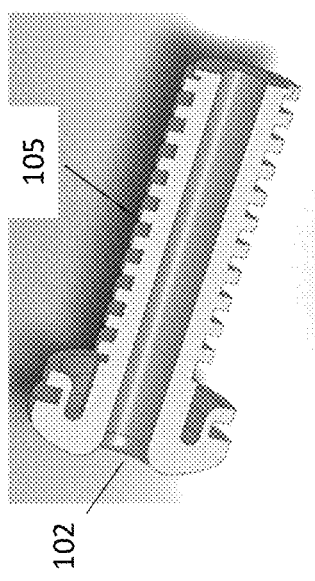
Figure 4A:
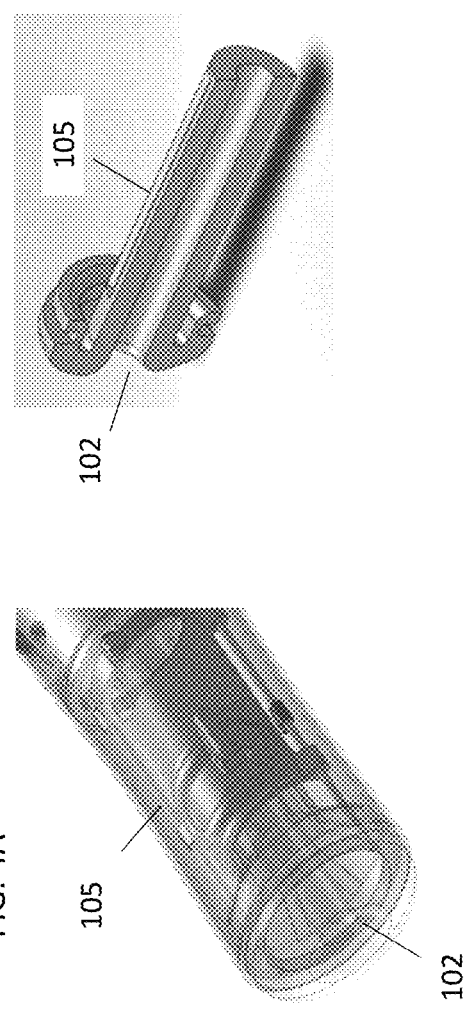
Figure 6:
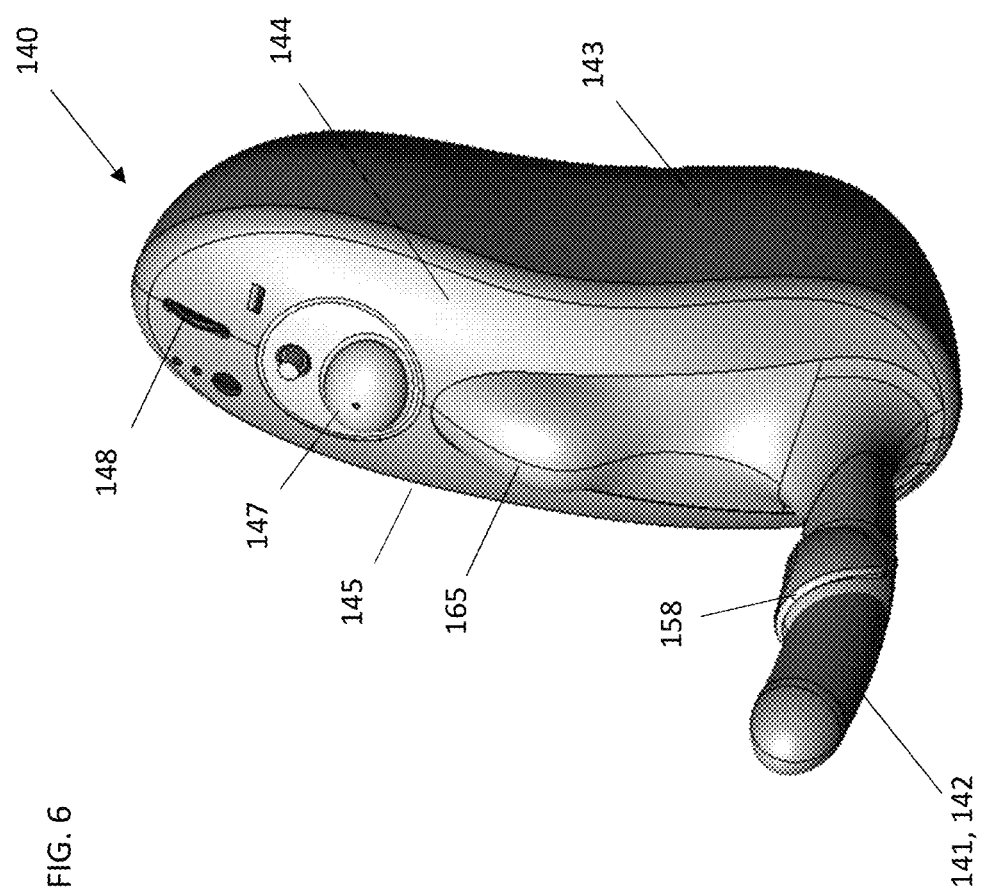
FIG. 6 is a pictorial of an embodiment of a male device.
Figure 7:
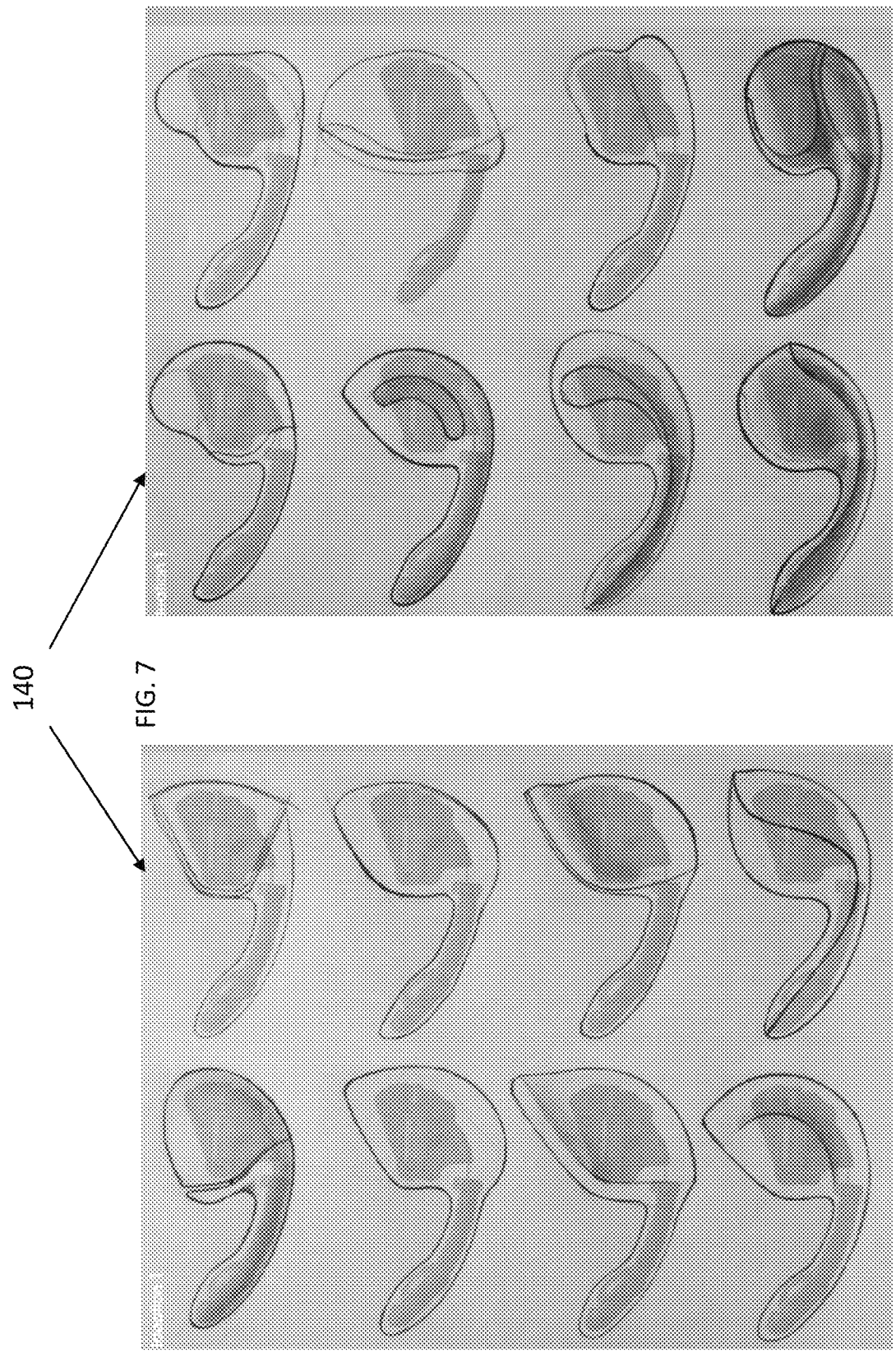
FIG. 7 shows sketches of a number of outer designs for the male device.
Figure 8:
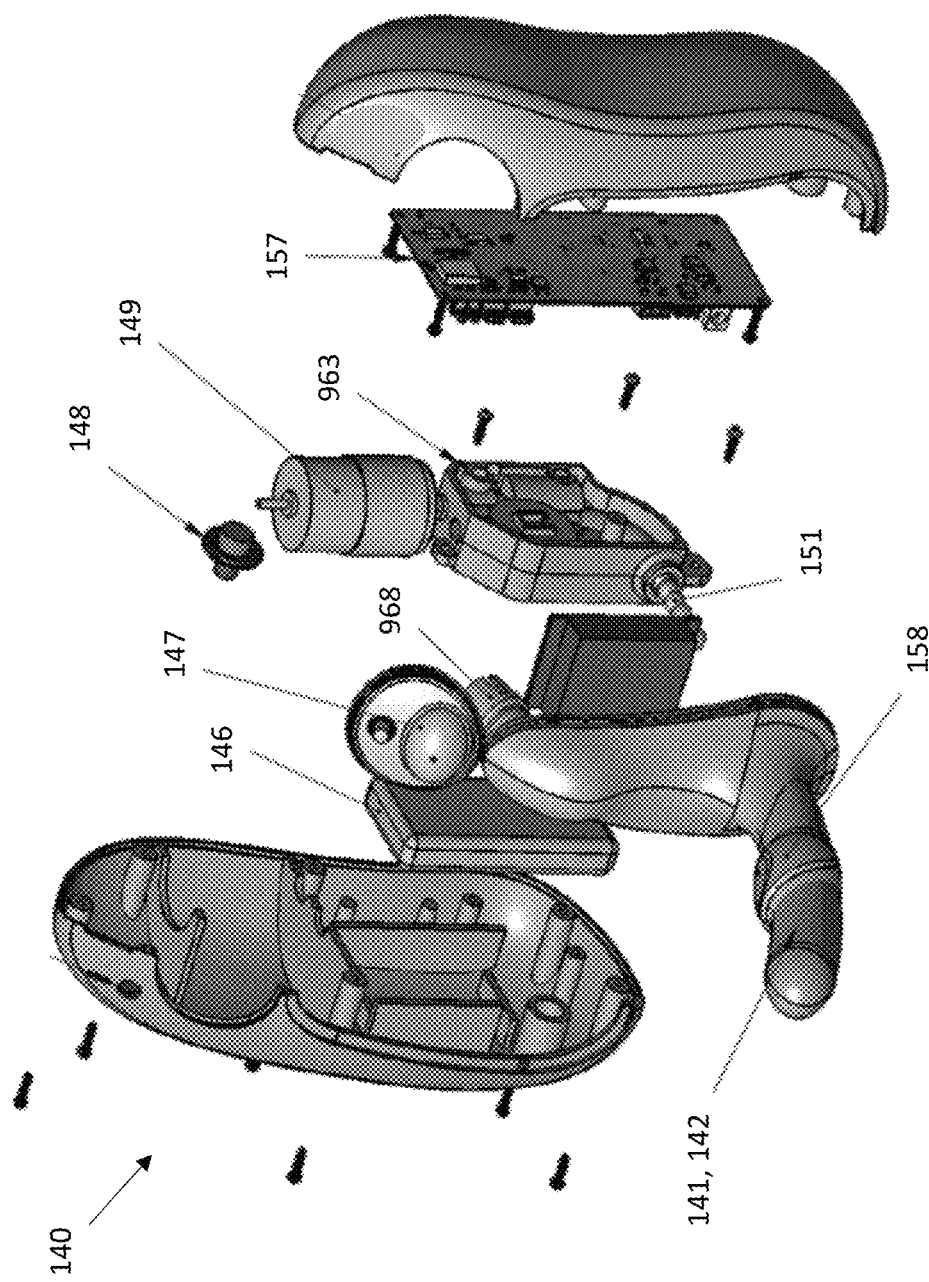
FIG. 8 is an exploded view of the male device.

Described herein are devices and systems related to sexual aids and systems that allow for remote communication between sexual devices and remote control of said sexual aids. The sexual aids or sex toys described herein include a male device and a female device. The system also includes methods of communicating between devices as well as methods for remote control of either male or female devices by a third party.

Female Device

In general, a female device described herein is configured to mimic a portion of the female genitalia and can be used for sexual stimulation of a user. The female device includes a flesh-like cavity that is able to accept a phallic-shaped member. The female device possesses two degrees of freedom; a constrictor axis that is able to apply a desired pressure to the cavity and a translation axis that simulates a stroking action. The female device thus includes a constriction and a stroke assembly, both of which will be discussed in detail below.

The female device includes an essentially tubular body with an opening and cavity disposed on one end. The cavity is expandable to accommodate a range of penis sizes. The cavity is lined with a removable flexible sleeve. The term "flexible sleeve" used herein refers to a covering that lines the cavity. In the broadest sense, the "flexible sleeve" can be constructed from any pliable material conceived of and readily available. In narrower terms, the "flexible sleeve" comprises a durable, flexible material that replicates the feel of human skin. It may also be desirable for the "flexible sleeve" to be made from materials that are largely impermeable. The sleeve is stretchable and pliable. In some examples, the sleeve may have corrugations that afford stretching and freedom to move in any axis.

The female device also includes a constrictor assembly that has two degrees of freedom: movement along the longitudinal axis of the shaft and a constrictor action on the cavity. In this example, the constrictor assembly is supported by guide shafts that run along the length of the female device. A stroke actuation assembly is able to push and pull the constrictor assembly along the length of the cavity.

In this example, the constricting action is realized with a clamshell constrictor, where the clamshell constrictor is able to alter the inner diameter distance to effectuate a constriction against the object contained within. The term "clamshell constrictor" as used herein refers to any two elongated concave surfaces that face each other and are able to alter the inner distance between the two elongate concave surfaces. In other examples, the clamshell constrictor are two pieces of aligned elongated concave surfaces that face each other having a hinged side and an unattached side that is able to periodically reduce the inner diameter between the two elongated concave surfaces that corresponds to a squeezing or constricting action. The clamshell constriction motion is controlled via a constriction actuator. The constriction actuator may be any assembly that is able to provide a constricting or squeezing motion to the clamshell constrictor.

The portion of shell that will be in contact with the cavity includes balloons that can be inflated to a firmness that will provide the desired amount of constriction about the cavity. A user will be able to adjust the amount of constriction using user controls located on the female device.

The female device also includes a stroke actuator. The stroke actuator is able to move the clamshell constrictor within the cavity along the longitudinal axis of the device, repetitively extending proximally and distally within the cavity. The term "stroke actuator" used herein may refer to any mechanism that is able to provide a stroking motion along a defined axis. In particular, a belt drive may be used to provide the stroke action for the female device.

Turning to FIG. 1-5, a female device 100 is shown. Female device 100 includes an elongated body 101 having a proximal end 102 and a distal end 103. Proximal end 102 includes an opening 104 that is in connection with a sleeve 105. Device 100 includes a lip 117 for maintaining and anchoring sleeve 105 within device 100. Sleeve 105 lines the inside of device 100 and may be removed and replaced. The opening and sleeve may be constructed from soft elastomer that simulates the feel of real skin, but the sleeve and opening may be constructed from any soft and pliable material or combination of materials. The opening and the sleeve are also stretchable to accommodate a range of penis sizes as well as changing penis dimensions when in use. A pictorial of sleeve 105 by itself is shown in FIGS. 4A-E. Sleeve 105 may be pulled back and forth over the penis by the constriction assembly, which will be discussed below. The sleeve may be coated with a silicone or other material that prevents mineral oils or other lubricating compounds from leaching into the out surface of the sleeve over time. In some embodiments, the sleeve may have a ribbed or helical feature as shown in FIGS. 4D and 4E. The helical design may be more readily expandable and compressible, and thus reducing the force required to deform sleeve 105 while increasing the sensation inside sleeve 105. The helical design may also require less power which in turn reduces the motor and battery drain.

As eluded to earlier, device 100 can exert a constricting motion at a position along sleeve 105. In general, constricting motion is an action or movement that applies pressure to a desired location or object. Here, the constriction action is achieved with an upper and a lower constriction clamshell 106 and 107, respectively. When assembled, upper and lower clamshells 106 and 107 are coupled to and supported by guide shafts 117 and may slide in unison on guide shafts 117. A first motor 109 drives the constricting action of upper and lower shells 106 and 107. The constriction action is actuated with a single gear stage having a pinion 115 and sector gears 116. Sector gears 116 are arranged such that they are all driven by the single pinion 115. Constriction or loosening of upper and lower shells 106 and 107 occurs when sector gears 116 rotate guide shafts 117 in the appropriate direction which then acts upon upper and lower shells 106 and 107. Upper and lower clamshells 106 and 107 including a corresponding pawl coupled to one of the guide shafts 117 which holds upper and lower shells 106 and 107 when a desired constriction is reached.

Upper and lower shell 106 and 107 can be detached from the rest of device 100 for easier removal and/or replacement of sleeve 105. In some examples, only the upper shell is removable. In other examples, the upper and lower shell are removable from the device but also hinged with respected to each other. To provide constriction to sleeve 105, actuators can squeeze upper and lower shells 106 and 107 together. Further disposed on the underside of upper and lower shells 106 and 107 are inflatable balloons that are user controlled. A user can inflate or deflate the balloons to achieve the desired amount of constriction he wishes to experience. The inflatable balloons are typically filled with air but other gases or liquids may also be used to achieve the increased constriction effect. In one embodiment, the upper and lower shells are two hard plastic PC-ABS pieces that sandwich a silicon balloon part or parts and tubing assembly connects the inflatable balloons to an inflator mechanism. In some instances, it may be possible to save parameters for the interactive device on the device to be set for future use.

The second degree of freedom that device 100 provides is a translational axis motion along elongated body 101. Upper and lower constriction shells 106 and 107, along with the inflatable balloon or balloons, can glide along sleeve 105 on guide shafts 117, which is actuated by a stroking power transmission 111. Stroking power transmission 111 includes a belt drive 112 and a rack and pinion drive 113. A second motor 110 drives the stroking power transmission 111. Selection of transmission ratios are set by balancing power consumption, noise, force, and volume parameters. In this embodiment, a first stage is the belt drive 112 having an output ratio of 7:1, and a second stage of the rack and pinion drive 113 with an overall transmission ratio of 6:1.

The female device may also include position sensors 122 that are directly coupled to the drive mechanism. The position sensors 122 allow for precise dynamic control of the position control loops. Also, unlike incremental encoders, direct coupling to the drive mechanism prevents the possibility that the feedback sensor fail to report the actual position of the sliding upper and lower shells 106 and 107. In this embodiment, each actuating assembly has a coupled magnetic Hall sensor that provide stroke and constriction position signals. The sensors are placed in the corresponding rotating parts of both motion-producing assemblies; one on a sector to measure constriction position and one on a gear that idles on the driven rack to measure stroke position. In some embodiments, when the sensor components for the stroke motion and the rack are assembled into the actuator assembly, the sensor components and the guide shafts may be located such that magnetic orientation is correctly coupled to the rack, otherwise, the sensor output will cross over from maximum to minimum value within the operating stroke of the rack. In production, a simple assembly tool will be used to guarantee that the rack and sensor components are correctly positioned such that they will function in an ideal range.

In general, the components for the female device is supported on a single molded plastic bracket. The single molded plastic bracket supports both power transmission assemblies as well as providing mounting support for other internal components such as sensors, battery, and so forth. The female device also includes a removable covering 108. The removable cover allows a user to remove and replace the sleeve and for cleaning the device interior space. The upper and lower shells form the top and bottom half of the device and support the corresponding electrical components contained within. The covers can be made from durable, not-easily breakable material and in some instances, may be covered with a softer, more pliable material.

The female device also includes other components for proper function. The female device includes a battery for powering the transmission assemblies. Often a lithium ion battery pack is used. The female device also includes a printed circuit board (PCB) assembly supporting a microcontroller, a power amplifier, a battery management components, wireless communication electronics, and analog control components. The female device may further include a heat spreader and/or heat sink for providing adequate thermal capacity for one full battery discharge period. One full battery discharge period may be anywhere from 15-45 minutes, longer in some case.

Finally, the female device includes a host of user controls. The female device includes a thumbwheel interface 126 that allows the constriction assembly to be positioned anywhere along sleeve 105. A pressure sensitive control 128 may also be present to allow a user to control the amount of pressure exerted on the sleeve. The female device may also include a pump control feature 129 that is able to inflate the balloons attached to upper and lower shells 106 and 107 with several presses and deflate the balloon pressure with a pressure release mechanism. Also included in the female device are up, down and select keys 131 that allow a user to pick which operating mode the device function in as well as an on/off switch 130.

Male Device

A male device as described herein is designed to mimic a portion of the male genitalia and can be used for sexual stimulation of a user. The device includes a shaft in connection with and supported by a device main body.

In general, a male device is able to mimic a portion of the male genitalia region. One embodiment of the male device includes a main body region, a tubular body region disposed on the main body, and a bead drive mechanism contained within the tubular body and the main body and able to travel between the two regions.

The tubular body of the male device is a semi-rigid shaft that is in the shape of human male penis. The term "tubular body" as used herein refers to a tube having the approximate shape and size of human male genitalia such as the penis. Tubular body may also include the shaft, glans, meatus, testicles, root (e.g. radix), and so forth. The tubular body includes a proximal end and a distal end, where the proximal end corresponds to the base of penis and the distal end of the tubular body corresponds to the tip of the penis.

The shaft is attached to the main body at a proximal end and is able to flex and bend (in a manner comparable to a real penis). The term "shaft" as used herein refers to the long portion or length of the tubular body. In some cases, the term shaft may refer to the entire length of the tubular body. Shaft may also be used to refer to a portion of the tubular body distinguishable from the tip of the tubular body and its base. A pliable sheath covers the shaft. The sheath is inflatable to mimic a range of different penis sizes.

Also disposed on the shaft is a massager sub-assembly. The term "massager subassembly" used herein refers to any additional arrangement disposed on the shaft of the male device that is able to provide a simulating output. The massager sub-assembly may have the same material as that of the shaft or be of different material to provide a variation in sensation. The massager sub-assembly can provide a general massaging effect such as vibration, pulsations, undulation, heat, and so forth to the area that it contacts. The massager sub-assembly may also provide pressure against the surfaces that it comes into contact with. The massager sub-assembly may also be able to rotate with respect to the shaft. In some examples, the massager sub-assembly is made of a rigid core that is in contact with the shaft. The outer surface of the massager subassembly is composed of inflatable portions or balloons. The inflatable portions can be manually inflated to the desired girth. The massager sub-assembly is disposed on the length of the shaft. In some examples, the massager subassembly is able to extend and retract along the shaft of the device. "Extend and retract" herein generally means moving along the shaft of the male device where expending means moving to a more distal position with respect to the base of the shaft and retracting means moving to a position closer to the proximal end of the tubular body.

The male device includes a bead drive mechanism. The bead drive mechanism functions to replicate the thrust and stiffness components of an erect penis. The bead drive mechanism includes a bead chain that is able to extend and retract within the tubular body through a drive gear. The term "bead drive mechanism" broadly can refer to a drive mechanism that utilizes beads or a series of bead to actuate a particular motion or action. More particularly, the "bead drive mechanism" here refers to an array of beads that are arranged in a line or single axis that is able to move along the single axis. The bead drive mechanism may include a series of beads strung on a flexible wire. It is also possible that the string of bead are connected to each other through magnetic forces; in that case, no string or wire may be needed. A compressed spring preloads the series of beads and keeps the bead assembly in compression and still allows the chain to bend locally about the cable's fulcrum.

A drive gear is coupled to the bead assembly and is able to actuate the bead assembly about the longitudinal axis of the shaft. The term "drive gear" used here in can refer to any mechanism that is able to drive the bead assembly. Drive gear can be any mechanism that includes a toothed or ridged gear that couples to another gear or element for engaging and transmitting rotary motion. Drive gear may include straight-cut gear, helical or worm gear, herringbone gear, bevel gear, spiral teeth gear, or one with internal gears. The gear drive may also refer to a mechanism that does not use a wheel and is able to produce a reciprocating motion by other means.

The massager sub-assembly may be coupled to the bead drive mechanism. Also coupled to the bead drive mechanism is a position sensor. The position sensor reports back on the relative position or configuration of the bead assembly. The relative position of the bead assembly will be important in an interactive scenario. The term "bead chain sensor" used herein refers to a sensor that is generally able to detect the location of the bead chain at a particular point and extrapolate the position of the bead chain with respect to the rest of tubular body. The bead chain sensor may be physically coupled to the bead assembly and/or the drive gear. For example, where the bead chain sensor is able to "count" the beads that have moved past it in a particular direction. It may also be possible to have a bead chain sensor that does not come into contact with the actual bead chain or bead drive, for example, an optical sensor.

The main body region includes a clitoral stimulator. As the name suggests, the clitoral stimulator is intended to contact a region on a female user's body that corresponds to her clitoris when she uses the male device. The clitoral stimulator may be any mechanism that provides a stimulating output to the region directly adjacent to it. For example, vibrations, undulations, pulsations, kneading motion, and other outputs may be provided. The clitoral stimulator may be manually controlled by the user during use of the male device in a non-interactive mode. In other examples, the clitoral stimulator may also be operated as part of an interactive session where an outside party may control the vibrator as part of controlling the outputs of the overall male device.

In general, any of the apparatuses (and particularly the devices adapted for use by a female) may include a clitoral suction feature in combination with any of the mechanical systems described herein. A clitoral suction feature (e.g., clitoral suction cup, pneumatic clitoral suction cup, etc.) may be comprised of a suction cup (pneumatic suction cup) that may fit over and/or around the clitoris and may provide multiple levels of gentle suction with or without contacting the clitoris. Pneumatic suction can be constant at varying levels, pulsing, or can operate in one or more pre-set (and user selectable) routines. The operation of a clitoral suction feature may also be synchronized to tele-robotic movements of a partner connected over the Internet, and/or may be activated remotely by a partner.

Any of the apparatuses described herein, including the male and female devices, may include a twisted-string transmission or drive. For example, a twisted-string transmission (see, e.g., US2008/0066574 and Godler et al, "Modeling and Evaluation of a Twist Drive Actuator for Soft Robotics", in Advanced Robotics, Volume 26, Issue 7, 2012, page 765-783) may be used in addition to or instead of a bead drive as described above. A pair of twisted-string transmissions may be used to push and pull an element of the apparatuses described herein. In general, in a twisted-string transmission, a pair of cords, when twisted, shortens the overall length of the combined cords. By connecting a motor to one end of the cords and maintaining tension (e.g., with a spring or other element) at the opposite end, a cheap, rapid actuator is made possible. For example, in an apparatus including a sliding member (such as the massaging sub-assembly described herein), a twisted-string transmission may be used to help actuate the sliding member. Any appropriate string or cord (including nylon cords, e.g., Dynema) may be used.

The majority of the systems control for the male device is contained within the main body. The systems control includes a printed circuit board assembly. The printed circuit board assembly coordinates the control of the male device functions. The printed circuit board assembly may include a microcontroller, a power amplifier, battery management components, components for the wireless communication, and analog control components.

Also disposed on the male device main body are user controls. User controls include buttons, key pads, switches, and toggles for affecting the output of the male device. An on/off switch is disposed on the body of the male device. Other user controls may include control for adjusting the position of the massager sub-assembly. Also, a user may control the amount of inflation to the balloon component of the massager sub-assembly. Finally, there may be user controls on the device for selecting different operating modes for the male device.

FIGS. 6-11 show a male device 140. Male device 140 includes a shaft 141 and a device main body 143. Shaft 141 includes a proximal and a distal end where its proximal end is coupled to main body 143. Shaft 141 houses a portion of a portion of a bead assembly 151 and support a massager sub-assembly 158. Device main body 143 is protected by a left and a right cover 144 and 145. Left and right covers 144 and 145 house or support most of the components for male device 140 including a remaining portion of bead assembly 151, a motor 149 for driving device 140, a battery 146 for powering motor 149 and other components for device 140, a series of user controls 148, and a pump 147.

Device main body 143 also houses a printed circuit board (PCB) assembly 157 for controlling the function of device 140. PCB assembly 157 may include a microcontroller for coordinating the actions of various components of device 140 and registering and responding to user inputs. PCB assembly 157 may also include a power amplifier for when a user desires to have more stimulation to be provided. Finally, PCB assembly 157 may provide control of analog and digital electronic components such as those for controlling wireless communication of device 140 or controlling a stimulus-output component, such as the vibrator or massager components.

Device 140 generally provides a reciprocating and a vibratory output. In some embodiments, angle sensors are included to provide closed-loop feedback to and from the microcontroller. In one example, an accelerometer can be incorporated into the device for measuring acceleration, where the value measured can provide positional information. User controls 148 are also housed in or supported on main body 143 of device 140. One such user control is a thumbwheel control that allows the user to position massager 158. A user using the thumbwheel control may position massager 158 anywhere along shaft 141. The user may set an initial position for massager 158 and positions relative to the initial position that is most pleasurable for them. In some examples, positional information of the massager may be recorded within device 140. Another user controlled feature is a pump 147 feature that is disposed on a front face of device 140. Pump 147 can inflate Shaft 141 is covered by a sheath 142. Typically, shaft 141 is semi-rigid and may pivot with respect device main body 143. The stiffness of shaft 141 is intended to simulate the internal structure of an erect penis. Shaft 141 is flexible and able to bend. In some examples, the shaft is able to flex between a thirty degree to one hundred eighty degree angle. Shaft 141 is supported by two cylindrical features 170 on the left and right shell 144 and 145 and is able to rotate slightly with respect to the cylindrical support features 170. The unique mechanism for achieving the feel of an erect penis will be further discussed below. In general, a sheath is case or covering that fits over the shaft and manufactured from a soft, pliable material. Sheath 142 may be any soft elastomeric material and in some case a soft silicone. Because sheath 142 simulates the functionality of a real penis, sheath 142 may expand and shrink in size. In one embodiment, the sheath may have a girth range of 32 mm up to approximately 50 mm Sheath 142 also include internal corrugations that provide for smooth expansion and compression as sheath 142 expands in size during use.

Figure 9B:
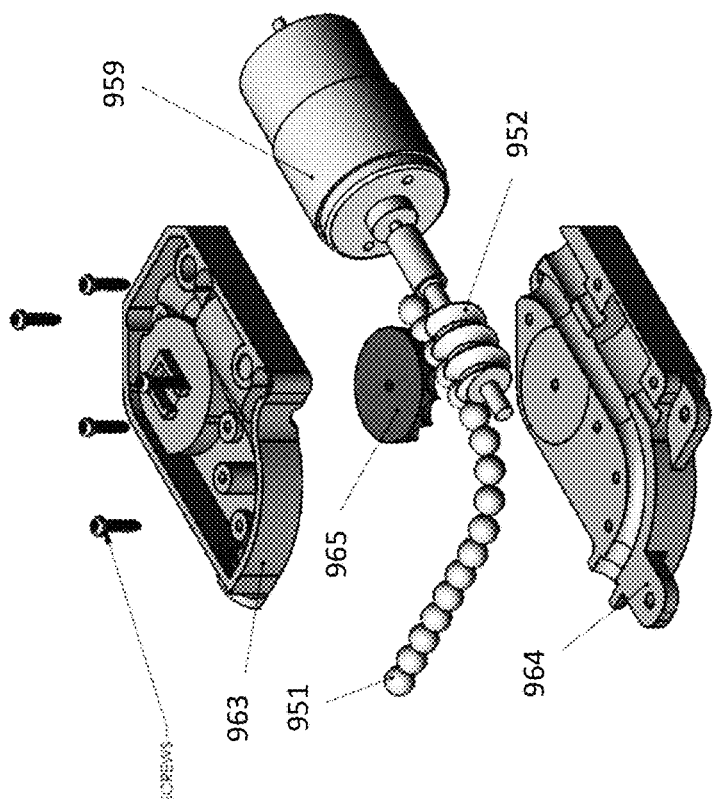
FIG. 9B shows an exploded view of a power transmission assembly of the male device.
Figure 9A:
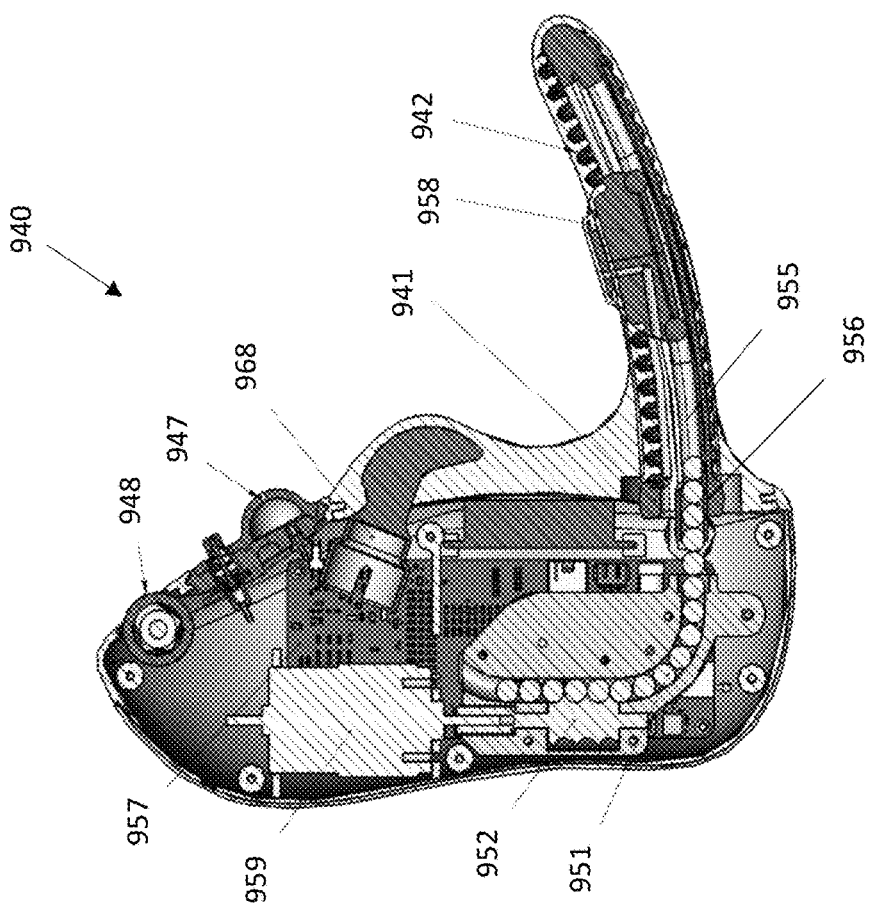
FIG. 9A a cross-sectional side view of the male device.
Figure 10:
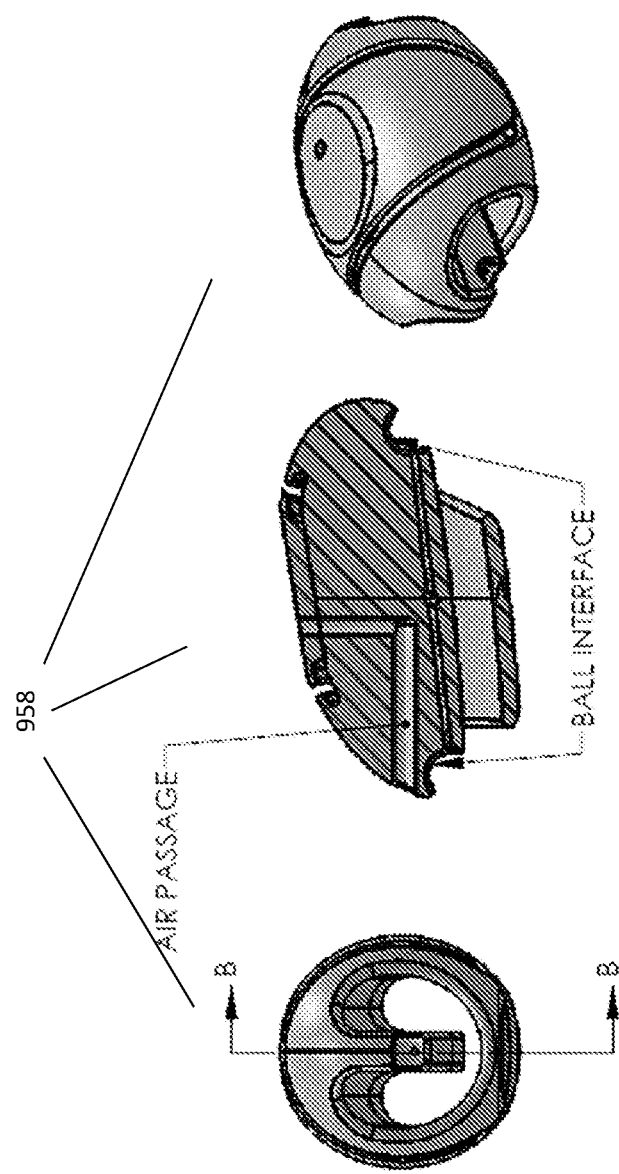
FIG. 10 shows a series of drawings of a massager subassembly including a front view, a cross-sectional view, and an offset top view (going from left to right) of the male device.
Figure 11:
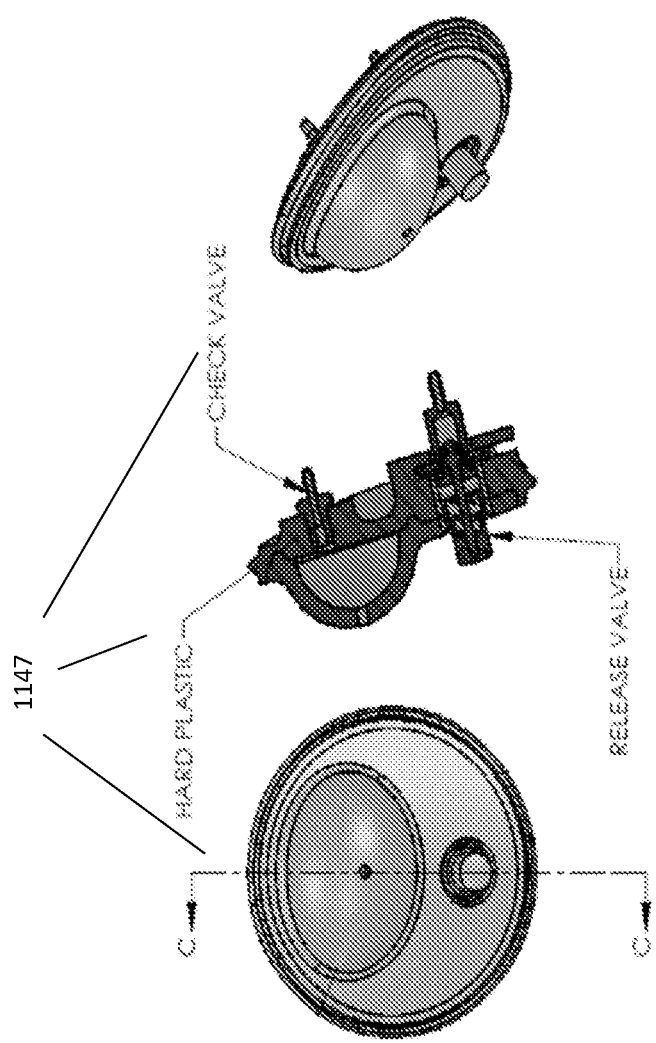
FIG. 11 shows a series of drawing of a vibrating actuator; including a front view, a cross-sectional view, and an offset top view (going from left to right) of the male device.

Male device 940 simulates penetrative sex using a unique bead drive mechanism 950 that includes a bead assembly 951 and a helical drive gear 952 assembly as shown in the cross-section of male device 940 in FIG. 9A. Bead drive mechanism 950 is partially housed in main body 943 and extends into shaft 941. The portion of bead drive mechanism 950 situated within main body 943 includes a left and a right housing 963 and 964.

Bead assembly 951 includes a series of hard beads 954 strung together on a cable element 955 and is "pre-loaded" with a tensioning spring 956. Tensioning spring 956 keeps the individual balls in compression until extension is desired. In some embodiments the spring 956 can be at the end of the beads 954 chain before a last bead and crimp. Spring 956 ensures the stability of beads 854 chain while the bead assembly 951 is under compression. The bead assembly 951 is able to bend locally about the fulcrum of cable element 955. While the series of hard beads 154 may be made from any suitable material and shape, in the embodiments shown, the beads generally have a spherical shape. In some embodiments, the beads are of Teflon or nylon balls. The actuator using Teflon or nylon balls ranged from 5.5 to 8.5 pounds of output force.

Helical drive gear 952 drives bead assembly 951. Helical drive gear 952 is coupled to a motor 959 through a motor shaft 960 and a drive gear shaft 961. In use, motor 959 actuates helical drive gear 952 to rotate and catch bead assembly 951 within its grooves, and depending on the direction of rotation, bead assembly 951 is pulled in or pushed out relative to helical drive gear 952 and main body 943. The thrust forces of helical drive gear 952 are modulated by a sensor gear 962 that can detect the location of helical drive gear 952 relative to bead drive actuator 951. Left and right housing 963 and 964 support and position helical drive gear 952 and sensor gear 962.

Sensor gear 962 has precision scalloped features that are modulated by bead assembly 951 as helical drive gear 952 moves bead assembly 951. Using an absolute position sensor that is directly coupled to bead assembly 951 provides precise dynamic control of the position control loop and eliminates the chance that the feedback sensor inaccurately reports on the actual position of the bead assembly, which can occur with incremental encoders. Sensor gear 962 includes a magnet having magnetic polarization perpendicular to the axis of rotation of helical drive gear 952. When sensor gear 962 and bead assembly 951 are assembled into bead drive mechanism 950, sensor gear 962 and bead assembly 951 may be arranged to ensure that correct magnetic orientation is achieved, otherwise, output from sensor gear 962 will cross over from maximum value to minimum value within the operating stroke of bead assembly 951. In some case, a neodymium iron boron magnet is used. Sensor gear 962 is fixed into positioned abutting right housing portion 964. In one embodiment, the sensor gear can make close to a full rotation as 11 beads move past it; this translates into an 87.3 mm stroke of the massager along the shaft.

Next, a massager sub-assembly 958 is disposed on shaft 941 as shown in FIGS. 9A and 9B. Massager sub-assembly may rotate relative to a portion of shaft 941, which may create the sensitive of a bending finger. Massager sub-assembly 958 has molded pieces made of rigid, semi-rigid materials at are assembled around an inflatable balloon 966. Inflatable balloon 966 faces outward and is in mechanical contact with the user. Massager sub-assembly 958 includes an air passageway 965 that is able to inflate inflatable balloon 966. Massager sub-assembly 958 is coupled to bead assembly 951 through bead interface regions 967 on the bottom surface of massager sub-assembly 958. In some embodiments, bead interface regions 967 couples with the last or the second to last bead of bead assembly 951. In some embodiments, the bead drive mechanism is mechanically coupled to the bead assembly through magnetic means. Coupling using magnetic elements for coupling has the advantage that the bead drive mechanism may be completely sealed. In this arrangement the sheath may be unnecessary and the massager sub-assembly can move directly along the sheath.

Male device 940 also includes a pneumatic pump 947. Pump 947 is able to inflate balloon 166 with several presses. Pump 947 has includes a release valve that allows a user to adjust or release pressure from balloon 966.

Finally, male device 940 includes a clitoral stimulator 968. Clitoral stimulator 968 is positioned above shaft 941 on the front face of device main body 943. The location of clitoral stimulator 968 corresponds to the location of a female clitoris when male device 940 is in use by a female. Clitoral stimulator 968 is able to provide a stimulating output such as a vibration. It will be possible for a user to adjust the vibrating feature to their desired tastes using a user interface located somewhere on the male device. In some embodiments, the vibrator motor will be current controlled using either an analog slider, switch, or button such that a user can control the amount of current supplied to the motor. The increase or decrease in current flowing to the vibrator motor will correspond to vibrator output.

Male device 940 is able to deliver a stroke with a pre-determined amount of force using a stroke actuator. The power transmission from bead drive mechanism, in some embodiments has an effective drive ratio of 11:1, meaning that it takes eleven turns of the motor shaft to traverse an output stroke. Operating at 12V, the actuator can produce up to 9.5 pounds of force in tension or compression. In some embodiments, a pressure pad or control is provided for controlling the stroking motion. In some examples of this embodiment, the pressure pad may be implemented as an analog signal to manually control stroke motion. In use, when the pressure pad or other control is manipulated, the user may increase speed or depth, be able to adjust position, or a combination thereof.

While the bead drive mechanism thus forth described is intended to be used in a sexual aid that mimics a portion of the male genitalia, it has been envisioned that the bead drive mechanism can be used in a variety of applications in addition to being used in the device described above. Variations of the bead drive mechanism can be used in smaller insert-able toys or larger massage toys (e.g. p-spot or g-spot massagers).

Common to Both Devices

Both the male and female devices include some form of closed-loop control. While closed-loop systems utilizing sensors and actuators are fairly common in other areas such as robotics and diagnostics, few sexual aid devices currently available employ these closed-loop control features. Both male and female devices provide for actuators and sensors (albeit slightly different based on the desired effects sought for the two different devices). The female devices includes actuation for stroke and constriction type motion while the male device provides for a stroke and a vibratory output. Sensors are associated with each for providing feedback and control via the microcontroller.

In some of the female and male device embodiments, a display is disposed on the device. The display would allow for showing the user the status of the device and allow the user to more easily configure the device to their desired specifications. The display can be a simple LCD display able to display some graphics, show text and icons.

Both male and female device will include some forms of user interface for controlling the corresponding device. For example, in the female device (which simulates female genitalia), the user may use the controls on the female device to adjust the stroke rate and amount of constriction, and in the male device, the user will be able to adjust the stroke rate and the vibration level output. A user, using controls either on the actual device or via the audio dongle, may also be able to record and later playback a session. The device's firmware will be able to store recorded session and update control set-points in non-volatile memory. A user may change the control set-point by manually adjusting the stroke speed limit potentiometer, which scales the position set-points linearly as they are received. Finally, the devices may include a full or an abbreviated keypad for entering authentication information; alternatively, a user will be able to enter authentication information using the audio dongle.

Both female and male device may include angle sensors that can measure the position of the actuators to provide closed-loop feedback. The initial position (e.g. zero value) of both female and male device may be set with a potentiometer such that the firmware does not need to store this information. In the case of the stroke actuators, they will move symmetrically with respect to this initial position.

Both male and female devices will have certain safety features to protect the user. A kill-switch will be available and will disconnect the device's battery when activated. In some examples, the firmware will also support a dead mode, where all the motors are deactivated. In other examples, the devices may be also include a system check routine to ensure that every component is functioning properly prior to use.

Alternative Embodiments of the Interactive Sex Toys

As mentioned in greater detail herein, either the male or female devices (e.g., the device emulating the male physiology or the device emulating the female physiology) or both may be configured for communication with one or more other devices to control or modify activity of the device based on input from the remotely-located other device. For example, a male-emulating device may receive input controlling the inflation or motion of the device, e.g., controlling or modulating the movement and/or position of the device's massager sub-assembly including the expansion/inflation of the massage sub assembly, and/or the movement and/or position of the bead drive moving the massage sub-assembly. This control may be based on feedback received from a female-emulating device, reflecting the position and/or movement of a penis within the female-emulating device. Similarly, a female-emulating device may receive input controlling the position and/or movement of a haptic (e.g., a clamshell constrictor and constrictor actuator gear driving constriction, and/or a stroke driver reciprocating the clamshell constrictor proximally and distally; the input may originate from a male-emulating device having sensors that translate into output driving or modifying activity.

In any of these variations, the controlling/modulating input may not be from a male- or female-emulating device, but instead from a streamlined input device that includes controls providing the remote control and/or modulation of a particular device. These device may be handheld and/or may be worn (e.g., as a ring, glove, etc.), and may be referred to as remote input devices.

Figure 37:
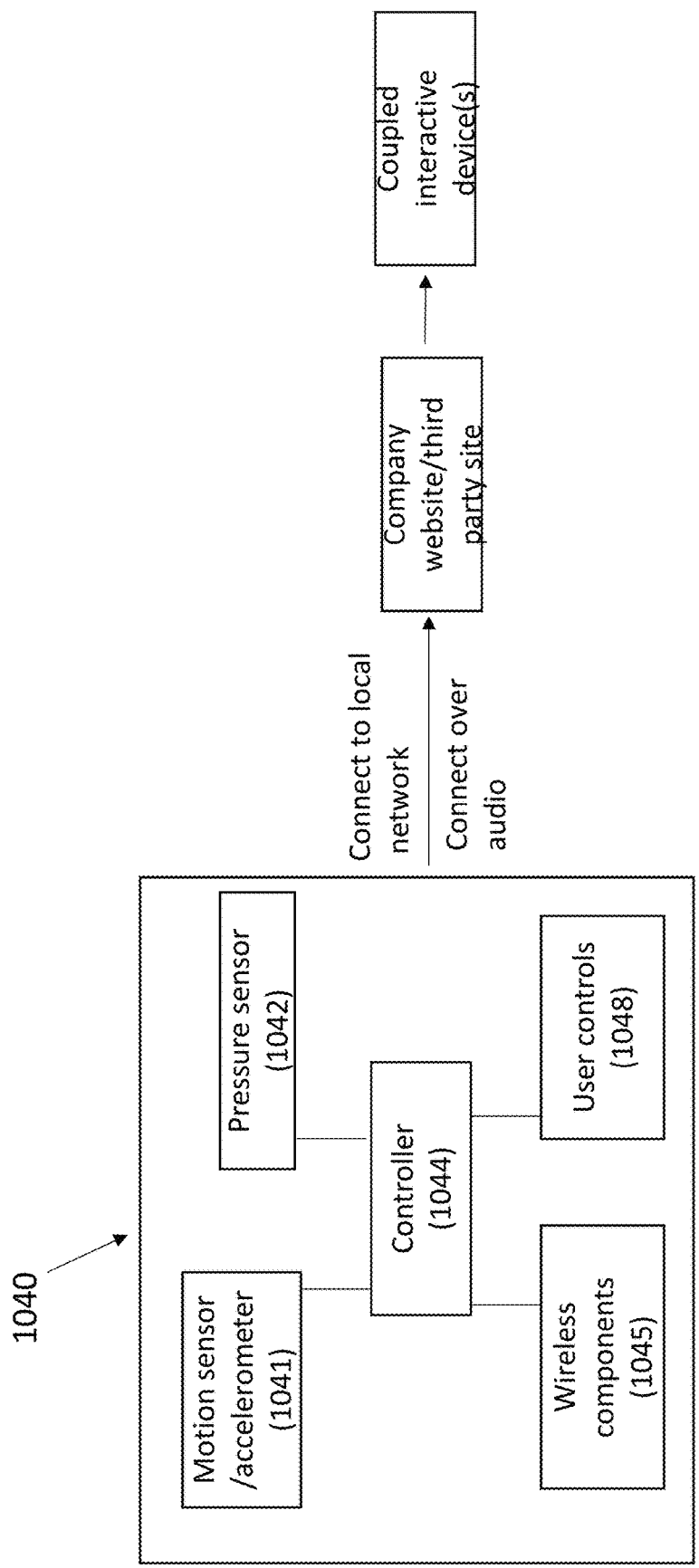
FIG. 37 is a schematic of a scaled down version of the male device that is able to provide gestural outputs that can be communicated to coupled interactive devices.

For example, a remote input device may be modeled after a male device that is streamlined, as shown by the schematic in FIG. 37. The device shown 1040 may be used in conjunction with a male-emulating or female-emulating device to sending controlling signals to one or more other devices. Device 1040 may be useful, for example, by a webcam model who wants to be able to interact with clients operating a female-emulating device, but not have to use a male-emulating device (e.g., a full version of the male device) at all or for an extended period of time, which may be uncomfortable or even painful. The device 1040 is may include gestural inputs/outputs such as sensors that are able to first detect the motions from a user and then subsequently wirelessly transmit that motion to a coupled device or devices, where the gestural outputs are received by the coupled device or devices and then applied by the coupled device or devices to a second or third user.

The device 1040 may include a series of sensors, such as motion sensors 1041 or pressure sensors 1042, that is able to detect certain hand gestures of a wearer. The device 1040 may be used with one or more tethered female devices that mimic the female genitalia. First, the device 1040 is able to provide a stroke type motion. In order to provide such a sensation to a wirelessly connected device, device 1040 includes sensors, such as an accelerometer that is able to sense, retain, and/or transmit detected acceleration and deceleration of the stroke that the wearer is implementing.

Device 1040 may also include a pressure or squeeze motion sensor. In one example, the pressure sensor may be an actual pad that is able to detect and transmit the amount of pressure the wearer is applying. The pressure sensor may be a single pad that is able to sense an overall/averaged pressure that the wearer applies. Or a series of individual pressure pads disposed on device 1040 that is able to sense more fine-tuned pressure outputs as made by the wearer. In the latter case, the device 1040 may be marked out showing where the pressure sensors/individual pads are located. In other examples, the pressure sensor component may be more akin to an inflatable balloon that is able to sense changes in internal pressure based on how hard a user squeezes. These devices may also include manual controls/inputs, such as buttons, sliders, switches, touch screens, etc.

The device 1040 may be either handheld or worn or a combination of being worn and held by the wearer. In a handheld version of device 1040, the device may have markings that denote where the sensing mechanisms and other controls are located such that the user may more precisely target the outputs on the corresponding female device.

The device 1040 may be in wearable form. A wearable form has the advantage where the user is not always having to grip an object, which may be tiring to the user's hand, but may have the disadvantage of having a longer adjustment period where the user is learning how the gestures that they are outputting translates to an output on the tethered device or devices. Also, there may need to be associated software and or hardware that is able to detect the gestures and translate the gestures to appropriate output on the tethered female device. A wearable device may be like a glove or partial glove, a wristband, or a combination thereof that the user may wear, where wearable device has sensors to detect motion or pressure relative to other sensors on the wearable device to provide a pressure output. The wearable device may contain straps or other coupling elements to attach the device to the user's hand or arm.

The device may be a combination of a handheld and wearable device. This combination version may be advantageous because certain sensors may be disposed on the handheld portion while other, potentially more fine-tuned gestures may be associated with the worn portion of the device.

As with the other male and female devices, the streamlined male device has wireless communication capabilities 1045 that allows it to communication with other associated devices by connecting to a local wireless network and then with the company or third party server. Device 1040 may also include a controller 1044 with appropriate electronic components for coordinating the movement sensed from the user and then outputs sent to the coupled interactive devices, as well as other user interface 1048 for helping the user interface with device 1040.

In another streamlined embodiment of an interactive sex toy, the interactive sex toy may be worn around the male genitalia. This version of the interactive sex toy may be in the form of a cock ring. This interactive sex toy may include a sensor or multiple sensors that may be able to detect a variety of environmental changes. For one thing, this interactive sex toy may be able to detect position of the penis and force that the penis is exerting. The sensors may be able to also detect the pressure that is being experienced by the penis with pressure sensors. It has also been contemplated that other types of sensors (examples include but not limited to temperature, moisture, stretch) may also be disposed on the interactive ring. The interactive ring may be made of any suitable material and may either come in a variety of sizes or may be adjustable.

An alternative design to the above described interactive sex toy may be worn by a female. This version of the interactive sex toy may be worn around the female midriff or closer to the female genitalia. The interactive sex toy will also include one or more sensors that are able to detect changes to the surrounding environment such as pressure, temperature, force, position, and so forth. This version of the interactive sex toy may include straps and couplers such that it may be secured to a torso, midriff, or genitalia region, the straps and couplers also allowing for adjustment to accommodate a variety of forms.

The interactive sex toys described above may all have wireless capabilities as the male and female devices that are described below. Information received by the sensors may be transmitted to a remote server and then to other interactive sex toy or toys. The interactive sex toys may also transmit and receive information to and from other interactive sex toy or toys directly.

Communication System

In brief, disclosed herein are methods for communicating and controlling the activity of a sex toy, where the method includes: initiating a wireless access point capability for the sex toy, wherein the wireless access point capability of the sex toy has a first digital address; and wirelessly accessing, using a wireless-enabled device, the sex toy via the first digital address; providing, from the sex-toy, a dedicated webpage including an input for receiving a second digital address and an access code, wherein the second digital address comprises the address of a locally-available wireless network; displaying the dedicated webpage; receiving at the sex toy, the second digital address and access code from the wireless-enabled device; and connecting the sex toy to the locally-available wireless network using the received second digital address and access code. The method also includes disconnecting the wireless-enabled device from the sex-toy before connecting the sex toy to the locally available wireless network, and turning off the wireless access point capability before connecting the sex toy to the locally-available wireless network. The sex toy is then able to connect to a remote server through a locally-available network and register the sex toy on the remote server. In an interactive mode, a second sex toy is able to receive the digital address from the first sex toy, and receive operational instructions for operating the sex toy. Once a session is established, the second sex toy or a plurality of other sex toys are able to interact with the first sex, each periodically sending session codes to the server host or a third party site that they are still active within the session. In some interactions, the sex toy is only able to connect one other sex toy. The sessions between the sex toy and one or more other sex toys may further be authenticated using a specific key linked to a serial number stored with the remote server for the sex toy. The host server may periodically check that each sex toy within a session is active and may terminate a session if one of the two sex toys within a session is no longer active or terminate a multi-participant session if only one participant is active or if a primary participant is no longer active. The latter case may be in reference to a "cam site" session where the remote server runs a third-party site. Finally, the remote server is able to remotely monitor the connectivity quality between the sex toys during a session.

The female and male devices described above can be used in a number of ways. Both the male and female device can be operated in a single mode without the need for connecting to a communication system. Both male and female devices can connect to another device, either male or female through a secured access point provided by the service provider website.

When either of the devices are turned on for the first time, the male or female device may act as an access point discoverable by a wireless-enabled device such as a smart phone, a laptop, a tablet and so forth. Once the wireless device has found the male or female device, a unique digital address corresponding to the male or female device may be sent to the wireless enabled device such that the wireless-enabled device is able to display a dedicated webpage to the male or female device. The dedicated web page is then able to authenticate the male or female device using a second digital address (such as a locally-available network address) and a unique access code via the wireless-enabled device. The male or female device is then able to connect to the locally-available network using the received second digital address and the access code. Once the male or female device has successfully connected to the locally-available network, it turns off its access point capability and disconnects from the wireless-enabled device.

The method that the devices use to communication with each other can be any appropriate technique available such as wireless technology (WIFI, Bluetooth), optical, auditory, and so forth. Any of the devices may include one or more processors configured to encode and decode signals transmitted and received to and from a "tethered" device. The signals may include input and output from sensors that may be coupled and integrated into the devices, such that the "tethered" device or devices may respond accordingly based on their corresponding sensor input and output. In some examples, the devices will be programmed with an SSID and password for connecting to a WIFI network for use in an interactive mode. In an exemplary embodiment, using WIFI, the devices may connect to the Company Server, other devices, and third parties via the internet. In instances where a WIFI connection is not available, the device can send and the Company Server may extract BFSK (binary frequency shift keying) encoded messages and process the authentication data from VOIP packets that it intercepts.

Figure 12B:
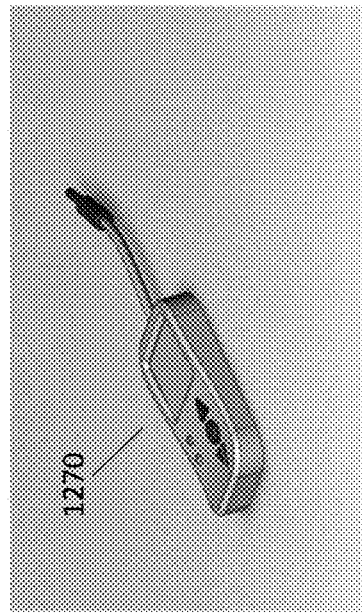
FIGS. 12A-B are two drawings showing an audio dongle.
Figure 12A:
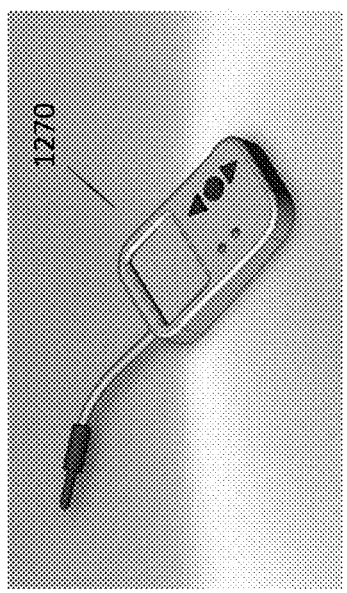
Figure 13:
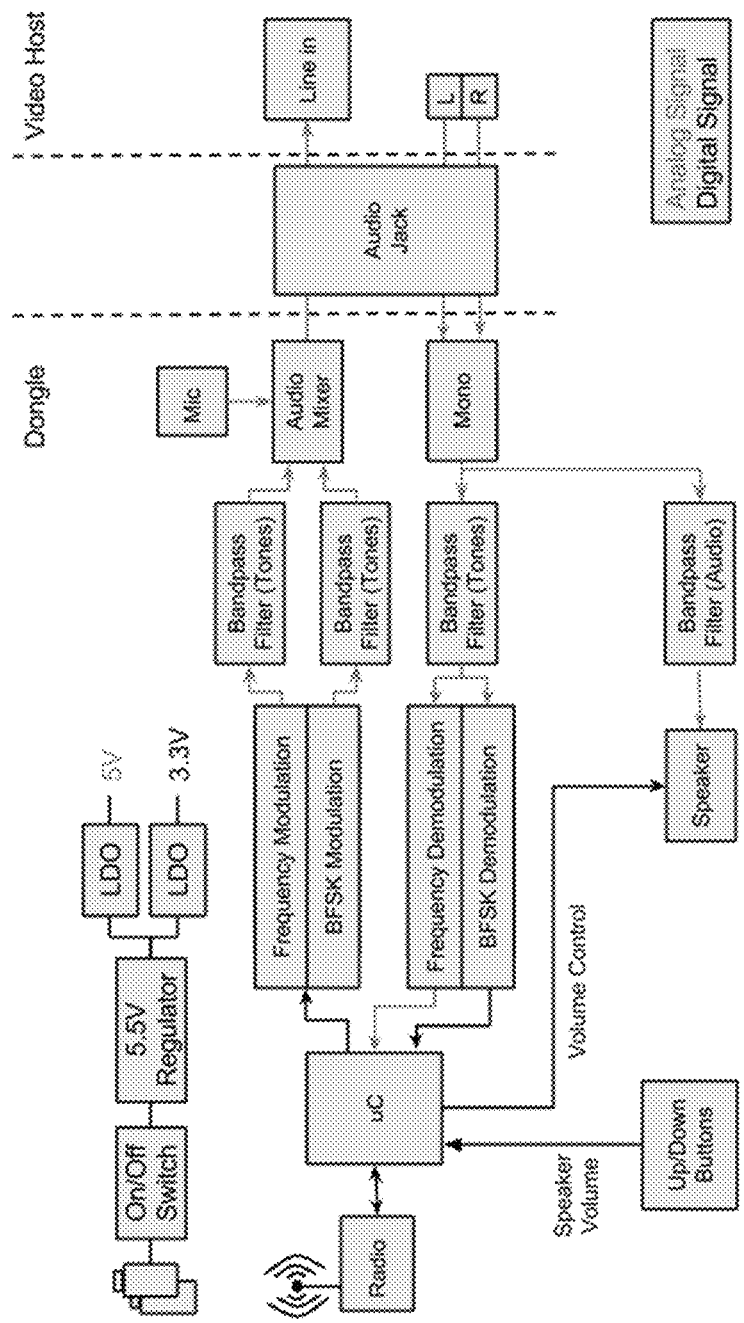
FIG. 13 shows a block diagram depicting components on the audio dongle.

In some embodiments of the system, the male and female device may require an audio dongle. An exemplary audio dongle is shown in FIGS. 12A and B. The audio dongle 1270 allow for a simpler device design because the controls and display are separate but attachable to the corresponding devices. While the connection to the audio dongle is most flexible when implemented as a wireless connection, a physical connection can also be use. The audio dongle 1270 contains a radio component. (The radio component of the audio dongle is to relay digital data packets from the interactive device to the audio dongle 1270 microcontroller using a SPI or I2C interface). It is envisioned that if an audio dongle is required, that each device has a uniquely paired audio dongle such that only the paired audio dongle will be able to communicate with the paired device. A schematic of how the audio dongle 1270 operates is shown in FIG. 13. Messaging between the audio dongle 1270 and the devices fall into two categories, one for motor control and the other for authentication. In an exemplary embodiment the audio dongle acts as an interface for communicating in the audio spectrum using a 2.4 GHz wireless IC.

As previously eluded to, the audio dongle is an audio interface for the interactive device. Functionally, the audio dongle converts communications from a digital format sent over a radio frequency to a frequency modulation and BFSK modulation (corresponding to motor control data and binary data, respectively). The audio dongle is able to mix modulate analog data with a microphone signal and send to a host device. The audio dongle is also able to detect and decode audible signals and play them on a speaker.

The audio dongle is used to encode data into an analog format. In the case of an FM signal, a transmitted frequency maps linearly to a control value. The digital format of messages sent using BFSK and over radio frequencies will be the same as the format used for WIFI messages. The BFSK encodes a binary value by the presence of either a mark (1) or space (0) frequency. Modulation frequencies are well represented using a sinusoid in the frequency domain, where it is approximated to a signal having the highest spectral density. The selection of how to modulate the signals will depend upon largely on balancing the total harmonic distortion (THD) of the sine output versus the cost and dependability. One possible modulation method is with a function generator IC. This modulation method uses a 5 MHz input clock, allows for offloading frequency generation from firmware. A digital to analog converter (ADC) or filtered triangle waves may also be used for modulation. The modulation method will depend upon trade-offs between the total harmonic distortion of the sine output and the cost of minimizing sine output distortion. Finally, the input signal may need to be concentrated and amplified so as to survive VOIP frequency content distortion.

Frequency demodulation can be accomplished with a dedicated IC or light digital signal processing (DSP) algorithm implemented on a microcontroller. The detected frequency is them mapped using a percentage of the voltage rail. In some embodiments, a NJM2211M chip, which outputs an analog voltage sampled by the ADC, may be used. The chip may also include a locked pin to indicate that the phase-locked loop (PLL) is actually tracking the input signal, and is used by firmware to indicate that the sampled frequency reading is not from noise.

BFSK demodulation may also be required. Demodulation can be achieved with a dedicated IC or light DSP algorithm implemented on a microcontroller. In one example, two dedicated low power tone decoder ICs are used; one tuned to detect the mark (binary 1) and the other space (binary 0) tones separately.

Bandpass filters may also be used to filter out unwanted noise. In some examples, four filters are included, where three are for passing tones only and the fourth for audio output only. The filters should allow for easy tuning of the cutoff frequencies and the quality factor (Q), as well having a pass bandwidth of about 2 kHz.

The primary function of the audio dongle is to interface with the audio portion of the male and female devices. Thus, the audio dongle also includes a PC microphone input and PC stereo output. In some examples, the microphone and the stereo output are on the same connector. The stereo input is summed to mono using a resistor divider and is then split into audio content and tones signals. The signal to the microphone comes from the audio mixer, which sums the user's microphone, the FM signal tone, and the BFSK signal tone. Because there is only one signal for both FM and BFSK at any point in time, there will be three inputs to the mixer; two for each of the tones, and one for the user microphone. Each input is assigned a weight using resistors and summed together before being DC coupled and sent to the audio jack. A power supply will also be included in the audio dongle. In one example, the power source for the audio dongle is disposable batteries. AA, AAA, or lithium coin cells are just exemplary power sources that can be used. The audio dongle also includes a microphone for capturing the user's voice. The audio is then transmitted to the other user or users. The audio dongle also includes a speaker for playing audio content received from the audio jack. Volume controls having non-inverting amplifier with variable gain may also be included. Finally, the audio dongle may also include a display. The display may show information from the interactive device that has been transmitted over the radio link.

The audio dongle will have associated firmware. The firmware may also control the speaker volume setting. The firmware includes pass through two 9-bit control values to and from an audio stream and the interactive devices. The firmware also includes pass through arbitrary digital packets to and from an audio stream and the interactive devices. The included firmware manages the motor control set-points, which updates the state of the motors on the interactive devices. The transmission of the motor set-point values are achieved over a wireless connection to the audio dongle, where the audio dongle modulates the values using analog FM and mixes the signal with the microphone signal prior to transmitting to the user on the other end of the VOIP connection. Demodulation of the signal occurs in the reverse order. Because the values are modulated with frequency modulation, the tones at the low and high band edges linearly correspond to 0 and 100%, respectively. For the female device, the control values are continuously transmitted one at a time in an alternating fashion, and updated every 50 ms (20 Hz). Because the female device has two control set-point value, the effective rate at which the control algorithms on the device can be sampled is 10 Hz. The male device will also update at a rate of 10 Hz. In other examples, another FSK decoder IC and utilizing twice the bandwidth can be used to communicate the control set-points simultaneously. The control set-point values are modulated with frequency modulation where the physical modulation is the same as that of the digital communication. Here, demodulation may use a FSK decoder IC with an analog output, which is then sampled by the ADC, where its frequency can be calculated. The bandwidth for the control set-point value are split in half for each control set-point, where each takes part of the dynamic range of a 12-bit ADC to allow for 512 values.

Messages between the interactive devices are transmitted between the audio dongles according to communication protocols that will be detailed below. In general, at the physical bit layer level, a BFSK scheme may be used. BFSK uses two tones at specific frequencies to represent a binary 1 (mark) or 0 (space). The microcontroller will assemble a predetermined number of bytes received into a block which is then written to the wireless chip, where it is wrapped into its packet structure and transmitted to the corresponding interactive device. The modulation interface is the same as that of the control set-point values (frequency modulation), while the demodulation interface is the transistor-transistor logic (TTL) output of two tone decoders.

Reliable signal exchange is a concern and must be balance between block size and cost. For example, in a block size of one byte, a parity bit should be used along with eight data bits. For block sizes larger than one byte, a cyclic redundancy check (CRC) should be used to validate the received data block. The optimal bit-width of the CRC itself will depend on the size of the data it is calculated on. For any particular device, associated firmware will keep track of and maintain statistics of messages received, failed and corrupted for diagnostic purposes. There are demodulation digital signal process algorithms that are amenable for microcontroller implementation that can calculate the discrete Fourier transform (DFT) of the input signal to determine the spectral content. This method is more efficient because there are two frequencies to measure. Also, the input signal can be under-sampled, allowing the ADC (analog to digital converter) to run at lower sampling rates in order to save power and reduce complexity. The results can be written to RAM with a DMA (digital media adaptor) channel and then analyze the signal periodically to demodulate.

Figure 14:
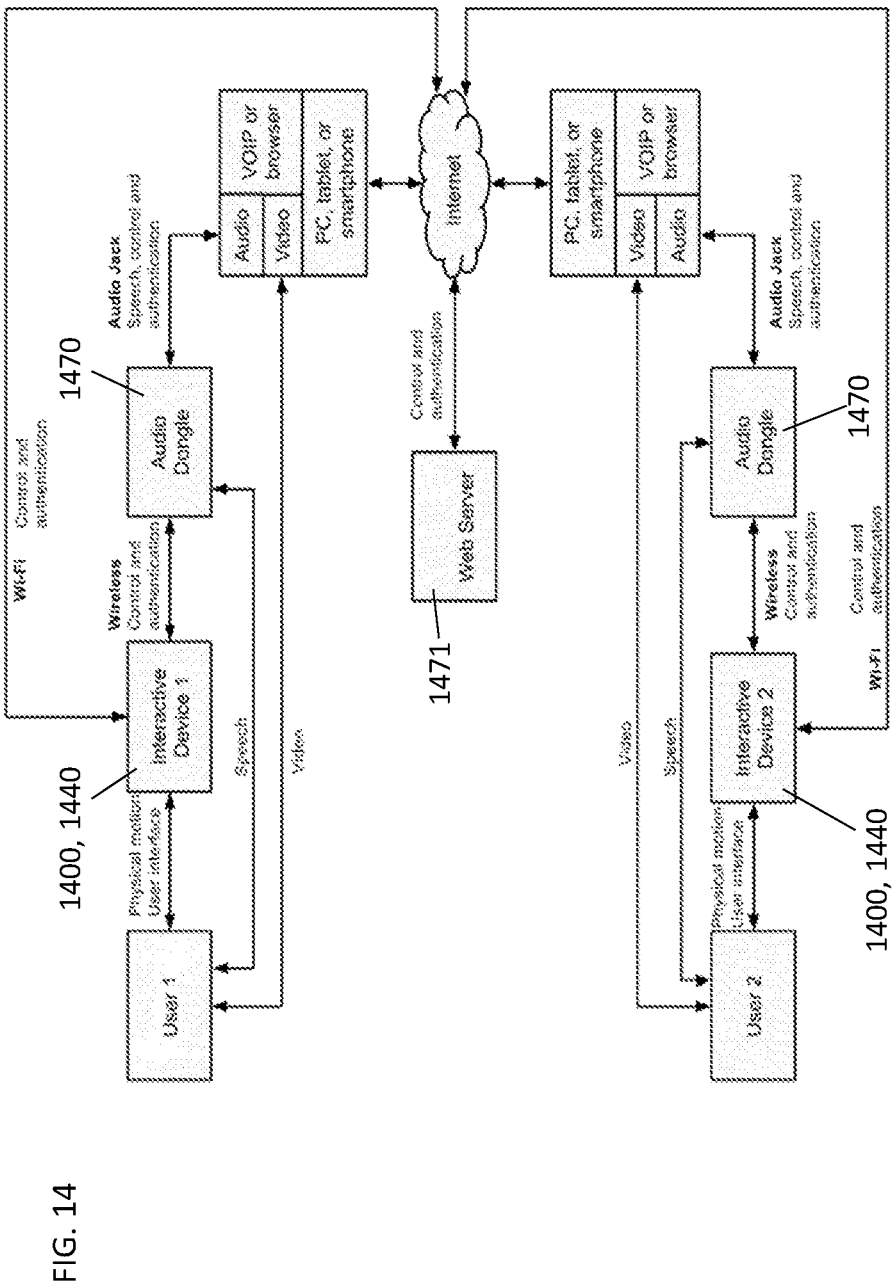
FIG. 14 is a schematic of how users may interact with each other through their interactive device.

Use of both male and female devices may be initiated in the same way. A block diagram of how two interactive devices 1400 or 1440 connect to a Service Provider's Web Server 1471 and how the interactive devices communicate with each other is shown in FIG. 14. When turned on for the first time, the male or female device will receive an authentication message from the Service provider to enable the device to be used in an interactive mode. Once authenticated, the device can receive validated session IDs for initiating an online session. The devices, either on its own or with the aid of the audio dongle, will also be able to track usage of the device, record sessions, and/or replay recorded sessions.

There are several steps associated with authenticating the device when first used. The device firmware may retain the device's communication modes, which includes online, online assist, offline, and offline default modes. The online mode, where the device is able to connection to the Service provider, can be authenticated through a WIFI connection. In the online assist mode, a shared WIFI connection is established where the device acts as an access point for the purpose of authenticating the device. In the offline mode, the device can be authenticated through audio means (using the audio dongle 1470). Finally, when the device has not been authenticated and is offline, the device can only run recorded sessions that are pre-programmed into the device memory.

Next, neither male nor female device will work in any interactive mode without the Server providing a session ID. The Server will manage the allowable video and device controls based upon the status of each device, whether the device is monogamously paired to another device or if it is free device. In an interactive session, the control set-points (sent from the other device or controller) for the device will be received from either the audio dongle or the WIFI connection. The actuator positions will then be periodically transmitted. In some embodiments, the device will transmit a position, pressure, or vibrational signal ten times per second to the other device(s), and the other device(s) will, in response, update their corresponding control loops. The interactive functionality is only allowed while the firmware is receiving appropriate interactive authenticated signals (a.k.a heartbeat messages) from the Server. In the event that the "heartbeat messages" stop being received, or if a stop session signal is received, the control loop will halt output, return to an initial set-point position, and stop transmitting sensor readings. Finally, statistic on the messages received, failed, and corrupted may be stored in the device's or the Server's firmware for diagnostic purposes.

Figure 15:
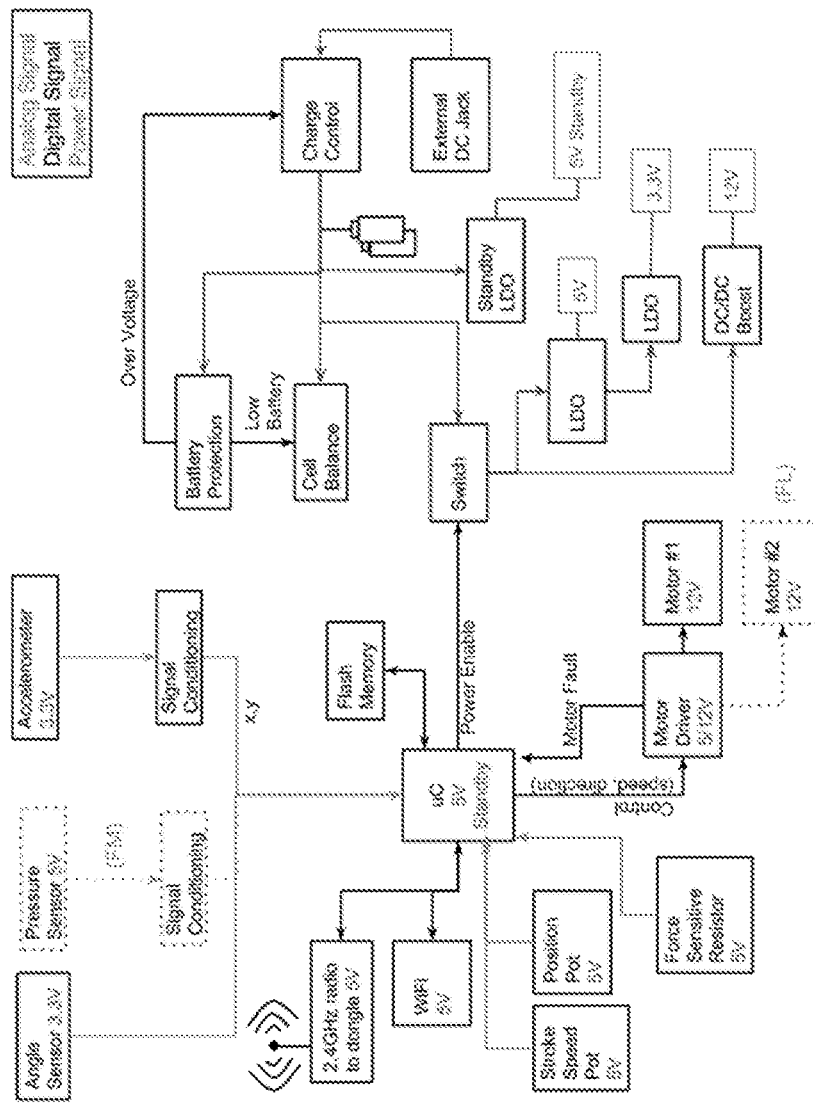
FIG. 15 shows how one interactive device's sensors signals may be sent and received for interacting with a second interactive device.

In the interactive mode, the paired interactive devices are able to receive and send signals detected from the various sensors contained within the interactive devices. A diagram of a possible communication scheme between the paired interactive devices are shown in FIG. 15. As FIG. 15 shows, the signals 1572 obtained by the sensors (e.g. angle sensor, pressure sensor, and accelerometer) of one interactive device are gathered and transmitted so that the corresponding interactive device may responding accordingly to the signals received from the sensor outputs.

Both male and female devices may be function using recorded or canned sessions. When a device is in the 'offline default' mode, the user will only be able to use a recorded or a canned session. Recorded sessions are sessions were recorded from a previous interactive session, while canned sessions are those that that have been pre-loaded onto the device. For both canned and recorded sessions, the entire loop will run within the used time interval and wait until continuing the next iteration. With a user interface, a user may record a current interactive or manual session for later use by having the device or audio dongle save the motor control set-points as they are received. The device or audio dongle will be preprogrammed to save the control set-points at a predetermined interval to later provide a realistic reproduction of the original session. In other words, a recorded session is a series of control set-points that are updated to the control loop at the same refresh interval that is used for an interactive session (approximately 10 Hz) which will exactly reproduce the prior experience.

Figure 16:
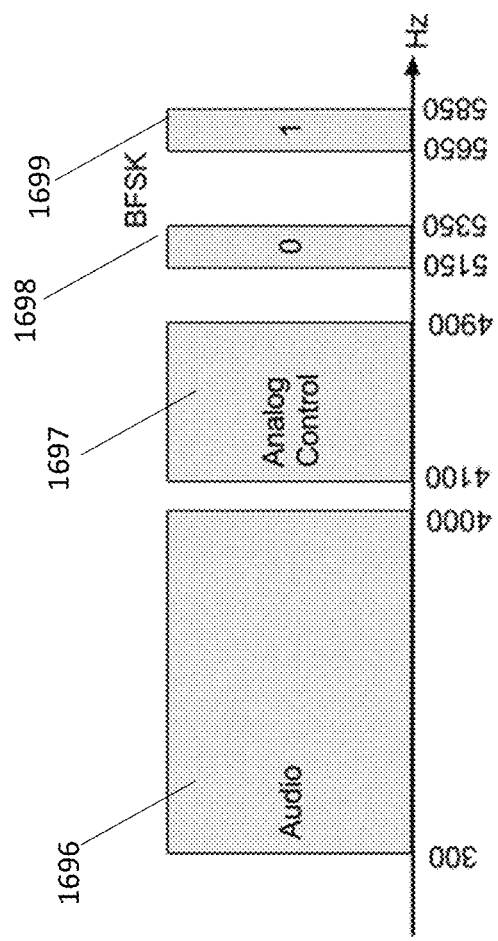
FIG. 16 shows the audio usage spectrum for the various signals.

The audio spectrum usage for the interactive devices occur over VOIP services may be supported in the following spectrum division: audio transmitting/receiving at 300-4000 Hz (1696), analog control transmitting/receiving at 4100-4900 Hz (1697), the BFSK 0 (space) transmitting/receiving at 5150-5350 Hz (1698), and the BFSK binary 1 (mark transmitting/receiving at 5650-5850 Hz (1699), (FIG. 16). Both the female and male device can have and be in a number of different modes. Having modes with different energy level consumption saves power. The interactive device may have an audio transmit mode, an audio receive mode, an idle mode, and a sleep mode. For the audio spectrum firmware, an interrupt driven architecture where the following tasks are enabled/disabled in ISRs and where "main ( )" only checks for flags may be used. This architecture would also be less taxing on resources and use less flash as well as allowing the microcontroller to sleep when there is nothing for it to do.

The interactive devices may have associated external interrupts. FM demodulation lock change detected (rising and falling edges); mark tone changes detected (rising and falling); space tone change detected (rising and falling); packet received from wireless link (falling); and low battery detected on power supply (falling).

The microcontroller manages a number of tasks as shown in Table 1. Table 1 shows all transmit and receive from the audio dongle's perspective to the audio jack. Each task will have a minimum initialization and run/update function. The peripherals will have open and close functions in their respective AOS, such that when not in use, the peripheral is disabled and power is conserved. In one configuration, all of the external interrupts are on the same GPIO port which allows for one interrupt handler to control execution. System ticks and time-based execution will be from the same timer, to have the same interrupt vector.

connection. Ethernet support can be accomplished with a dedicated Ethernet controller chip, an FPGA, or by using an RTOS with Ethernet stack in firmware. Application firmware would then parse the Ethernet packet payloads into session protocol messages and pass them through to and from the IID would using the radio. The Base Station will likely have to be powered from a power supply (wall wart or USB) due to the higher power needs. Because the control and authentication signals will be transferred over Ethernet, the Base Station is not used to use the audio interface for such purposes. There could then be two variants—one that obtains and plays audio using the audio jack (same HW interface as the audio dongle), and the other that uses the user to get audio directly from the PC, smartphone, or tablet.

Communication Protocol

Overall, when a device first wakes up, it searches for an Internet connection. If it finds an Internet connection, it operates in online mode and uses the Internet connection for

TABLE 1

Summary of Microcontroller Tasks

| Task | Priority 10 = high 1 = low | Description/Responsibility | Trigger Interrupt | Timer Interval | Task Finish |
|---|---|---|---|---|---|
| Radio Receive | 8 | Saves packet to buffer and enables either FM or BFSK handler | Radio IRQ | — | — |
| Radio Transmit | 9 | Writes to radio TX buffer either: verified BFSK packet to the radio control value and transmits. Blocks until any RX transactions complete | — | — | Control Value RX BFSK Shift In |
| BFSK Shift In (RX) | 5 | Assemble and verify binary packets found in audio | Mark/space state change | — | — |
| BFSK Shift Out (TX) | 3 | Encode raw packets from IID in BFSK forward over line-in to VOIP | — | — | Radio Receive |
| Control Value TX | 4 | Encodes a control value from IID to FM | — | — | Radio Receive |
| Control Value RX | 6 | If currently locked, samples the VCO input and calculates the current control value from VOIP | — | 50 ms | — |
| Control Value Update Interval | 7 | Restarts FM Update interval based on lock state change | Lock state change | — | — |
| Speaker volume | 1 | Increase or decrease value of gain for audio amp input signal, saves gain in flash | Up or down button | — | — |
| Modulation Update | 2 | Per enabled option for modulation output, reconfigures either: DAC update interval triangle timer interval function generator IC registers | — | — | Control Value TX — BFSK Shift Out |
| System Ticks | 10 | Keeps track of how many ticks have passed since reset (could also be persistent) | Timer overflow | 10 ms | — |
| Enter Bootloader | TBD in Phase 2 | Jump into bootloader execution for firmware update purposes | — | — | Radio Receive — BFSK Shift In (RX) |

In some examples, the audio dongle may have a physical connection for connecting to a network. In the scenario where WIFI is not used, a wired Ethernet connection to the internet is present, the dongle board can be modified to accept a standard Ethernet connecter for having a network authentication. If no Internet connection is found, it transitions to offline mode. In offline mode, the device is authenticated over audio only. In online and offline modes, the device receives control data over audio and can respond with its own control data back in the opposite direction. Communication from device to server, server to device, and device to device, is done through the Session Control Messaging Format.

The interactive devices need to be authenticated prior to use in the interactive mode. Each interactive device may have at least one unique encrypted key. In one example, every device is given two encryption keys. The first key is known by all devices like it and the server. This key is also known as the common key and is used for initial communication. This key should be kept a secret. The second key is a device specific key, randomly generated for each device that is used for authenticated communication. This key is linked to the device serial number and this information is stored in The Company's server. When a device connects to the server, it sends its serial number to the server. The server looks up the encryption key tied to this serial number and uses this encryption key to encrypt future messages. A device is authenticated when it is receiving messages encrypted using the unique encryption key specifically chosen for it at manufacturing.

The communications between the interactive devices will be secure. All messages to and from the server or device will be encrypted. In order to understand the first encrypted message from a device, the server desires to be using the same key to decrypt the message. Therefore, a common key may be used so that all initial communications is understood by the server. The use of a single common key alone may not be enough for good security because if an attacker discovers this key, all devices are compromised. Therefore, to add another layer of security, a device specific key is used so that even if the attacker obtains the common key, the attacker cannot compromise the device until the database containing the device specific keys is also compromised. Another layer of security is the Session ID. Every connection is associated with a Session ID. Because Session Control messages over audio can be recorded and played back, this Session ID prevents the device from accepting a session that has already occurred.

The most likely way the interactive devices will communicate with the Server is over a WIFI connection. Before the interactive devices can be used in an interactive mode, the device must be registered. An online device will immediately try to contact the authentication server and identify itself and register with the server 1780. It sends a Session Control message encrypted with a common key that only devices like it and the server knows 1781. The message contains its unique serial number chosen at the time of manufacturing 1782. The server has this information also and will use this information to encrypt future messages. The device is now authenticated and can be used normally (FIG. 17A)

An online device may attempt to communicate with an offline device over audio. An offline device will remain idle until it is authenticated over audio, after which it will operate normally, receiving and processing control data, and sending back its own control data. An online device will immediately try to contact the authentication server and identify itself.

It sends a Session Control message encrypted with a common key that only devices 1700, 1740 like it and the server 1771 knows. The message contains its unique serial number 1782 chosen at the time of manufacturing. The server 1771 has this information also and will use this information to encrypt future messages. The device is now authenticated and can be used normally. When a session is started and the online device desires to authenticate the offline device, the server sends the offline device's information to the connected device. The connected device uses this information to authenticate the offline device (FIG. 17B).

In places where Wi-Fi is not available, the user can log onto a website 1771 that can authenticate the device 1700, 1740 (FIG. 17C). The web service provided by this website can send authentication messages 1774 through audio. The device may have a way to indicate to the user that it has correctly received an authentication message. The user may now use the device. The device may operate in this mode for some time and additional authentication from the web service may be desired to extend usage time.

Certain messaging protocols will also be included. The endianness and byte alignment of the data payloads will be that of the microcontroller used for the interactive devices. The interactive device and audio dongle will use the same protocol for radio communication, BFSK, and Wi-Fi communication. Devices should not waste time and power decrypting every message they ever receive to determine if it was the recipient. The header (version, message type, and serial number) is not required to be part of a CRC because a specific value is used. The probability that a false positive occurs for the unencrypted section is $(1/2^8)*(1/2^{32})=1$ in 1,099,511,627,776 messages.

This format allows devices to parse messages in the following sequence:
Version+message Type byte:
 A. On lower levels of the devices, power can be saved by ignoring messages that do not start with a good value, used as a synchronization byte
Serial Number:
 A. This is common knowledge, and does not increase security to be encrypted
 B. If matches this device's serial number or that of an assisted unit, then decrypt
 C. Addressing being in the message format allows the system to be scalable
Encrypted Data
 A. Control set-points are not encrypted (only unencrypted message)
 B. Once decrypted, data fidelity is verified with the CRC
 C. For assisted sessions, it is better to have the online device do the encryption to reduce the throughput of the audio connection, which will have slower baud rate The version column exists to provide some mechanism for the Session Control Messaging Format to change in the future if desired. This is useful when new columns are added because features were added. The server and firmware will use this version value to support updates and changes in message formats.

Session ID: The session ID of the current session. If the device is interrogated while not currently in a session, this will be zero.

Message Type: Each message has a message type. The message type defines the purpose of the message, what action the device may take, and how to interpret the data payload.

Serial Number: This is included to conceptually allow for addressing, and is include before the session ID and the encrypted portion of the message to avoid unnecessary processing of messages.

Session Types

There are three session types: one-to-one, one-to-many, and pre-recorded. In each type, there is a performer device (master) controlling one or more user devices (slaves). A performer and user device may have the same hardware, but before a session start, one device is designated a performer device, and one a user device. In a pre-recorded session, a pre-recorded stream can be thought of as a recording of a performing device.

Figure 18:
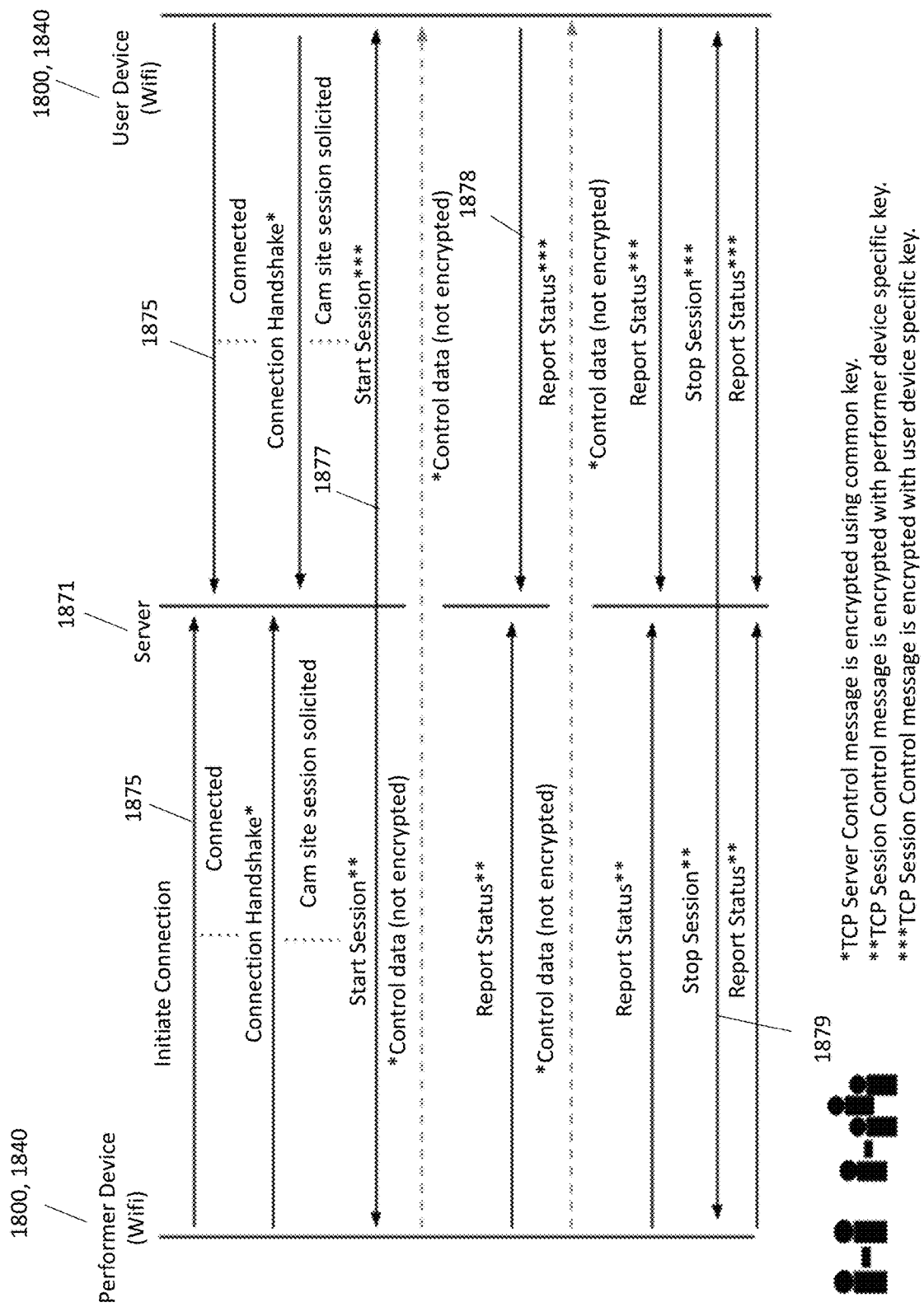
FIG. 18 is a diagram of simplex communication with devices online.

A first type of session is labeled as simplex communication and diagramed in FIG. 18. Simplex communication is a one way transmission of the performer's control data. Here, a server 1871 sends a signal to both interactive devices 1800, 1840 to start 1878 and to stop 1879 a session. Both interactive devices 1800, 1840 will start working until one disconnects or a third party informs the server that the session is over by reporting its status 1878. In this scenario, the interactive device 1800, 1840 will not send its control data. A user device uses the performer's control data for movement information. In this mode, the user device cannot send control data to the performer's device. A simplex communication scheme is typically used when the user device cannot send data to the performer device. This may be because of a limitation in a VOIP protocol, a performer choosing to mute his/her microphone, or because a use case may naturally use a simplex communication. One-to-many and pre-recorded sessions use simplex communication.

Figure 19A:
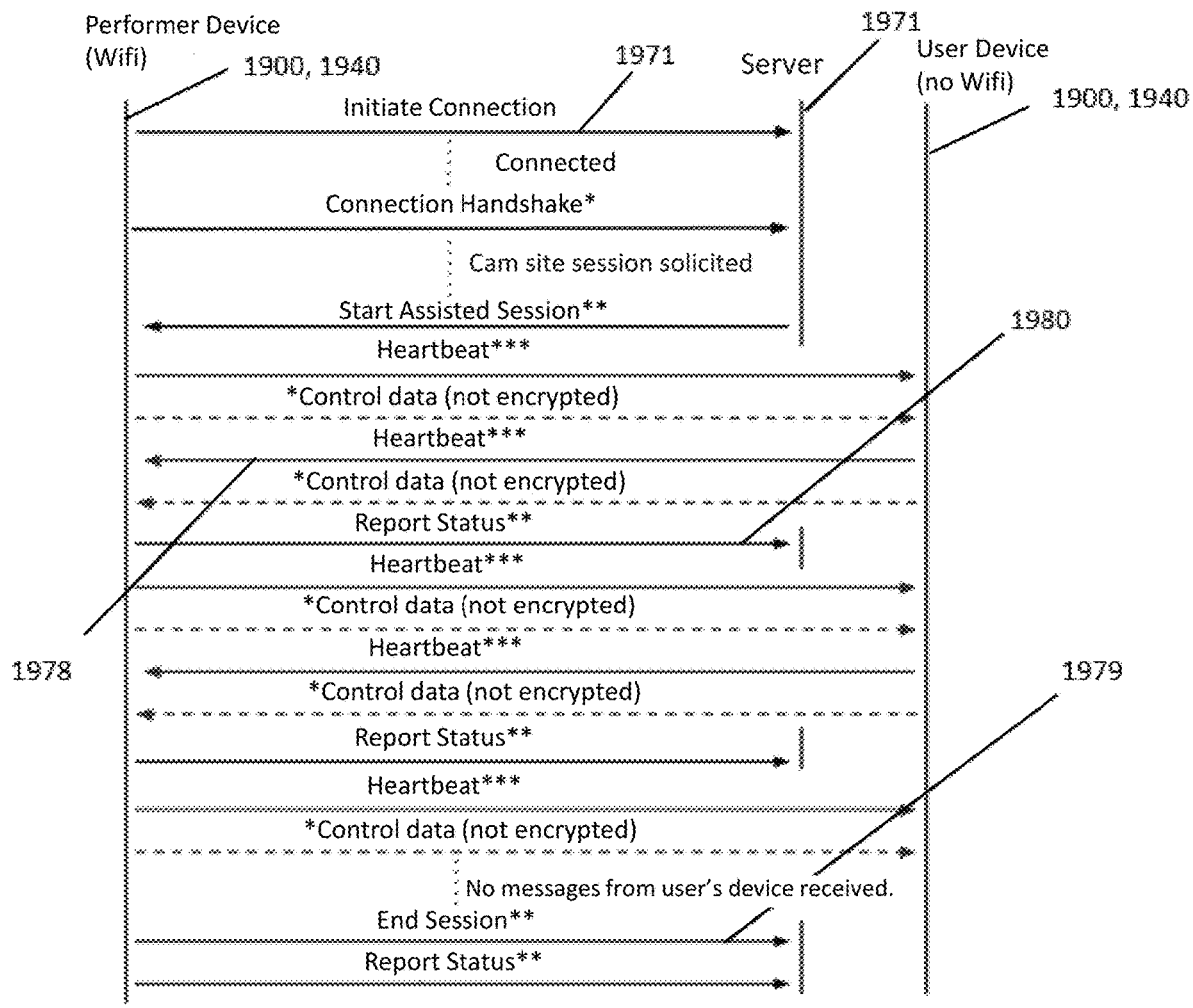
FIG. 19A is a diagram showing duplex communication with authentication assist from the performer's (already authenticated and registered) device.
Figure 19B:
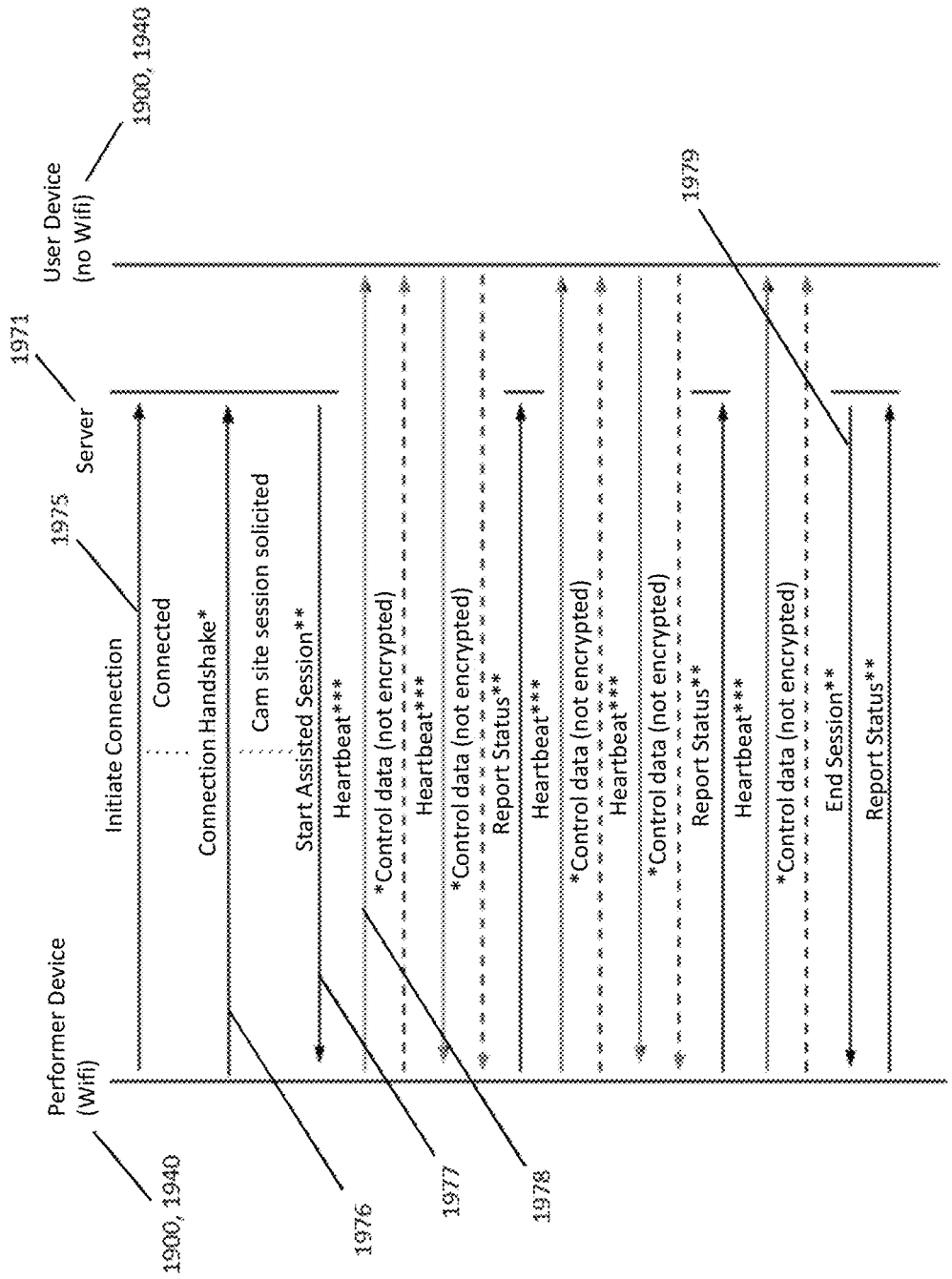
FIG. 19B is a diagram showing duplex communication with authentication from the performer's (already authenticated and registered) device where the user sends stop session signal.

A second type of session is labeled duplex communication is shown in FIGS. 19A and 19B. In this scenario, the performer's device 1900, 1940 will send authenticating signals until the user's device no longer responds. At that point, the performer's device will stop sending authenticated signals 1978 and report 1980 to the Server 1971 that the session 1979 has ended. In both monogamous sessions and two users conducting a peer-to-peer session using a Third Party site, the duplex communication scheme allows one user device to send control data back to the user's/performer's device. In other instances the two parties may be user of the interactive device interacting through the Service Provider or other Third Party site. This mode allows the user device to give feedback to the performer's device. There may also be a duplex-assisted session. In this type of session, the performer's device is online and can receive communication from the server through a Wi-Fi connection. The user's device is offline and not connected to a Wi-Fi connection. When the user solicits a session, the server is given some information about the two devices that are to be connected. The server performs a check to see if the devices are online. It detects that the performer's device is online and connected to Wi-Fi but the user's device is not. The server knows that this is an allowed use case and it sends a Start Authentication Assisted Session message to the performer's device. The performer's device uses this information to encrypt Heartbeat messages to allow the user's device to accept the control data.

From the perspective of the user's device, the control data may be present, but user's device cannot use it until it receives valid authenticating messages from the performer's device. For extra security, the performer's device does not send control data until told by the server. The user does not mute his/her sound so there are messages coming back from the user's device. The user's device responds to the authenticated messages with its own authenticated messages. The session can discontinue in three ways: when the user's device stop responding (see FIG. 19A), when the server is informed by a third party that the session has ended (see FIG. 19B), or when the performer's device loses the connection to the server. When a session ends, the performer sends a final status report indicating that the session has ended if it is still connected. If that message fails to send, the device will store the session into non-volatile memory and attempt to retransmit at the next chance it connects to the server. All assisted sessions use that The Company's server knows the serial numbers of the participants, and that those numbers are given to the online device at session start. It is the responsibility of the online device to send the Session Report.

Figure 20:
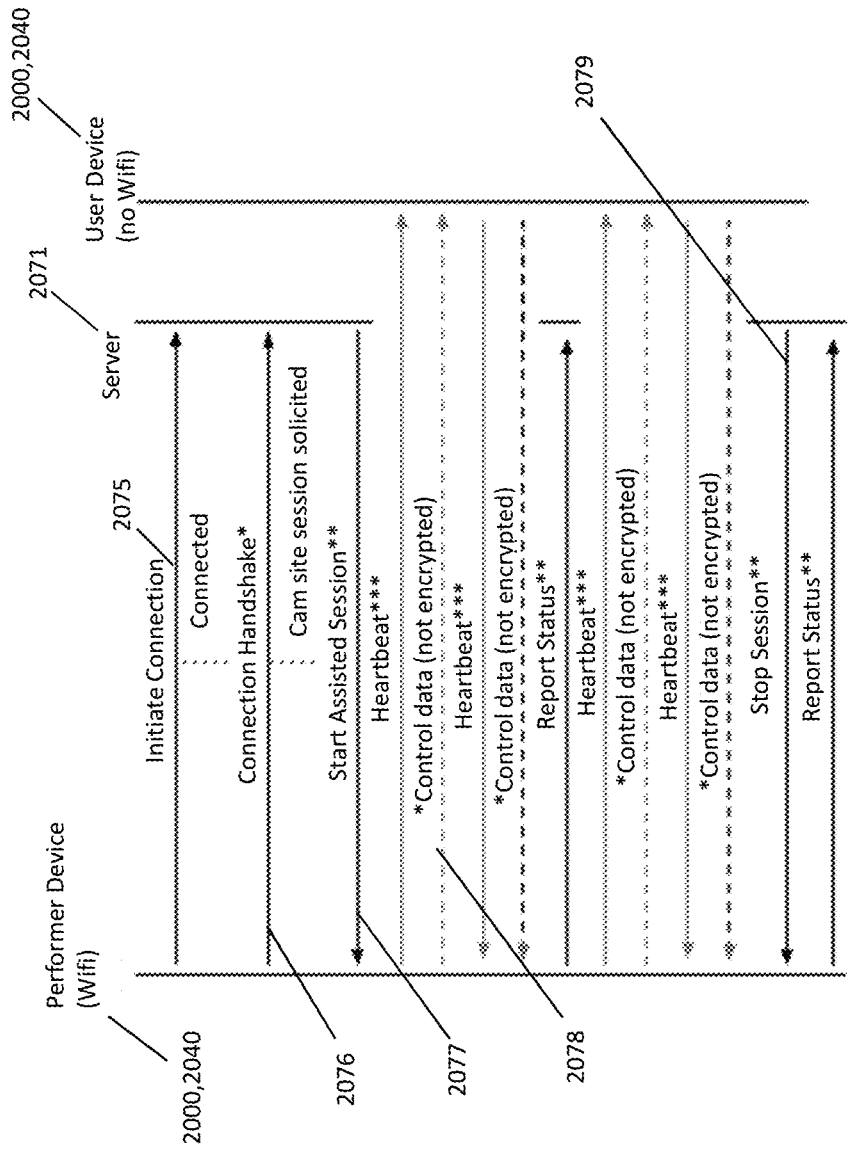
FIG. 20 is a diagram showing simplex communication with authentication assist from the performer's (already authenticated and registered) device.

Another type of session is labeled a simplex assisted session and is diagramed in FIG. 20. The performer's device 2000, 2040 is online and can receive communication from the server 2071 through a Wi-Fi connection. The user's device 2000, 2040 is offline and not connected to a Wi-Fi connection or Base Station. When the user solicits a session 2075, the server is given some information about the two devices that are to be connected. The server performs a check to see if the devices are online. It detects that the performer's device is online and connected to Wi-Fi but the user's device is not. The server knows that this is an allowed use case and it sends a Start Assisted Session 2077 message to the performer's device. The performer's device uses this information to encrypt authenticated messages to allow the user's device to accept the control data 2078. For extra security, the performer's device does not send control data until told by the server 2071. The user mutes his/her sound so there are no messages coming from the user's device. The session ends 2079 when the server is informed by a third party that the session has ended or when the performer's device loses the connection to the server. In all assisted sessions use, the Company's server knows the serial numbers of the participants, and that those numbers are given to the online device at session start. It is the responsibility of the online device to send the Session Report.

Figure 21:
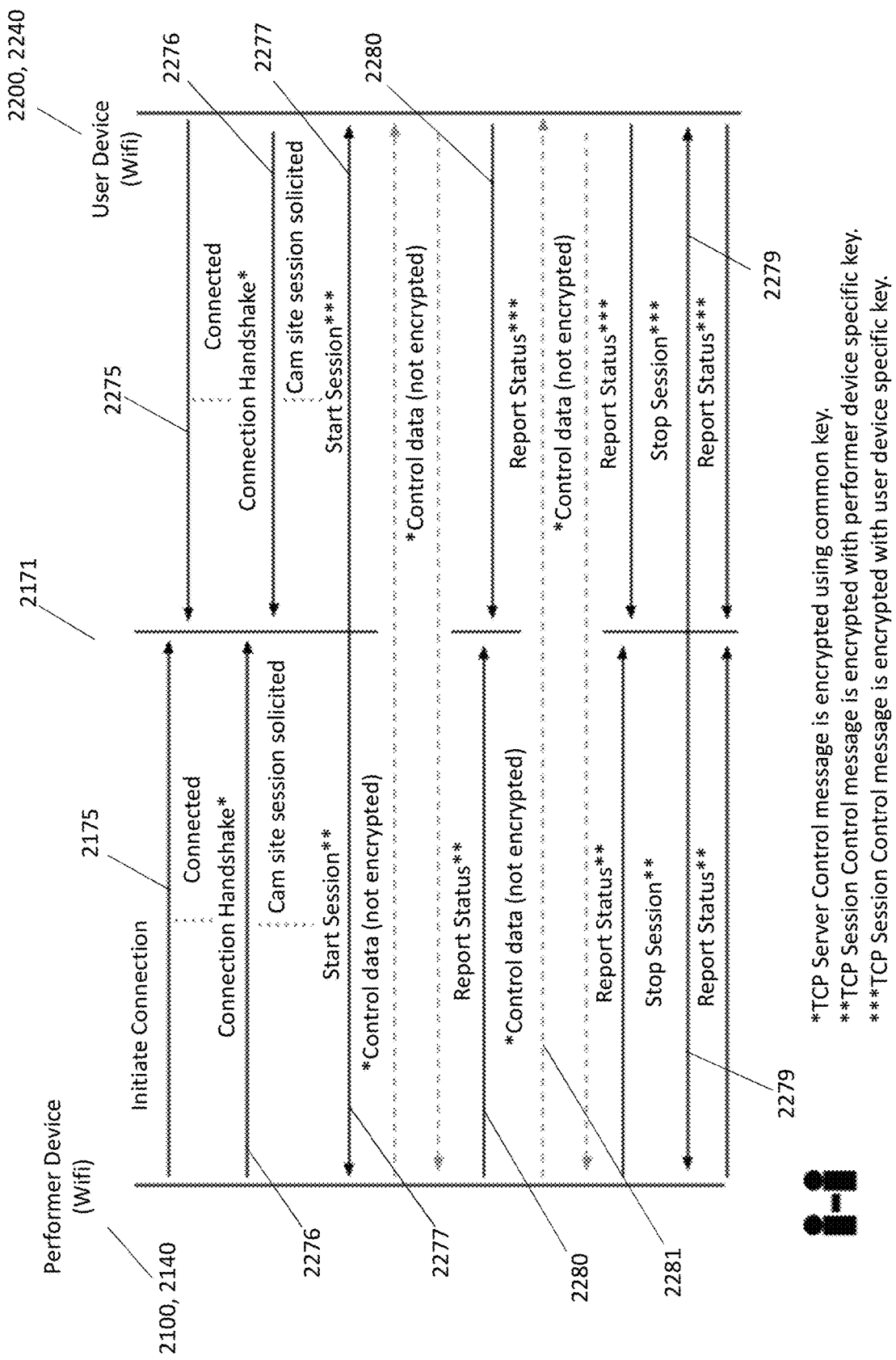
FIG. 21 is a diagram showing duplex communication with both devices online.

A duplex online session is another available session option and is diagramed in FIG. 21. In this type of session, the performer's device 2100, 2140 is online and can receive communication from the server 2171 through a Wi-Fi connection. The user's device 2100, 2140 is also online and connected to a Wi-Fi connection. When the user solicits a session 2175, the server is given some information about the two devices that are to be connected 2276. The server performs a check to see if the devices are online. If it detects that the both the performer and user's device is online and connected to Wi-Fi, the server 2171 sends a Start Session 2277 message to both devices. The performer's device begins sending control data and optionally, report the status 2280 of the session. At the same time, the user's device will start accepting the control data, and report the session status to the server. The performer's device stops sending control data after it receives the Stop Session message from the server. It may also send one final Report Status 2280 message after the session ends. The user's device will also stop accepting control data after it receives the Stop Session 2279 message and send the final status report. The session will end if either devices are disconnected from the server or if the server is informed by a third party that the session has ended.

Yet another type of session that will be available is a simplex online session. The performer's device is online and can receive communication from the server through a Wi-Fi connection. The user's device is also online and connected to a Wi-Fi connection. When the user solicits a session, the server is given some information about the two devices that are to be connected. The server performs a check to see if the devices are online. It detects that the both the performer and user's device is online and connected to Wi-Fi. The server sends a Start Session message to both devices. The performer's device begins sending control data and optionally, report the status of the session. At the same time, the user's device will start accepting the control data, and report the session status to the server. The performer's device stops sending control data after it receives the Stop Session message from the server. It may also send one final Report Status message after the session ends. The user's device will also stop accepting control data after it receives the Stop Session message and send the final status report. The session will end if either devices are disconnected from the server or if the server is informed by a third party that the session has ended.

Figure 22A:
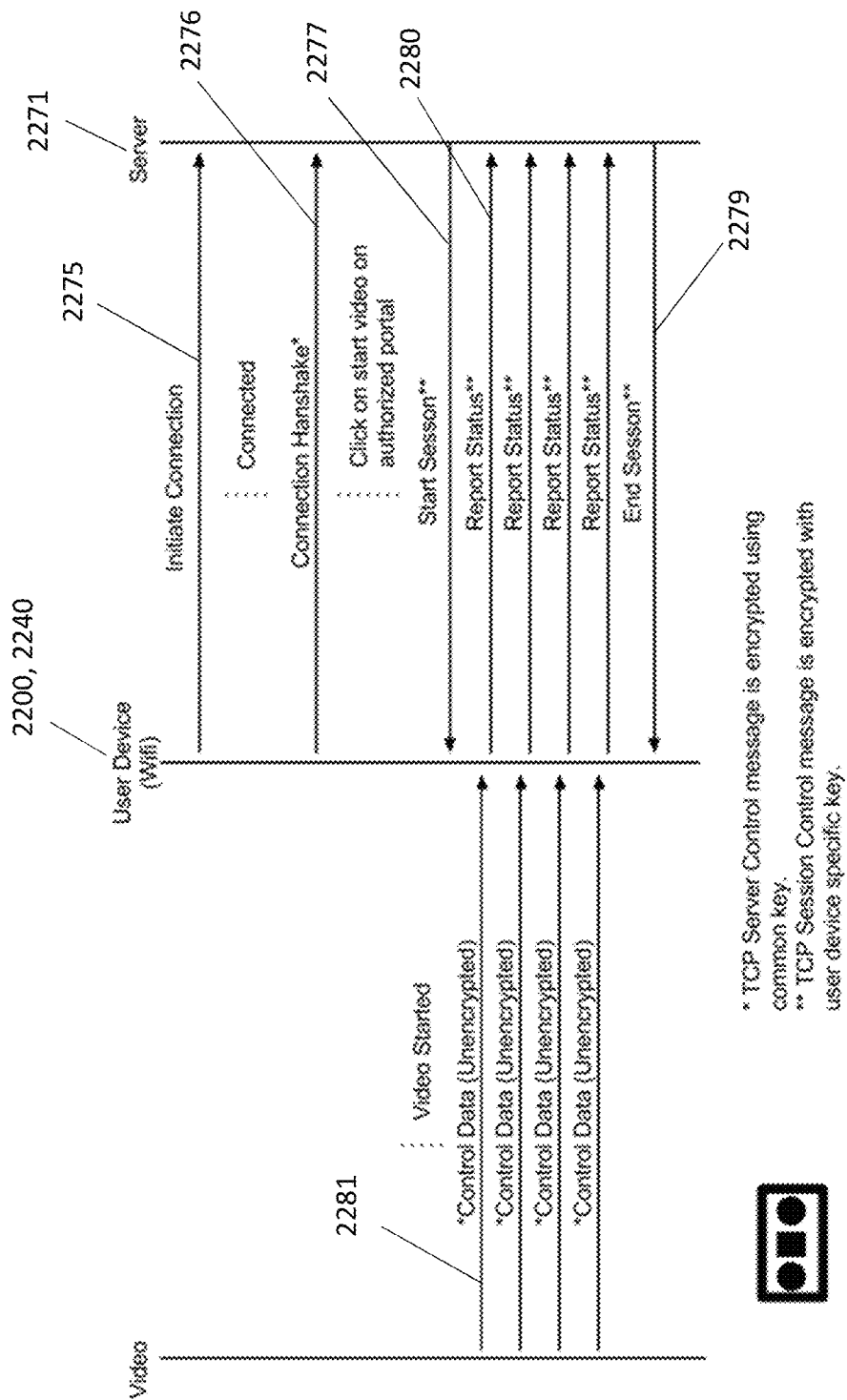
FIG. 22A is a diagram showing the user using a prerecorded session.
Figure 22B:
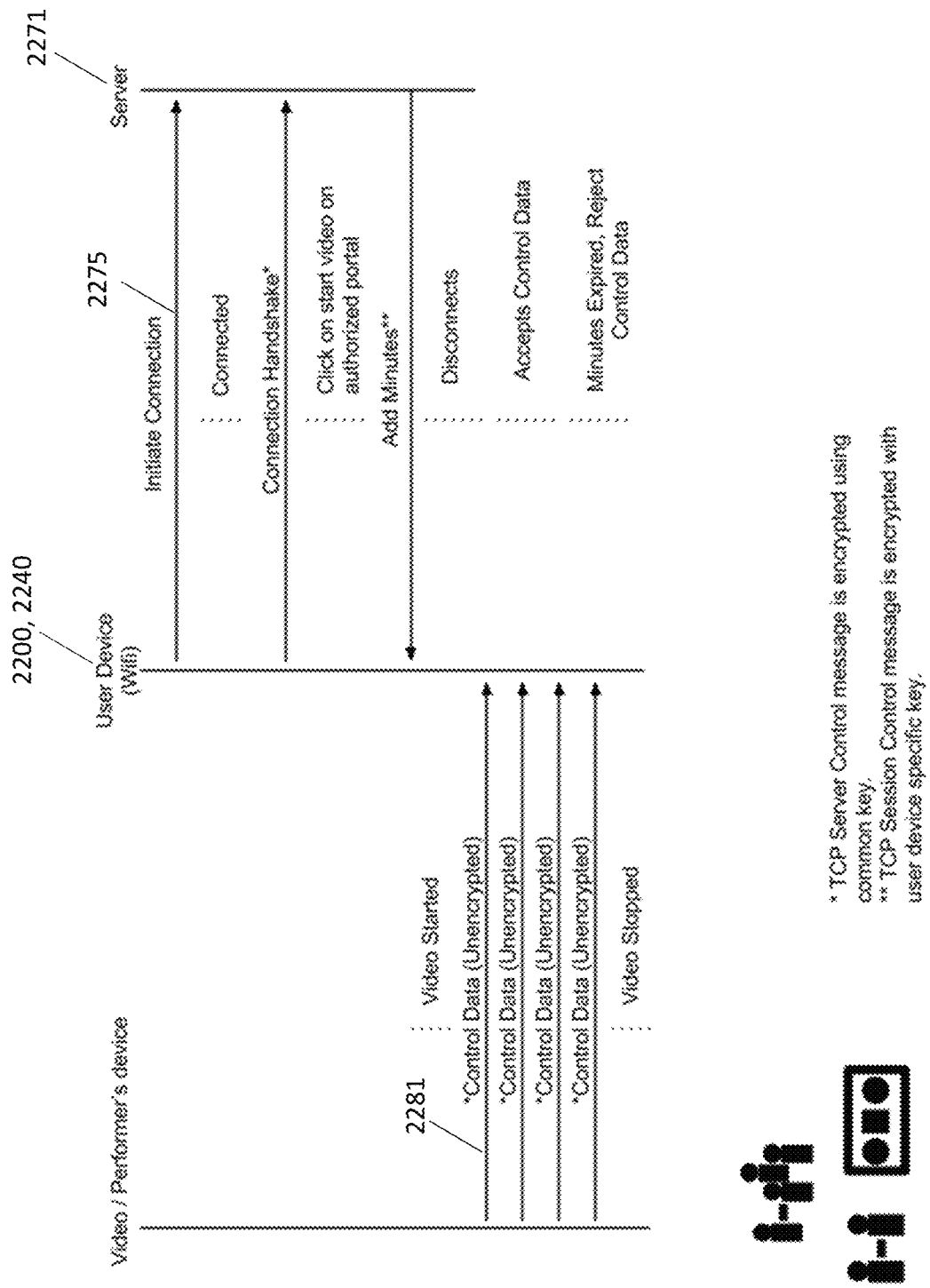
FIG. 22B is a diagram showing the user using a prerecorded session where the user may purchase and add minutes to the session.

Finally, a user may run a pre-recorded online session. Diagrams of pre-recorded sessions are shown in FIGS. 22A and 22B. The user uses an authorized distributor portal to stream pre-recorded contents 2281 online. The user clicks on a button to start streaming a pre-recorded video. The authorized distributor notifies The Company's server 2271 that a stream is starting and The Company's server 2271 will update the device's 2200, 2240 allowed content table. The device 2200, 2240 can also report that it has rights to always use the online content to the authorized distributor's server and allow itself to receive the control values while the video streams. Otherwise, the server 2271 will then send a Start Session message 2277. The device periodically send status reports 2280 to the server 2271. The server 2271 has some information on how long the stream is going to be and it stops the session when that time has expired, or when it is notified by the authorized distributor that the user has stop the video stream 2279.

A user can prepay for usage. To add prepaid minutes to the device, the user uses a web service from an authoritative source. This authoritative source triggers the server to send an Add Minutes message to add minutes to the device. The device may accept control data from any source as long as time has not been exhausted. When time has expired, the device rejects all control data.

Figure 36:
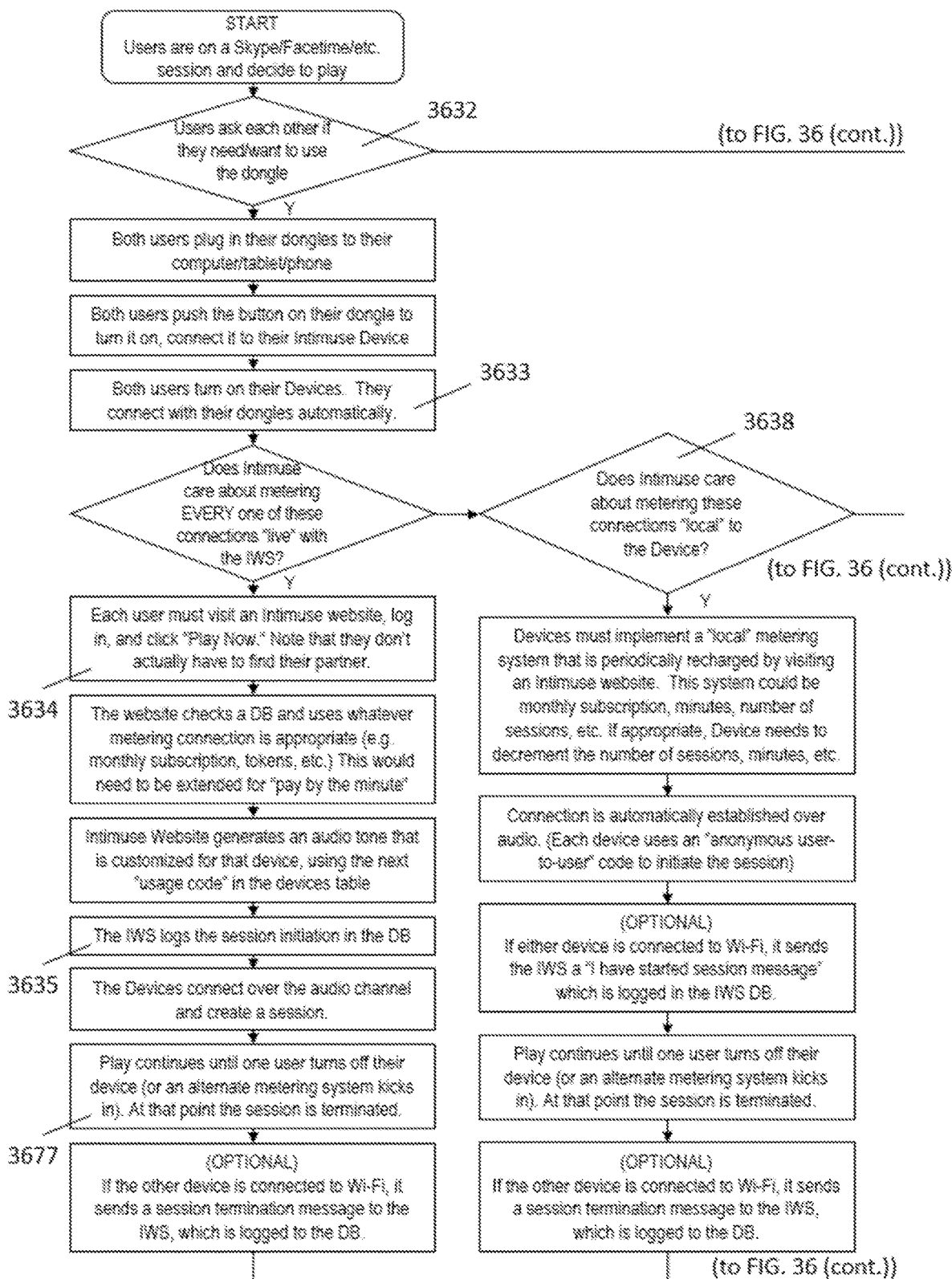
FIG. 36. is a flowchart showing two users conducting a peer-to-peer session using third party video.
Figure 36:
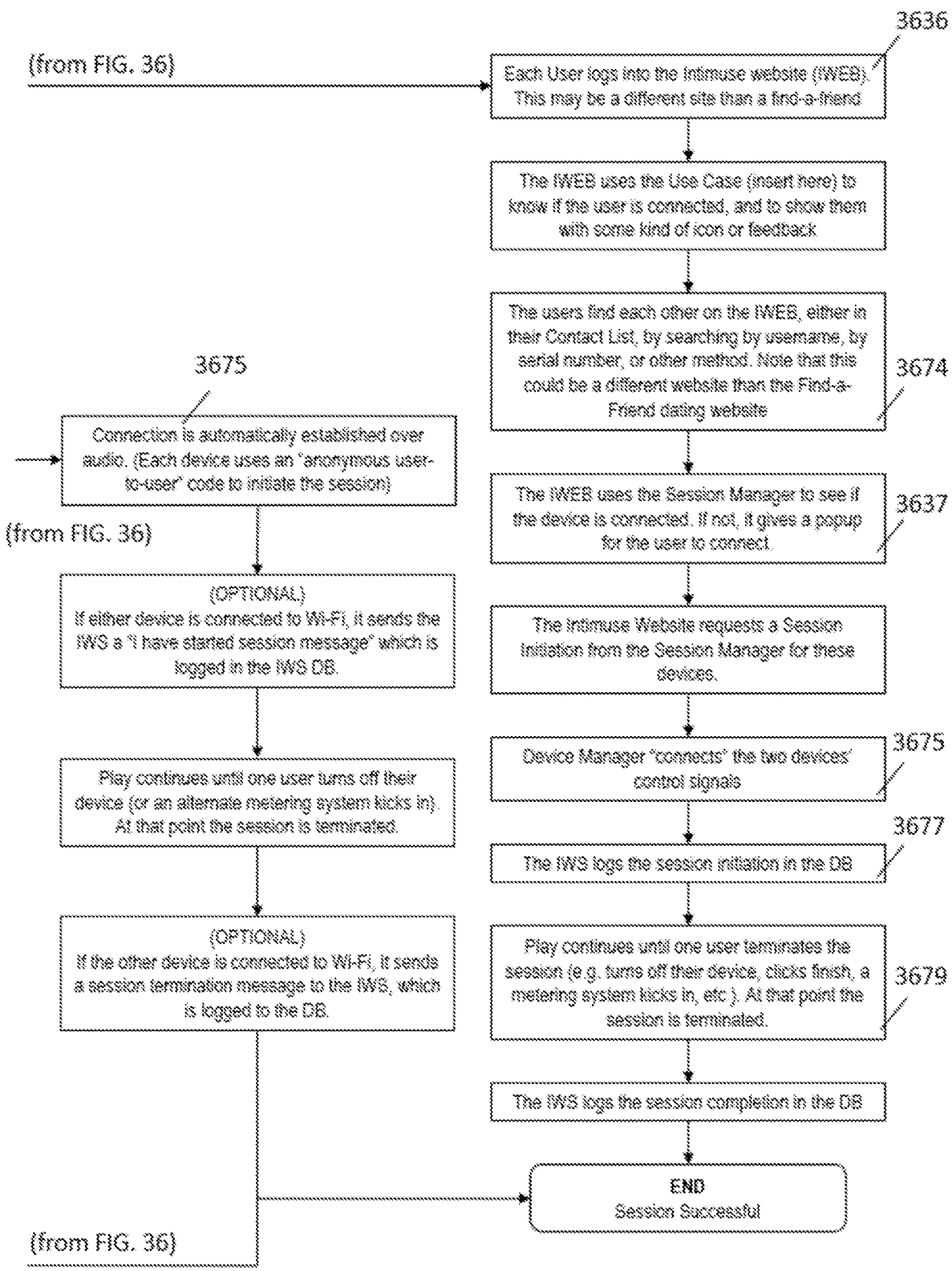

FIG. 36 shows a flowchart of two users engaged in a peer-to-peer session using third party video service. The users may connect through a dongle 3632 or through a Company website 3636. The users may find each other through the Company website 3674. Session manager may then see if the devices are connected 3637. The session manager may connect the two interactive devices 3675. The Company website may provide means for initiating a session 3677. The session ends 3679 when one device disconnects.

Staying with FIG. 36, if the users use a dongle for interacting, the connection may be automatic and each device uses an "anonymous use-to-user code to initiate a session 3675. The Company website may meter connections such as providing subscriptions, pay per minute, tokens and so forth 3634. The Company website may generate audio tones that is customized for the device. The Company website may log the session initiation in their Company database 3635. Devices connected over audio may initiate a session 3677 once their serial numbers are validated and are able to interact until one device disconnects and terminates from the session.

Service Provider Web Software (SPWS)

Figure 23:
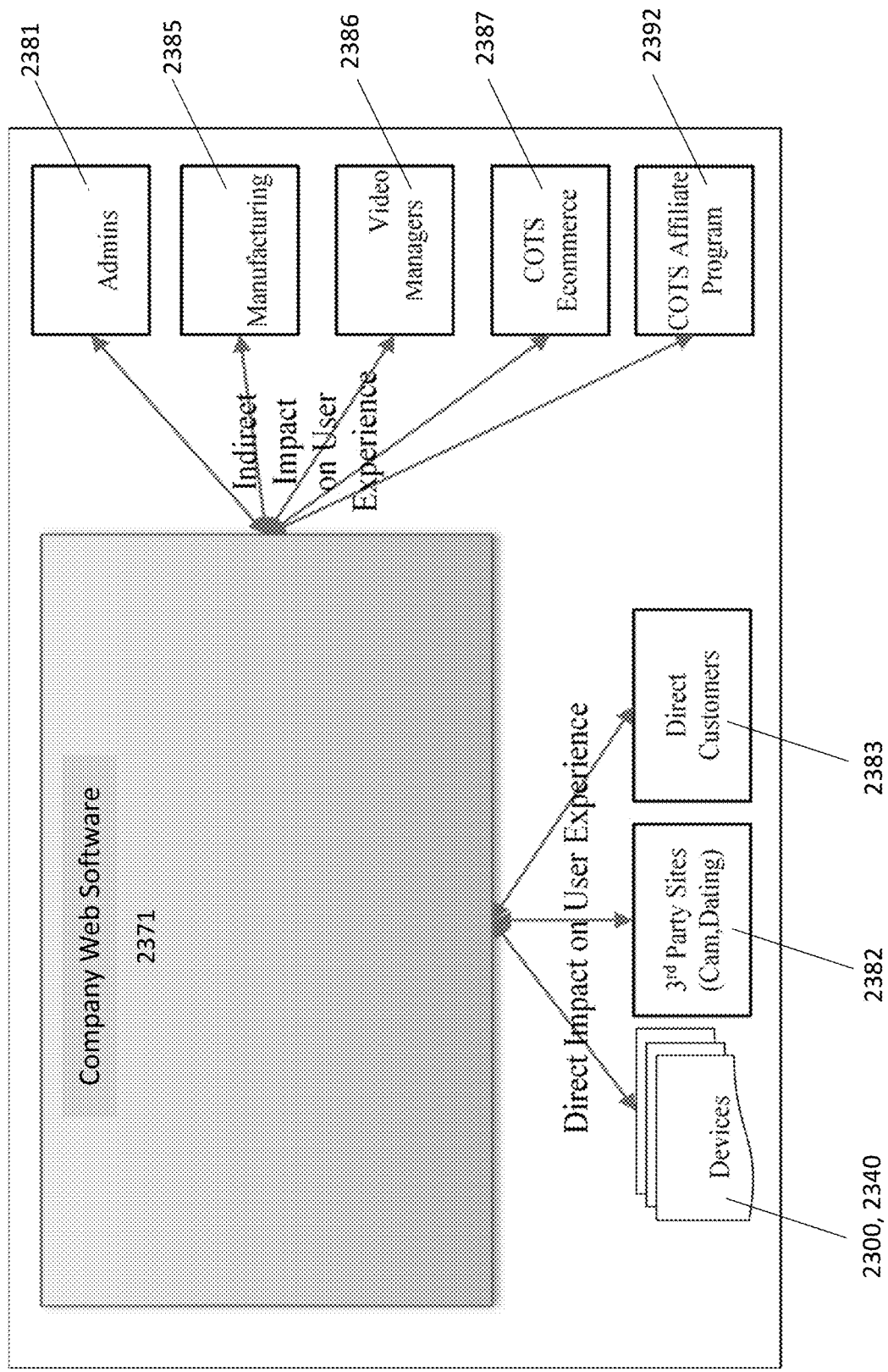
FIG. 23 is a block diagram showing the high level components of a service provider's web software.
Figure 24:
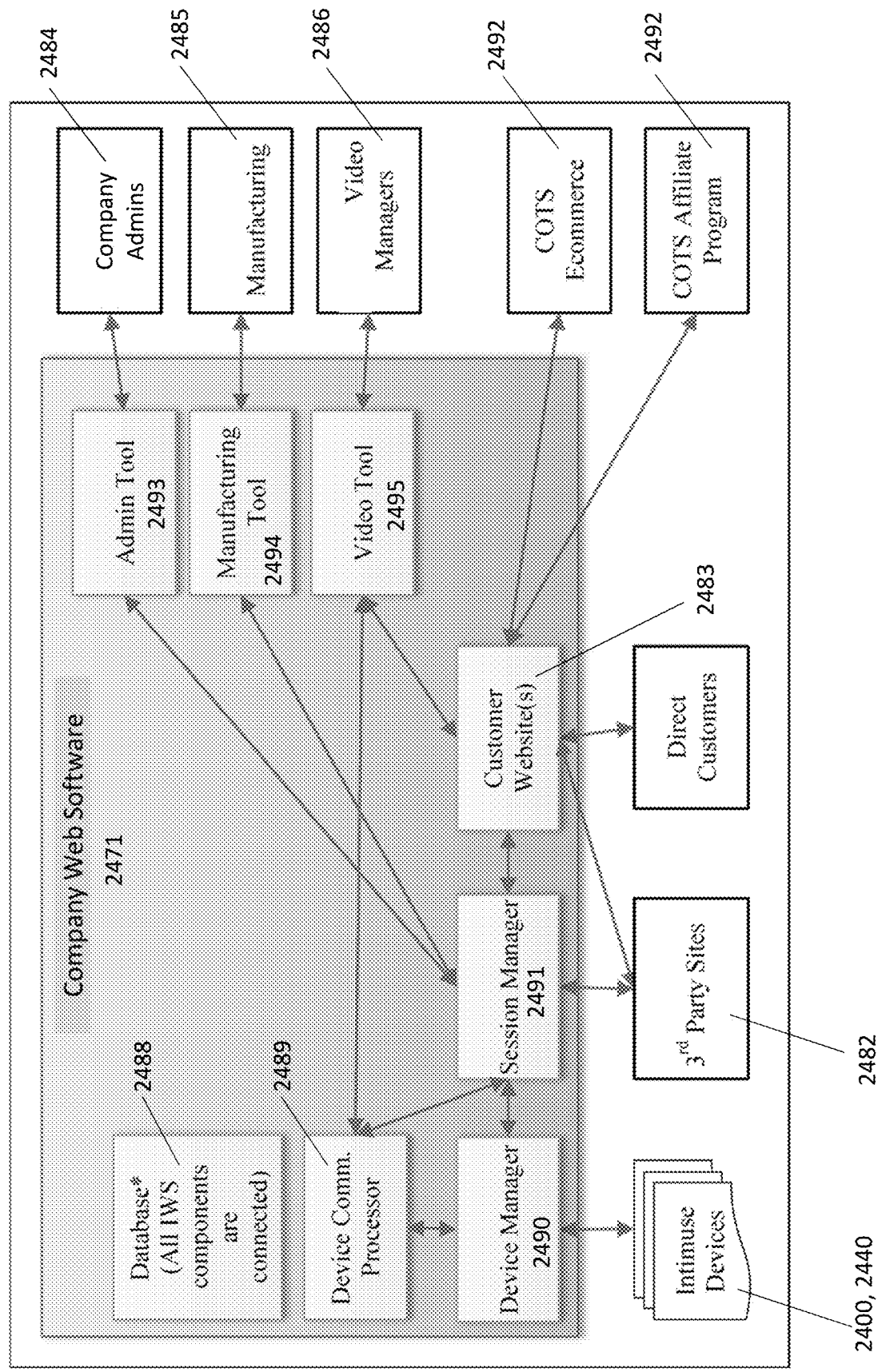
FIG. 24 is a block diagram showing the service provider's web software internal and external components.

FIG. 23 shows the SPWS using a high-level, "black-box" diagram to outline the external users and systems that the IWS is intended to integrate with. These have been divided into two general categories: "Direct Impact on User Experience" and "Indirect Impact on User Experience." The Company Web Software 2471 is in communication with the interactive devices 2300, 2340 and as well as third party sites 2382 and direct sites that are used by customers 2383. Company server through its web software 2371 is in connection with the company admins 2381, company manufacturing components 2385, video managers 2386, COTS eCommerce components 2387, and COTS affiliated programs 2392. The SPWS can be divided into numerous functional blocks based on the nature of what each block is doing as shown in FIG. 24. The Company server 2471 includes: database 2488, device communication 2489, device manager 2490, session manager 2491, components for communicating with customer websites 2483. The server 2471 also includes administrative tools 2493 in connection with the session manager 2491 and in communication with manufacturing tools 2494. There are also video tools 2495 for interacting with the customer websites 2483. Company software and server 2471 are connected to the company admins 2484, manufacturing components 2485, video managers 2486, COTS eCommerce 2492, and COTS affiliated program 2492.

There may be external components associated with the SPWS. The Company's Devices are the physical devices of The Company's System. The Company's Devices currently consist of male toys and female toys, but may also include other devices that aid in bringing sexual pleasure. Over time, various versions of The Company's Devices may use SPWS support at any given time. "Third Party Sites" are external websites that will provide the ability to experience The Company's teledildonic sex within their own branded ecosystem. Third Party Sites may include Cam Sites, Dating Sites, and others. Third Party Sites will use "behind the scenes" integration with the SPWS. Users may be able to purchase The Company's Devices directly from the Third Party Sites. It is expected that integration with each Third Party Site may use a customized interface to the SPWS. Direct Customers may interact with the SPWS if The Company's deploys one or more Customer Facing Websites. These websites could enable Direct Customers to register their devices, to go on virtual dates, or to watch pre-recorded content. The Company's Admins are responsible for administration duties with SPWS, such as creating/deleting vendor accounts/SKUs, monitoring the system, and producing usage reports. The Company's Manufacturing Personnel are responsible for assembling, configuring, and testing The Company's Devices. The Company's Video Managers edit video content to contain the control signals necessary to synchronize The Company's Device activity with pre-recorded content. The COTS Ecommerce platform would be used by the SPWS to process payment from Direct Customers for monthly subscriptions or other such activity. A COTS Affiliate Program would be used by the SPWS for integrating with FLI's automated order-fulfillment process.

SPWS General Systems Requirements

In general, commercial off-the-shelf (COTS) solutions are favorable over custom solutions. In general, COTS solutions should be investigated prior to implementing custom solutions. When a COTS solution exists for an SPWS component, it should be pursued. If it is not pursued, the reasons should be documented. Best practices with regards to security should be identified and used. This includes interfaces between the SPWS and the "outside world" (e.g. The Company's Devices, Third Parties, Customers), as well as internally. Appropriate procedures may be established for ensuring servers' operating systems and software components are up to date. Scalability should be considered from the beginning. The initial release of the system should be designed as simple as possible to meet anticipated loads over an initial adoption period (e.g. one or two years), with a scale up plan in place prior to executing that initial release. State-less server software architecture should be pursued whenever appropriate. This approach facilitates scalability and disaster recovery. Backup & Disaster Recovery should be implemented from the beginning and should be automatic. A plan should be developed that determines how The Company's will handle such an event internally and externally. Specifically, how Third parties will be notified, how The Company's will handle charging for any sessions that were active when the problem happened (e.g. will The Company's not charge the Third party for interrupted sessions), and such things.

A "microservices" approach to system design should be used. The modules outlined in the Block Diagram and described in this document represent a high level view of the system architecture. Each module in the Block Diagram should further consist of modules based on functionality. If functionality is found to be shared across multiple modules in the Block Diagram, a new, high-level module should be created. Multiple modules should not implement the same functionality.

Wherever feasible, the SPWS should use test driven development practices to help improve the correctness of the code. The SPWS may be able to show proper operation under simulated loads. As such, the ability to simulate connections and disconnections from many devices may be implemented. System performance characteristics may be defined beforehand (e.g. latency to initiate a session, control signal throughput, Device Manager server CPU load, timing for creating new account, etc.). A plan for "going live" may be in place and tested against prior to first customer release. This may include complete functional testing, load testing, and testing with potential users unfamiliar with the system to ensure that failure modes not obvious to the developers are discovered and fixed prior to customer interaction.

The SPWS may be built on a cloud computing platform. For example, Amazon Web Services (AWS), MS Azure, or similar platform should be used. The cloud computing platform should have the ability to scale vertically and horizontally. The cloud computing platform should have availability levels acceptable to The Company's platform requirements. Ease of use of the development platform, feature set immediately needed, feature set envisioned for the future, and cost will be driving factors in the selection of an appropriate cloud computing platform.

Device Manager

Figure 25:
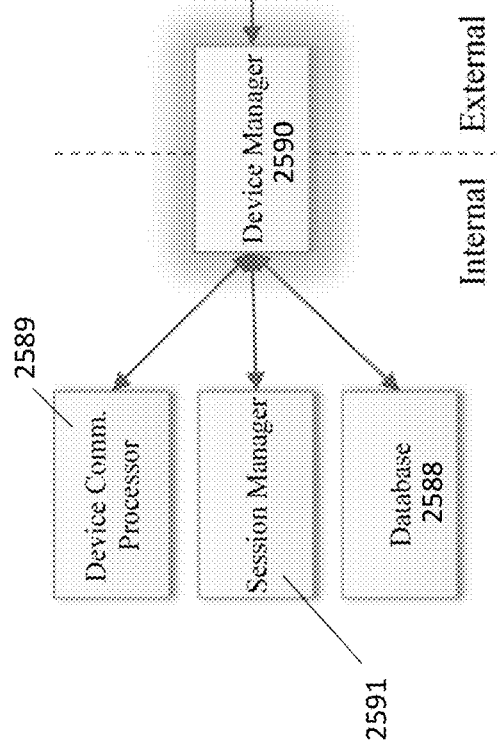
FIG. 25 is a block diagram showing how a device manager interacts with other internal and external components.

The Device Manager 2590 is responsible for creating and maintaining secure connections between The Company's Devices 2500, 2540 and the SPWS as shown in FIG. 25. The Device Manager 2590 may utilize the interface provided by The Company's Devices. The Device Manager may utilize the interface provided by a Database 2588. The Device Manager may utilize the interface provided by the Device Communication Processor 2589. The Device Manager may provide an interface for the Session Manager 2591. The Device Manager 2590 may provide an interface for The Company's Devices 2500, 2540.

The Device Manager 2590 is able to maintain connections with individual Company's devices 2500, 2540. The Device Manager 2590 may implement industry standard methods for allowing device-initiated M2M connectivity between each device and the Device Manager 2590. The devices should rely on DNS, and should use SSL connections or similar. The Device Manager 2590 may accept connection requests from The Company's Devices 2500, 2540, and may verify the requests against device-specific information located in the database (e.g. serial number and private encryption key). The verification prevents spoofed devices from causing problems. The Device Manager 2590 may be designed in such a way to handle the projected number of connections for the first two years of system release. The Device Manager 2590 may also use structural changes to handle higher loads. This may include load balancers, ability to redirect traffic to multiple instances of the Device Manager 2590, etc. The Device Manager 2590 may be able to handle reconnections from devices in the middle of a session.

The Device Manager 2590 has the ability to create Sessions between two or more of the Company's devices. A Session is the time when one or more ID's are connected to each other, to live streaming control commands, to pre-recorded content, or to admin-type content (e.g. firmware upgrade). A Session consists of: 1) devices being online in some manner (handled by Device Manager), 2) a request to connect the devices (Handled by SC), 3) a check that this connection is allowed, paid for, etc. (Session Manager 2591). The Device Manager 2590 may be able to create one-to-one, one-to-many, and prerecorded sessions between Interactive Devices as well as the Device Comm Processor 2589. It will likely do this by spawning a thread for each session, and will take in control data from each device, process it as necessary, and send along to the intended destination. The Device Manager 2590 may not transmit "private" information between users, or may use information to be exchanged between users (e.g. plain text serial numbers, usernames, etc.) except to facilitate an Assisted Session where an offline device shares the online device's Internet connection. The Device Manager 2590 may be able to terminate any session, thereby breaking the connection between The Company's Devices via the messaging protocol defined in this specification. The Device Manager 2590 may log all session events (e.g. initiation, termination, idle, etc.) to the System Database. The Device Manager 2590 does not desire to log actual session activity (e.g. control signals). The Device Manager 2590 may identify "idle" situations during a session and automatically terminate the session. All functionality related to enabling/disabling The Company's Device activity may be encrypted, per the messaging protocol defined in this specification. The Device Manager 2590 and The Company's Devices may implement a system that would prevent recording of the traffic to The Company's Device and playback. One method to do this would be to have the Device Manager send a start session command with a Session ID to The Company's Device, and The Company's Device would check a table of previously used Session IDs and would only use this Session ID if it was unique. Alternatively, the IWS might maintain a table of unique "usage keys" that have also been programmed to the device during manufacture. The IWS could then use the next "usage key" as a key in the control messages. Regardless, these IDs could be contained in every control packet, or periodically sent (e.g. every 1 minute). Furthermore, if a "shared table" approach is used, the IWS and Device could advance "usage keys" after a certain amount of time has passed (e.g. every 15 minutes).

The Device Manager 2590 may be able to create Sessions that contain recorded content. The Device Manager 2590 will rely on the interface provided by the Device Comm Processor 2589 to receive "mock" Device information of a digital nature. The Device Manager 2590 does not have to perform additional measures if control signals are embedded in a video stream.

The Device Manager 2590 may implement the authentication approach used in the firmware of the devices. The Device Manager 2590 may desire to authenticate Devices at the beginning of an interactive Session. The Device Manager 2590 may utilize "Keep-Alive" authentication, where it sends a heartbeat signal to the device periodically. The Device firmware may automatically terminate the Session if it does not receive this heartbeat within a specified time.

Note that it should use missing numerous heartbeat signals in order to not prematurely terminate the session. The Device Manager 2590 may desire to support authentication methods specific to each device in a Session. For example, it would be possible for one of the devices to have a version of firmware that uses one type of authentication, while the other Device might use another type of authentication.

In addition to what has been described, the Device Manager 2590 is able to perform other critical functions. The Device Manager 2590 should generally utilize the Database for logging activity. The Device Manager 2590 does not desire to log all control signals passed through, but there may be value to logging some/all of these. The Device Manager 2590 may be able to manage firmware updates with The Company's Devices. The procedure used by the Device Manager 2590 to update firmware may be able to recover from errors. The Device Manager 2590 may route connections from the Devices directly to the Device Comm Processor 2589 (e.g. a Session between a Device and the Device Comm Processor). The Device Manager 2590 may route a "copy" of the control signals of a Session to the Device Comm Processor for processing/recording. The Device Manager may route the control signals of a Session through the Device Comm Processor 2589. The Device receive TCP/IP connection requests from The Company's Devices, and validate the request against device-specific information. After connection initiation, further communications with each interactive device should be using device-specific encryption information.

The analog communication that physically occurs between the devices through the audio dongle is outside the scope of the SPWS. However, tunneled control values that are sent through that interface can be tunneled through the SPWS in digital format.

The Device Manager 2590 may provide an API that is a bi-directional interface with the Session Manager. The Device Manager 2590 can assume that the Session Manager 2591 is a "trusted" actor. The Device Manager 2590 may use an implementation that is scalable to multiple Session Managers and that does not use the Session Manager 2591 application to run on the same physical machine. The Device Manager 2590 may support event notification requests from the Session Manager.

An initial list of commands is shown below in Table 2 and an initial list of parameters is described in Table 3. Note that we desire to distinguish between source types that are Devices and "artificial" ones that are from the Device Comm Processor 2589.

TABLE 2

List of commands

| Name | Parameter(s) | Returns |
| --- | --- | --- |
| SessionInitiationRequest | VendorCredentials, SessionType, SerialNumberMap | SessionId |
| ModifySessionRequest | VendorCredentials, SessionId, ActionType, SerialNumberMap | Bool |
| InitiateRegistrationRequest | SerialNumber | isSerialNumberValid, isDeviceConnected |
| SimpleSessionInitRequest | VendorCredentials | SessionID |
| SimpleSessionAddRequest | VendorCredentials, SessionID, DeviceID | Bool |
| SimpleSessionRemoveRequest | VendorCredentials, SessionID, DeviceID | Bool |
| IsConnectedRequest | VendorCredentials, DeviceID | Bool |
| DownloadRoutineRequest | DeviceID, RoutineID, SlotID | Bool |

Manager 2590 may be able to send audio signals that correspond to the "Communication Protocol" document. It will receive these signals from the Device Comm Processor 2589. The Device Manager 2590 may be able to receive audio signals that correspond to the "Communication Protocol" document. The Device Manager 2590 is critical to overall IWS performance and may be able to be thoroughly tested prior to customer release. The Device Manager 2590 may be able to accept simulated loads in order to enable stress testing of the system. The Device Manager should have the capability to measure the connection quality. This may be done by "ping delay" or other such mechanism. The Device Manager 2590 may desire to detect variability in instantaneous quality in order to assess overall Session quality. The Device Manager 2590 expose this information to the Session Manager The Device Manager 2590 may implement the Digital Communication Protocol as outlined in the "Communication Protocol" document. The Device Manager 2590 may

TABLE 3

List of parameters

| Parameter | Description |
| --- | --- |
| VendorCredentials | The Vendor ID and whatever security related credentials that are used |
| SessionType | One-to-One, One-To-Many, One-To-Many-With-Alpha, Many-To-Many, Recorded Content |
| SessionID | A unique identifier for the Session. |
| SerialNumberMap | A mapping of the devices currently participating in a session, and where their control signals should go. |
| ActionType | Sessions could be modified in numerous ways, this may specify the action. |

Device Communication Processor

Figure 26:
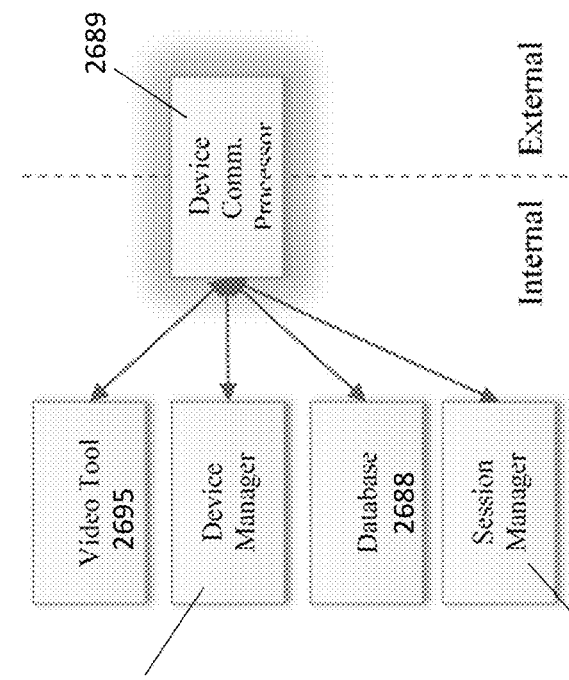

The Device Comm Processor 2689 enables the SPWS to create outgoing and process incoming control signals for The Company's Devices. An overview of the device communication processor is shown in FIG. 26. The device communication processor has a number of external dependencies. The device communication processor may provide an interface for the Video Tool 2695. The device communication processor 2689 may provide an interface for the Device Manager 2690. The device communication processor 2689 may provide an interface for the Session Manager 2691. The device communication processor 2689 may use the interface provided by the Database. The device communication processor 2689 may mimic the interface of The Company's Devices 2600, 2640.

The device communication processor 2689 is able to use a combination of stored information in the Database 2688 and algorithms to create device-specific Session-type activity. The device communication processor is able to provide an interface so other modules can create stored content. The device communication processor 2689 may be able to create audio and digital control signals for The Company's Devices 2600, 2640. The device communication processor 2689 may provide an interface to enable non-hardware based devices to create signals. This will enable creation of Routines and the control signals to accompany videos. The device communication processor 2689 may store these signals to the database.

The exact nature of the recorded signals may vary. One approach is "raw," where the digital representation of the analog signals are represented at a certain frequency. Another approach is a parametrized version, where activity is reduced to a more compressed version.

The device communication processor 2689 may be able to perform encryption activities that The Company's Device 2600, 2640 would do when communicating with another Device. For example, if the encryption scheme employed for Device-Device communication included the SPWS providing a key to use for encrypting communication with the other Device, then the device communication processor 2689 may also be able to perform this encrypt/decrypt.

The device communication processor 2689 has the ability to record Sessions or Routines directly from the interactive devices. If the user chooses to record Sessions or Routines "to the cloud," the Device Manager 2690 will route the control signal to the Device Comm Processor 2689, and the Device Comm Processor 2689 may record it. The device communication processor 2689 will likely have to decrypt incoming messages. Communication with the IWS for purposes of recording should use the same level of security as Device-Device communication.

The device communication processor 2689 has the ability to interface with the Device Manager 2690. The Device Comm Processor 2689 should present an interface to the Device Manager 2690 that is very similar to The Company's Devices 2600, 2640. The Device Comm Processor 2689 should not use additional complexity to be added to the Device Manager 2690.

Session Manager

Figure 27:
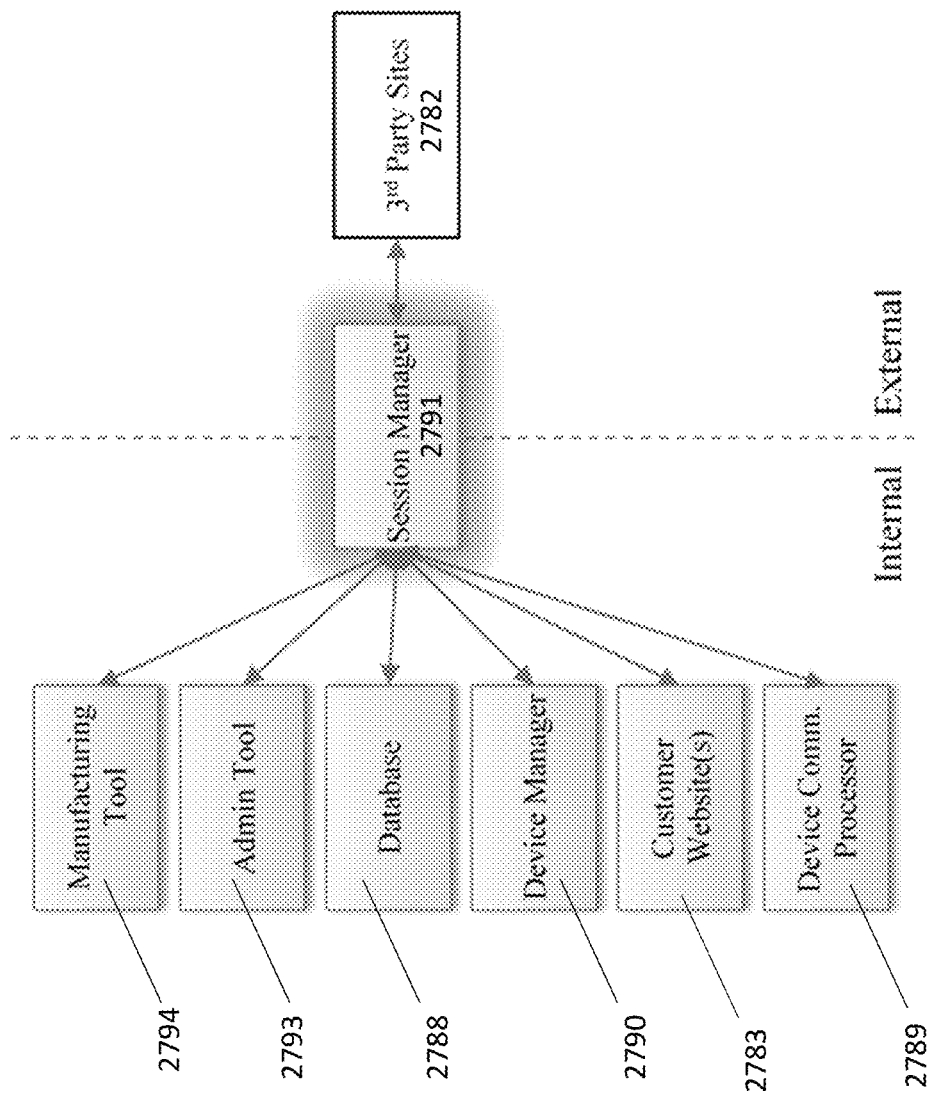
FIG. 27 is a block diagram showing a session manager interfacing with various components of the web software.

The Session Manager 2791 enables other software entities to observe and control activity of the Device Manager 2790 as shown in FIG. 27. The Session Manager 2791 has external dependencies. The Session Manager 2791 may provide an interface for the Admin Tool 2793. The Session Manager 2793 may provide an interface for the Manufacturing Tool 2794. The Session Manager 2793 may provide an interface for the Customer Website(s) 2783. The Session Manager 2793 may provide an interface for the Third Party Sites 2782. The Session Manager 2791 may use the interface provided by the Database 2788. The Session Manager 2791 may use the interface provided by the Device Comm Processor 2789. The Session Manager may use the interface provided by the Device Manager 2790.

The Session Manager 2791 enables other modules to initiate Sessions. The Session Manager 2791 may be able to initiate/create Sessions between The Company's Devices by using the Device Manager 2790. The Session Manager 2791 may provide the requestor with the result of the initiation request (e.g. success, fail, pending). The Session Manager 2791 may be able to create all Session types (e.g. one-to-one, one-to-many, many-to-many, and pre-recorded)

The Session Manager 2791 venables other modules to modify Sessions. The Session Manager 2791 may enable other modules to add participants to existing Sessions. The Session Manager 2791 may enable other modules to remove participants from existing Sessions. The Session Manager 2791 may enable other modules to terminate existing Sessions. The Session Manager 2791 may enable other modules to remap the control signals in an existing Session.

The Session Manager 2791 records all transactions. The Session manager 2791 may record all requests to initiate, modify, and terminate Sessions. This is the most important logging that may be performed. The Session Manager 2791 should record all other activity. The Session Manager 2791 exposes "low-level" Device Manager 2790 functionality for use by trusted modules. The Session Manager acts as the interface between modules like the Admin Tool 2793 and the Device Manager 2790. The Session Manager 2791 may enforce "Permitted Activity" levels. The Company's Device can be configured in numerous "modes," which restrict the "Permitted Activity" of the Device.

The Session Manager 2791 acts as an intermediary between the Device Manager 2790 and other modules. The Session Manager 2791 provides an abstracted and simplified interface to the Device Module. As such, it will often be the logical interface to use for modules seeking to interact with The Company's Devices. The Session Manager 2791 may perform activities that build upon the Device Module functionality (e.g. monitoring, monogamy mode enforcement) that other modules should rely on.

The Session Manager 2791 may provide an industry standard web API for Third Party Access. An industry standard web API should be chosen that the majority of Third Party partners will be willing to adopt. A RESTful API may be implemented. SPWS functionality may be exposed through numerous APIs. However, the addition of each extra API should be highly scrutinized because of direct costs (development, testing), and indirect costs (maintenance, documentation).

The Session Manager 2791 may enable The Company's Customer Website(s). The Session Manager 2791 may implement all "low-level" features useful to The Company's Customer Website(s) in order to provide the specified customer experience. Session Manager 2791 functionality may desire to be extended as the needs of the Customer Website(s) 2783 evolve.

Interfacing with Third Party Websites

An industry standard web API may be implemented. It is recommended to implement a RESTful API. The web API should be easy for third parties to use. The web API should be well documented. A stateless implementation of the SC should be implemented. A javascript implementation may be provided.

A secure vendor access system may be implemented. A secure access mechanism may be used that allows for access control on the vendor level. This may take the form of a unique userID and a separately provided key. The access keys may not be able to be easily spoofed (e.g. sequential vendor IDs without passwords may not be used). The system may log all interaction with the third parties. The system should have the ability to temporarily revoke vendor access. The system may provide for tracking of different SKUs per vendor, allowing for requests of different value session rates.

The functionality used by the third parties may be exposed. Third Parties 2782 may be able to initiate the various session types. The success or failure of each command may be communicated to the Third Party 2782. Third Parties 2782 may be able to terminate a session. Third Parties may be able to remove individual users from a group session. Either the SC or the Customer Facing Website popup may handle the registration process. This will include numerous steps.

Intentional abuse of the IWS may be prevented. Third parties should only have access to the minimum amount of functionality to perform their used activities. The interface should not allow scraping of data. The interface should not allow any sequence of events that could erase or hide session requests.

The Session Manager 2791 should enable connections with different types of Third Party Sites 2782. Integration with Cam Sites will be used. Integration with Dating Sites may be used. Integration with video streaming sites may be used. Other types of website integration may be used. Different types of Third Party Sites 2782 may use different functionality from the Session Manager 2791 and/or the IWS in general.

Figure 34:
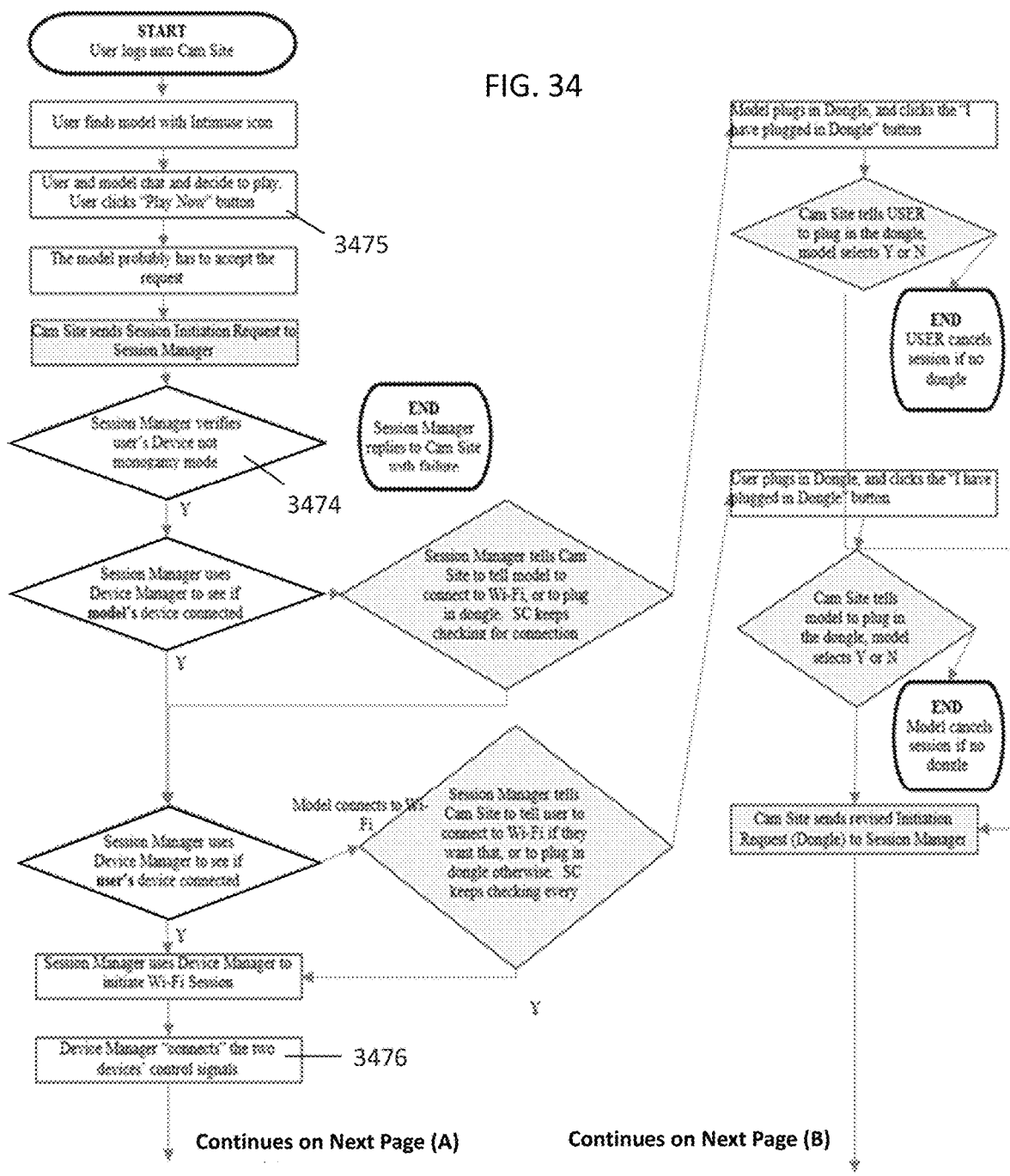
FIG. 34 is a flowchart showing a simplex communication mode session where the users are participating in a one-on-one session on a cam site.

FIG. 34 shows a flowchart for a user participating in a one-on-one session with a third party provider (e.g. CAM site). Users may first chat with individuals active on a CAM site (e.g. CAM girls) If the CAM girl accepts a request from a user to have a session, the session manager will verify the interactive devices' serial codes and that neither device are set to monogamous mode 3474. Session manager is able to verify that the interactive user and the CAM girl are both connected. The session manager may communication to the CAM girl through the CAM site to connect for a session either through the dongle or an internet connection. Similarly the session manager will instruct the interactive user to connect via the dongle or an internet connection. The device manager is then able to connect the two devices 3476. The right side of FIG. 34 shows the actions that would occur if a dongle is used, while the left side shows connection through an internet connection.

Company Customer Website(s)

The interface between the Session Manager and The Company's Customer Website(s) would be the same method that is used for the Third Party Interface. The Third Party Interface may be extended. If The Company's Customer Website(s) use additional functionality, the interface between the Session Manager Third Party Interface could be extended. This additional functionality could be due to lack of restrictions imposed by the Third Party. This additional functionality could take advantage of the fact that The Company's Customer Website(s) would be a "trusted" source, unlike the Third Party Websites. This extended functionality might not be made available to the Third Parties.

A separate interface may be implemented if needed. Specific performance or other such needs would have to be uncovered for an entirely separate interface to be implemented. Although other connectivity options may be easier to implement in the short run, the significant advantages to using the same interface as the Third party would have to be outweighed.

Customer Websites

Figure 28:
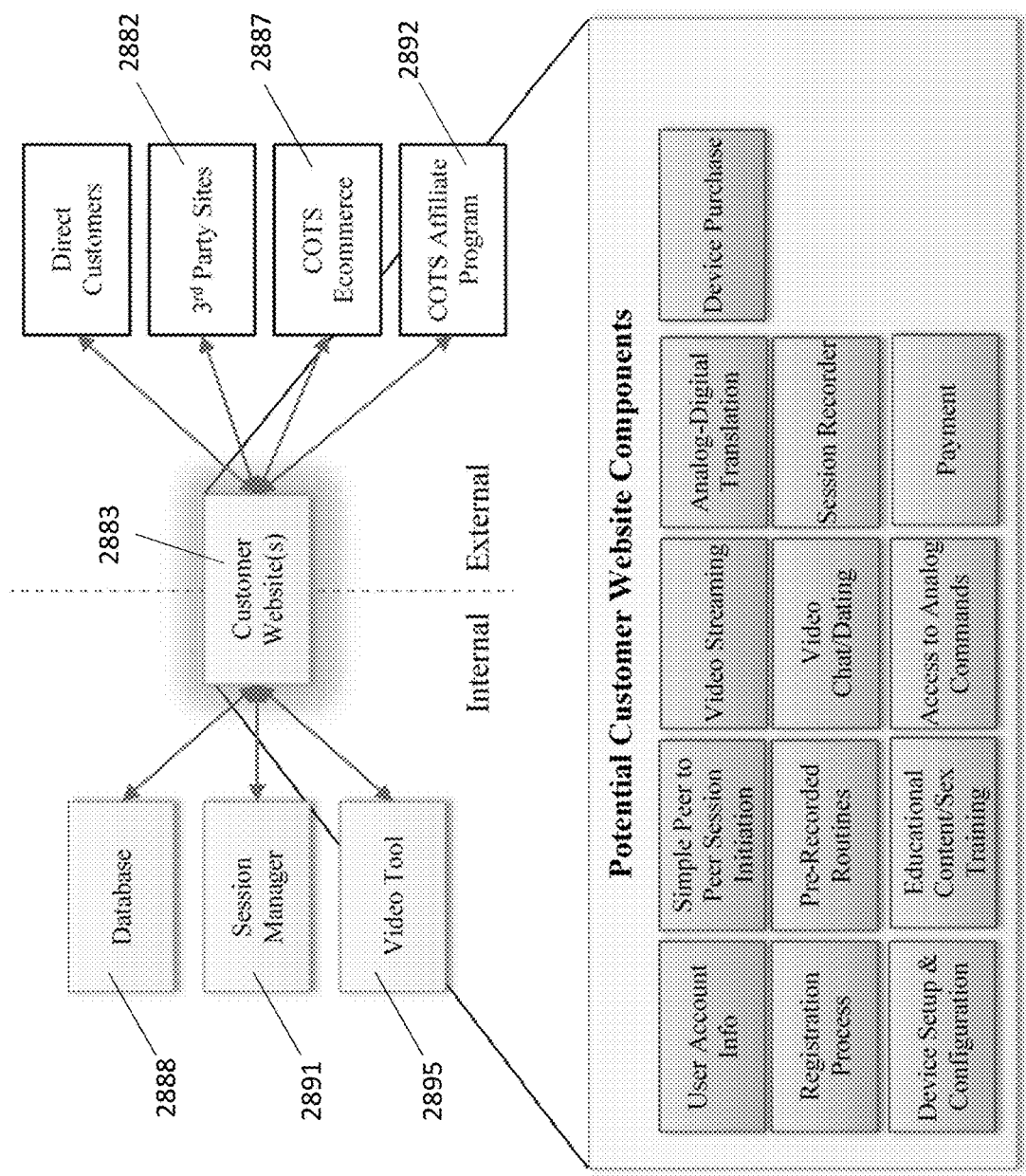
FIG. 28 is a block diagram showing customer websites that interfaces the Company web software with external programs and components.

Direct Customers can use the SPWS to perform a variety of activities, ranging from registration of their device to initiating sessions as shown in FIG. 28. The Customer Facing Website(s) 2883 module is a catchall for a variety of customer facing websites that The Company's may choose to implement. The following points describe both general, shared features, as well as specific differentiated offerings. It is possible that various offerings may be combined in different ways or branded under a different name.

The Customer Websites 2883 may contain external dependencies. The Customer Website(s) 2883 may provide an interface for Direct Customers to use. The Customer Website(s) may provide an interface for Third Party Sites 2882 to use, and may also use interfaces provided by Third Party Sites 2882. The Customer Website(s) 2883 may utilize the interface provided by the COTS Ecommerce 2887 platform. The Customer Website(s) 2883 may use the interface provided by the COTS Affiliate Program 2892. The Customer Website(s) 2883 may use the interface provided by the Database 2888. The Customer Website(s) 2883 may use the interface provided by the Session Manager 2891. The Customer Website(s) 2883 may use the interface provided by the Video Tool 2895.

The Customer Website(s) 2883 module may consist of numerous sub-modules (or Components) based on functionality. Components currently identified include User Account Information, Registration Process, Device Configuration, Simple Peer-to-Peer Session Initiation, Pre-Recorded Routines, Educational Content, Video Streaming Site, and Dating Site. These Components should be built off of COTS solutions where appropriate. These Components should be reused where possible. These Components may be made available to Third parties in order to simplify integration with Third parties and to provide a unified customer experience.

Users should be able to create a The Company's Account on The Company's Website. The Company's Account should contain the minimum amount of information used to administer an account while enabling secure password reset. This means username, password, and email. The Company's Account creation process may also include date of birth and location. The Company's Account creation process may use users to acknowledge that they are old enough to use the system, or other such disclaimers. The Company's Account system should not prompt users to authenticate through Third Party social networks (e.g. Facebook, Google, etc.).

The registration process should be as streamlined, simple, and "foolproof" as possible. At a minimum, registration may "link" the serial number of The Company's Device with some type of account. This account could be a The Company's account or it could be a Third party account. A device should be able to be "linked" to multiple accounts, in case the user wants to use their The Company's Device on multiple sites.

In order to streamline their registration experience, The Company's may not want users that have launched the registration process from a Third party to have to create a The Company's-specific account prior to registering their device. However, there are advantages to always requiring a The Company's account (e.g. password recovery, unified structure) that should be considered. Physical possession of the device may be verified as part of registration. This could be by requiring connectivity and using a button press, or could be done by a registration code that is provided in addition to the serial number. Requiring only the serial number could lead to a malicious party registering devices that they do not own. Active connectivity with the IWS could be verified as part of registration. Functionality of their device (e.g. motor and sensor functionality) could be verified as part of registration. The latest firmware could be downloaded to The Company's Devices as part of registration.

A Component should exist that enables users to setup and configure their Devices. This Component should enable the user to explore and set user-preferences. Device Configuration should include the ability to "link" two Devices to each other in monogamy mode. Device Configuration may include the ability to customize how the different mechanisms of the Device work. For example, thrust depths, velocity profiles, and other aspects may be configured. Device Configuration may be part of the user account, or it may be separate. If The Company's allows registration of Devices without creating a The Company's account, the Device Configuration should be separate from user accounts.

The Company's Customer Website should have a component that enables simple peer-to-peer session initiation. This would enable users to have a session using a Third Party video platform (e.g. Skype). Note that monogamous devices could be automatically connected, and wouldn't desire this Component.

Method 1: This Component could use Device serial numbers to "directly" connect the Devices.

Method 2: This Component could use The Company's usernames to "directly" connect the Devices, assuming each user only had one device registered to their account.

Method 3 (preferred): This Component could enable one user to "host" a session, which could be identified by a "then-unique" session ID. That user could provide one (or more) users the code, over the Third party video or other means. The other user(s) would log into The Company's website, enter the code, and be connected to the Session. Note that this could be used to set up one-to-one as well as one-to-many or many-to-many Sessions (provided there was an interface to configure the Session control signals). This can be thought of as the "GotoMeeting" Method, and many options similar to hosting an online meeting (organizer, presenter, muting participants, chat, etc.) could add value to this experience. This approach could use a password or the host's approval prior to connecting a new user to the Session, thus providing a level of security.

Privacy implications may be considered when choosing and implementing a Method for this Component. Methods 1 and 2 contain semi-private information, which is not ideal. Method 3 provides a good level of anonymity. "Trolling" has to be prevented, where uninvited or unwanted users try to connect with a user without their consent. This includes a situation where two users had a session together, but then one user didn't want to have a session with the other user anymore. Connections to a Session should always use confirmation to join the Session by all users. This prevents inadvertent connections. The only possible exception to this would be two devices in monogamous mode.

Figure 33:
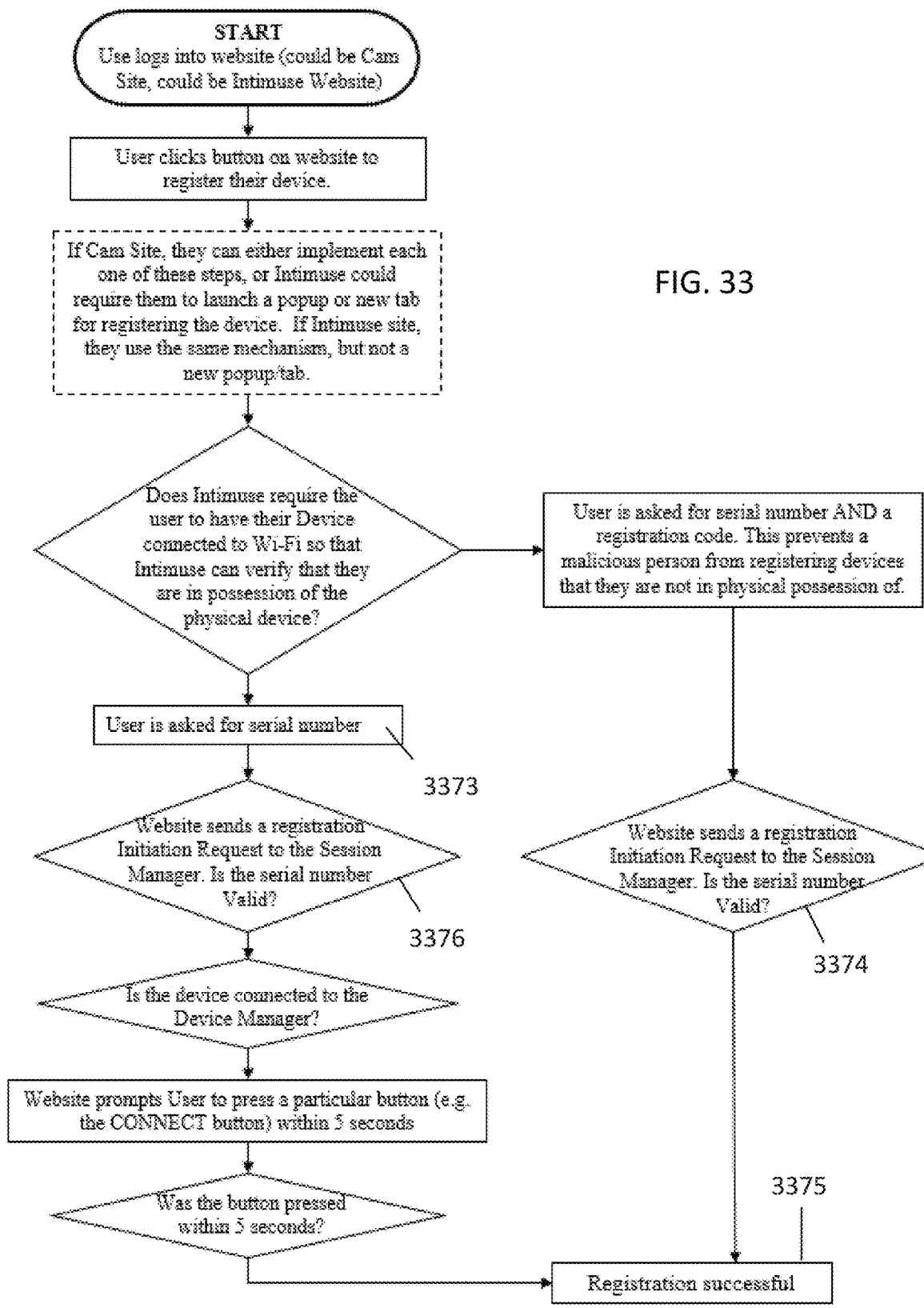
FIG. 33 is a flowchart showing how the interactive device is registered and authenticated.

FIG. 33 shows a flowchart of the range of possibilities for registering the interactive device. A user will typically log into the Company website or a third party site where the user may register the device. If the user is logging in through the Company website, they may be asked to verify that they have the physical device. This may be through a serial number or a registration code 3373. The session request may then be sent to the Company's session manager to validate the serial number or registration code 3376. Once the device has been authenticated, it will be able to interact with other devices where the Company's device manager is able to manage the connection.

Figure 35:
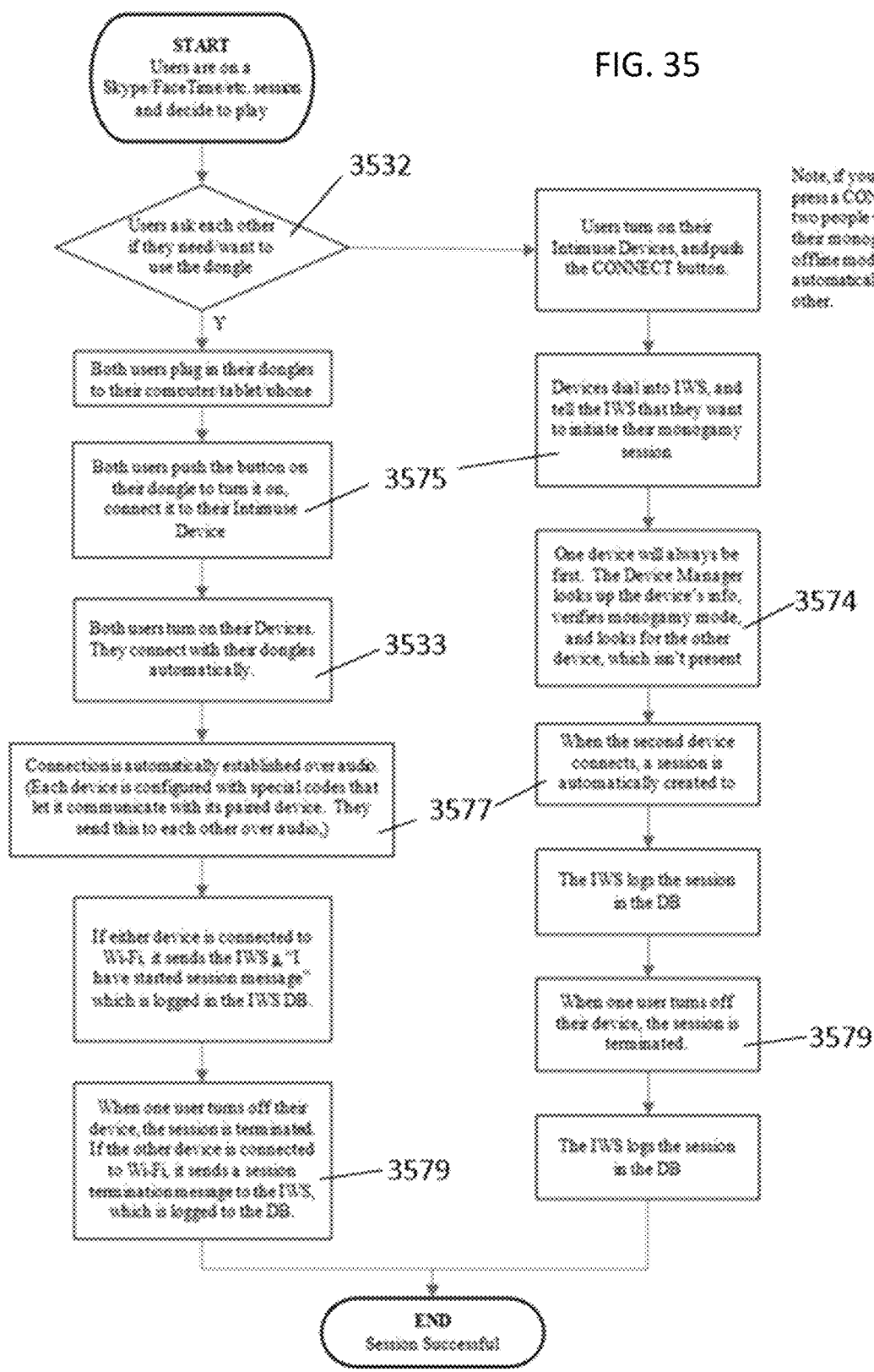
FIG. 35 is a flowchart showing a two user scenario conducted under a monogamous session using third party video.

FIG. 35 shows a flowchart of two users conducting a monogamous session using third party video. Initially, the two users may communicate through other available means and decide to commence a session. The user may dial into the IWS and initiate a session or both users may plug their dongle into their computer, tablet, smart phone, and so forth. In the latter case, one device will connect first and prompt the device manager to look up the device information 3574. When the second device connects, a session will automatically be created 3577. The ISW will log the session in the Company database and the session will terminate when one user turns off his or her device. In the case where the users employ the dongles, both users may automatically connect through the dongle 3533. Connection is automatic over audio where each device is configured with unique codes that let the device communicated with its paired device over audio 3577. Once authenticated a session may be initiated and the session logged in the database. A session ends when one use turns of their device 3579.

If the SPWS enables users to download or stream pre-recorded routines, the Customer Website(s) module would be how the user accesses these routines. The Customer Website could handle downloading and streaming content differently. The Customer Website would command the Session Manager to download a specific routine. The Customer Website may communicate with The Company's Device (through the appropriate IWS modules) to determine the routines that are currently stored on the device. This could be used to show the user what Routine is stored in which slot, and could be used to verify downloading of routines. This Component could use audio control signals, digital control signals, or both. This Component could provide content divided into intensity type (slow/hard), time ("I have 5 minutes"), or other characteristics. This Component could contain content generated by adult performers.

The Customer Website may enable the ability to download or stream routines related to sex training. These would likely be specialized pre-recorded routines. Content could include Kegel exercise training, ejaculation control, and related activities. This Component could communicate with the devices to measure performance during individual training sessions and across time. This Component could use video in combination with the training content. This Component could use audio control signals, digital control signals, or both. This Component could contain videos and other material that discuss device use, maintenance, and troubleshooting. A FAQ section would be appropriate.

The Customer Website may have a component that enables users to stream video content that is enhanced with signals that control their The Company's Device. This Component may have the control signals divided into types of activity (e.g. slow, soft, hard, fast, blowjob, etc.). Alternatively, this Component may use control signals that mimic the signals sent by another The Company's Device. This Component would get its content from an interface exposed by the Video Tool. This Component may use analog, digital, or both types of control signals.

The Customer Website may have a Component that enables users to browse for and have encounters with other users. This Component should have built in video chat. This Component may use a membership, pay-per-session, pay-per-minute, or other such fee-based mechanism. This Component should allow users to have "favorites". This Component should allow users to see who is online and ready to have an interactive experience. This Component should allow users to chat with each other. This Component should easily enable users to set up a "date" if the other person is not online. This Component should have user profiles that can be customized by the user. This would include photos, descriptions, activities that they will perform, etc. This Component should have different levels of privacy, or exposure, that the user can choose for their profile. This Component should let users block specific other users. This Component should let users filter by aspects common in dating sites (e.g. age, hair color, etc.). This Component should have disclaimers that let the user know that it is impossible for this website to prevent other people from taking screenshots and/or making videos. It should also remind people that recording is illegal and that The Company's will help users prosecute any violation of this. This Component may be able to use content embedded in the video to identify the users of the devices, in order to deter recording and/or facilitate prosecution. This Component may include a personality test or other such compatibility metric. It may link to other sites that perform this service. Other Dating Sites (match.com, Tinder, etc.) should be consulted prior to finalizing the functionality of this Component and after deployment. If features of other sites are not protected by IP and add value to the customer, The Company's should consider integrating them into this Component. This Component may have a "rating" system, where other users can leave feedback about a user.

The Customer Website may have a Component that enables requestors to receive an audio command that can be played to the Dongle of the connected Device. These Commands may be device-specific. This Component may enable streaming of commands generated by the Device Comm Processor that can be processed by the Dongle. This Component may be extended to be able to receive audio signals, thus enabling bi-directional communication.

If the Company's Customer-facing website (IWEB) was handling piping user audio and video, it could run algorithms on incoming/outgoing data to inject or remove audio dongle signals from the audio stream. This would likely be very computationally intensive and could introduce delays. The Analog-Digital Translation should probably exist as part of the Device Comm Processor, since it is dependent on the Hardware.

The Customer Website(s) may have a Component that enables recording of Session or Routines by the SPWS. This Component would rely on the Session Manager and other modules to actually perform the recording. This Component may store this content to a "library" for the user This Component may enable users to share this content with other users. Privacy implications may be fully evaluated prior to developing the Session Recorder Component.

The Customer Website(s) should have a Component dedicated to receiving/processing payment form customers. This Component should utilize an external COTS Ecommerce platform. This Component should store user payment info securely, and for future use. This Component should enable recurring payments. This Component should enable individual payments. This Component may abstract user payment info into "tokens" or other such concept. This Component may enable purchasing of minutes of device usage. This Component may enable purchasing of sessions. This Component may enable purchasing of subscriptions (e.g. monthly) to The Company's Website(s). This Component may enable "Unlimited Usage" of their device. This Component may enable purchasing of unlimited Interaction with an enhanced video.

The Customer Website(s) should have a Component dedicated to enabling the customer to purchase The Company's Devices. This Component should integrate with the order fulfillment warehouse. If appropriate, it should make use of a COTS Affiliate Program to refer customers directly to the ILF or other such website for order entry. This Component may make use of stored payment information in order to streamline the user's experience. In this case, if The Company's is directly receiving payment for the Device Purchase, this Component may also integrate with the order fulfillment warehouse on the appropriate level.

The Customer Website(s) should be accessible on most devices that a customer would use. Modern Windows computers may be supported. Modern Apple computers may be supported. Modern tablets may be supported (iOS, Android, and Windows). Linux may or may not be supported. The Company's should specify a minimum set of system needs for the user. The Company's should not make extra efforts to support legacy systems (e.g. Windows 98). Furthermore, The Customer Website(s) should be accessible on most browsers that a customer would use. Google Chrome may be supported. Internet Explorer may be supported. Firefox may be supported. Safari may be supported. Mobile versions of these browsers should also be considered.

Interfacing with Third Party Sites

The Customer Facing Website(s) may have components that integrate directly with Third Party Sites. These components should integrate in an industry-standard approach (e.g. RESTful API, javascript, etc.). These Components may use popups or new tabs to be used. The user experience should be considered when determining the method of integration, and the burden on the user should be minimized.

The Customer Facing Websites should include a mechanism (e.g. a popup of some sort) to handle the device registration process. Benefits include having a consistent user experience during registration, providing a simple integration mechanism for Third parties (thus reducing errors), and ability to iterate upon and improve the registration process without relying on Third parties to change their code.

Administrative (Admin) Tools

Figure 29:
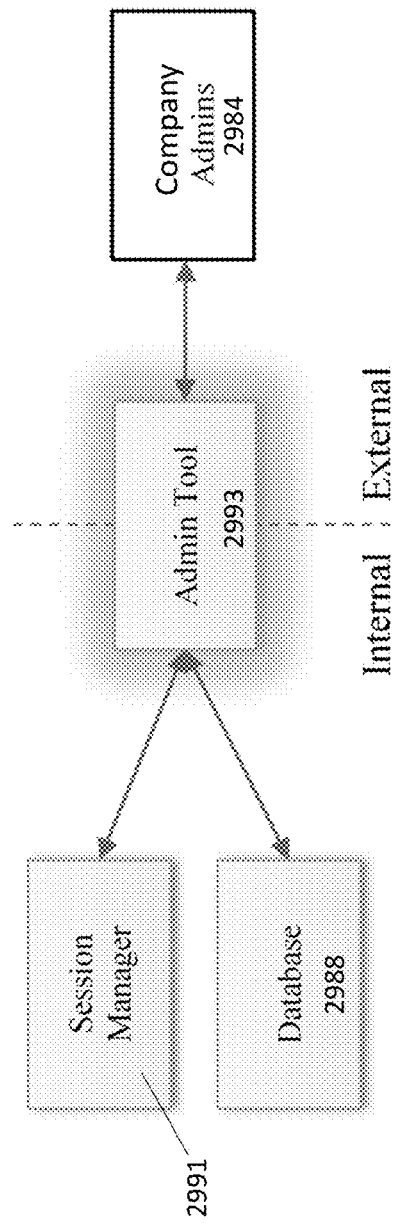
FIG. 29 is a block diagram showing an admin tool and its relation to other components of the web software.
Figure 30:
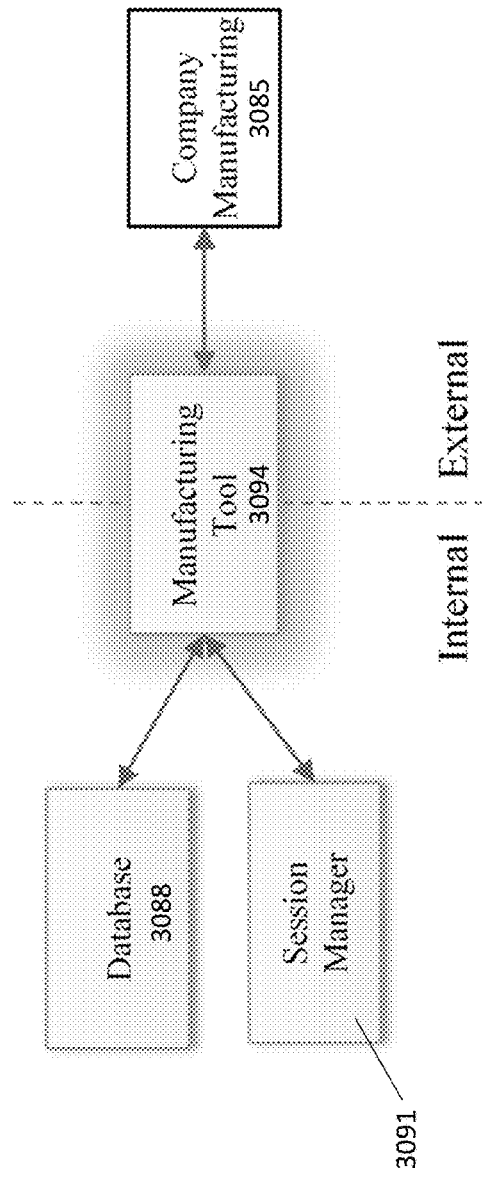
FIG. 30 is a block diagram showing a manufacturing tool and its relation to other web software components.

The Company's Admins 2984 use the SPWS to create vendor accounts, view usage information, and other administrative tasks as shown in FIG. 29. Admin Tools 2993 may have external dependencies. The Admin Tool 2993 may provide an interface for The Company's Admins 2984 to use. The Admin Tool 2993 may use the interface provided by the Session Manager 2991. The Admin Tool 2993 may use the interface provided by the Database 2988.

The ability to create vendor accounts may be provided. Vendor accounts shall, at a minimum, consist of a name, unique ID, and secure key with which the vendors can request session activity. It may include other information to simplify interactions with the vendor or ILF (e.g. ILF-specific vendor ID, address, email address, phone number, etc.). The ability to create SKUs or other methods for rate tracking. The ability to suspend accounts may be provided. The ability to delete accounts should not be provided. The interface could hide suspended accounts, or there could be a concept of vendor status (Active, suspended, cancelled), but once created, a vendor account should persist.

Ability to create reports of usage information. The ability to export usage information from the database may be provided. Usage information includes vendor ID, SKU number, Device IDs, Session Start Time and End Time. The information may be exported in XLSX or CSV format. The ability to filter by vendor and/or date range may be provided.

The ability to summarize the information exported may be provided. The Admin tool 2993 may rely on "post-processing" to create the summarized information. For example, Excel Macros may be used.

The Admin Tool 2993 may create "final" customer-facing usage documents in PDF format.

The Admin Tool 2993 may include ability to visualize key characteristics related to system performance This may include items like alarms, logs, CPU usage, number of simultaneous connections, and/or latency information. The Admin Tool 2993 may desire to collect and display diagnostic information directly from Cloud Components, in order to enable the Admin to make decisions related to scaling and other concepts. Diagnostic information could be presented in graph or raw data form. The diagnostic information should be "actionable." For example, problem conditions should be anticipated and information related to those conditions should be made available to the Admin. Action plans should be in place for these problem conditions.

The Admin Tool 2993 may include the ability to perform targeted activities to debug the system. The Admin Tool's 2993 debug capabilities should address issues that arise during engineering development that may persist after first customer release. For example, a potential user problem is that they think they are connected to the IWS, but they are not getting control signals from the Session. There could be numerous causes to this problem. The Admin Tool 2993 should be able to check out a session, see what Devices are connected to the Session, and possibly take actions to enable discovery of what the problem is. Ideally, the Admin Tool could also take actions to fix the problem. This may use the desire to manually enter Session IDs, Device serial numbers, etc.

The ability to initiate firmware upgrades with selected devices may be implemented. The Admin Tool 2993 will rely on the Device Manager to actually perform the upgrade, but the Tool may specify which Device, what firmware version, and other relevant parameters are to be used. The Admin Tool 2993 should enable admins to upload a new version of firmware to the IWS. The Admin may specify the relevant parameters (e.g. firmware version, etc.). The Admin Tool may support female and male toys, as well as the dongle.

The Admin Tool 2993 may use a minimum of typical username/password to control access to the tool. The Admin Tool 2993 may use other connectivity (e.g. VPN connection to the cloud based server). The Admin Tool 2993 may have access permission levels.

Functionality shared between the Admin Tool 2993 and the Manufacturing Tool should be implemented as shared modules. Implementations should not be duplicated between the Admin Tool and the Manufacturing Tool. If appropriate, the Manufacturing Tool could be a subset of the functionality implemented in the Admin Tool 2993. If that is the case, user access permission levels could restrict access of Manufacturing Personnel to the more sensitive areas of the Admin Tool 2993.

The Company's Admin Tool could be web-based. If possible, the Admin Tool 2993 should be web-based. As currently envisioned, the Admin Tool 2993 does not use any direct connection to hardware. The Admin Tool 2993 should be supported on updated browsers. The Admin Tool 2993 should minimize dependence on out-of-date plug-ins or other software components. For example, the Admin should not be used to download an out-of-date version of Java. The Company's Admin Tool 2993 could be a native application running on a server within the SPWS. This approach may minimize development, but would use users to have access to the IWS network.

Manufacturing Tools

Figure 31:
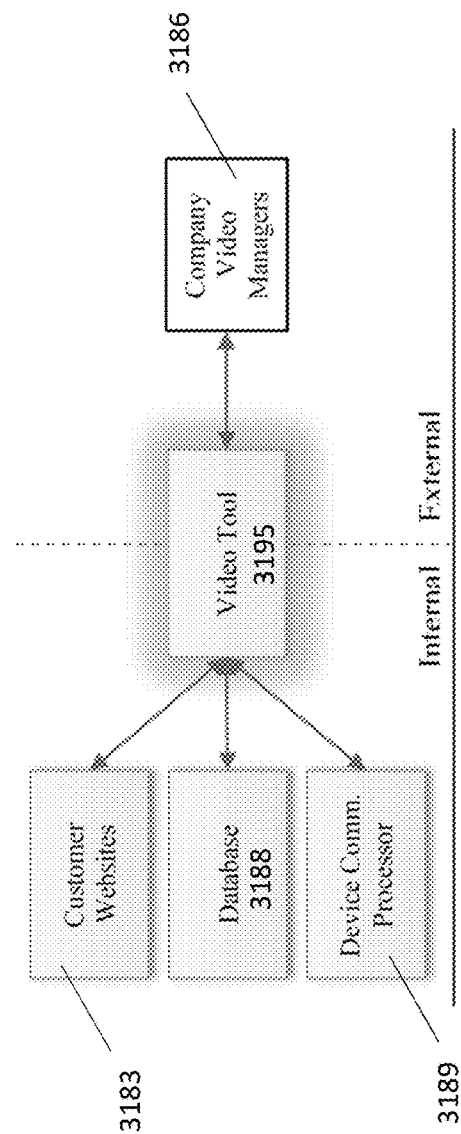
FIG. 31 show a block diagram of a video tool and its relation to other web software components.

The Company's Manufacturing Personnel 3085 are responsible for ensuring that The Company's Devices are ready to be shipped to the customer (See FIG. 31). This will likely include performing a final quality control test, but will likely also use ability to "link up" The Company's Device with the SPWS's secure communication methodology. The Company's Manufacturing Tool 3094 will enable Manufacturing Personnel to perform test activities that use the use of the SPWS. The Manufacturing Tool 3094 may provide an interface for The Company's Manufacturing Personnel to use. The Manufacturing Tool 3094 may use the interface provided by the Session Manager 3091. The Manufacturing Tool 3094 may use the interface provided by the Database 3088.

This tool may enable manufacturing personnel to synchronize device-specific encryption information with the SPWS. This may include the generation of such information on the IWS and the downloading of the info to the devices, or it may consist of reading unique information from the device and placing it in the SPWS. This tool should enable manufacturing personnel to initiate specific SPWS originated diagnostic tests. For example, the ability to connect with the IWS using an encrypted connection may be present. Other functionality that can be tested in other ways is optional (e.g. motor functionality). This tool may enable manufacturing personnel to perform final test of the device.

If the devices do not come from the manufacturer with production firmware, this tool should have the ability to program the device with the release version of the firmware for both the male and female devices. This tool may desire to have the ability to select between release and test versions of the firmware.

If pre-recorded routines are not included in the firmware, this tool should have the ability to download the pre-recorded routines to the device that are supposed to be accessible "out of the box". This tool should only expose the functionality desired by the Manufacturing Personnel 3085. This tool should use little training to use The Manufacturing Tool 3094 may use a minimum of typical username/password to control access to the tool. The Manufacturing Tool 3094 may use other connectivity (e.g. VPN connection to the cloud based server). The Manufacturing Tool 3094 may have access permission levels.

Manufacturing Tool 3094 related activity should be logged. In order to help detect misuse or abuse of the Manufacturing Tool 3094, the activity requested by the tool should be logged.

Ability to register and/or pre-configure devices. This Tool may implement the ability to register devices that are ordered by the user. If the order fulfillment warehouse has access to the IWS, has barcodes on the box or device, and has some user-specific information (e.g. username on the invoice), the Manufacturing Personnel 3085 could automatically register the device by scanning the barcode on the device. Note that this would use tight configuration between the order fulfillment partner and the IWS. This Tool may facilitate configuring devices so that they work better when the user receives them. This may include programming WiFi SSID and password or other configuration parameters. The Manufacturing Tool 3094 could contain content to train Manufacturing Personnel 3085.

Video Tool

The Company's Video Tool 3195 enables The Company's Video Managers 3186 to prepare videos for use with The Company's Devices is shown in FIG. 31. The Video Tool 3195 may enable The Company's Video Managers 3186 to "edit" videos so that they have the ability to control The Company's Devices. The Video Tool 3195 may use the Device Comm Processor 3189 to modify the audio track of the video to contain embedded audio control signals. The Video Tool 3195 may use the Device Comm Processor 3189 to create a "parallel" digital control track for the video that could be streamed alongside the video. The Video Tool 3195 may include functionality to edit the video so that it can provide a more compelling user experience. The Video Tool 3195 may have to create content specific to male devices, female devices, and content that could be used by both types of devices.

The Video Tool 3195 should have a method for The Company's Video Manager 3186 to synchronize content. The Video Tool 3195 should have a means to generate commands for controlling the various modes of the male and female devices. The Video Tool 3195 may convert mouse signals into commands The Video Tool 3195 may convert keyboard strokes into commands. The Video Tool 3195 may provide a layout similar to a video editor that shows the video track, audio tracks, and the control tracks. This could allow The Company's Video Manager 3186 to specify different regions of activity in a visual manner. It will likely be cumbersome for the Video Tool 3195 to use direct signals from The Company's Device to synchronize the tracks. However, this may provide the most realistic experience. Since this development will be relatively complicated, the related costs should be considered. The Video Tool 3195 may work in conjunction with Routines in order to simplify the enhancement of videos.

The Video Tool 3195 should be implemented in the most robust, lowest cost method. It is expected that the number of The Company's Video Managers 3186 will be very limited. As such, the tools for them do not desire to be cross-platform. The Tool may be implemented as part of the SPWS, as a separate executable, or with portions in each. The Tool should be able to run on modern Windows computers. Compatibility with Macs is not used. This would use additional development for a very targeted audience. It would be cheaper to supply Video Managers 3186 that only have a Mac with a Windows laptop than to develop for both platforms. The Tool does not have to run on tablets or mobile devices. The Video Tool 3195 should use COTS components when possible.

Database

Figure 32:
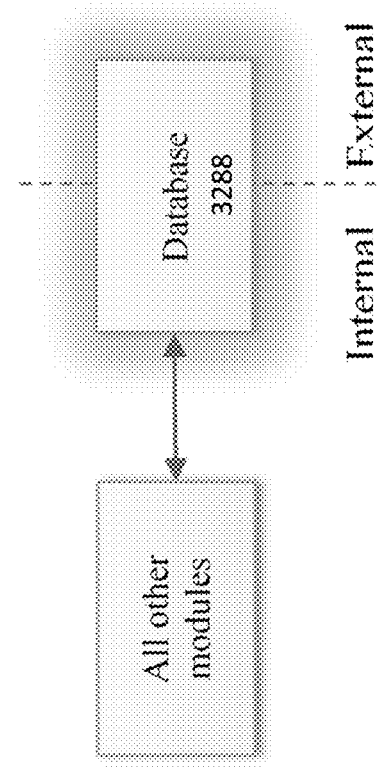
FIG. 32 shows a high level block diagram of a database module as it relates to all other modules.

The Database 3288 module provides an organized collection of data for the other system modules as shown in FIG. 32. A cloud-based relational database management system should be used. Based on the current understanding of the database needs, MS SQL Server, MySQL, or similar RDMS should be used as the underlying database application for the majority of the data. A non-relational database implementation should only be pursued if new desires arise. Fully managed cloud-based database modules should be favored over self-managed instances. For example, in the AWS Ecosystem, Amazon RDS should be used instead of a self-managed MS SQL instance on an EC2 server.

The Database 3288 module may utilize numerous storage access methods "under the hood". The Database 3288 may use different underlying database technologies that are appropriate for the content being stored. For example, "slower" access methods (e.g. Amazon Redshift, Amazon Glacier) could be used for archival and backup, while "faster" methods (e.g. Amazon Elasticache) could be used for frequently accessed information. The Database interface should "hide" the underlying implementation.

Backup and disaster recovery processes may be in place and tested. The functionality provided with respect to backup and disaster recovery from the fully-managed cloud solution should be utilized to a level suitable for The Company's risk tolerance level. A written plan for disaster detection and recovery may be established. Responsible parties may be identified. The entire SPWS may be implemented as "stateless" as possible and any relevant states will be stored in the Database 3288.

When appropriate, individual modules (e.g. Device Manager) could have an internal microservice that implement database functionality. If individual modules use data storage that is not related to other modules, or if they are simply related, it may be more appropriate to implement a database microservice within the module. These internal microservices should still be fully managed and cloud-based. These internal microservices still may be subject to the backup and disaster recovery process need. Finally, a Database 3288 schema should be developed such that data is organized logically, with no conflicts or redundancies.

Artificial Intelligence

Any of the apparatuses (e.g., devices and systems) described herein may be controlled by a machine emulating human interaction, which may control the operation (feedback) from a paired device and/or may communicate with a user. For example, any of the apparatuses described herein may be controlled by an artificial intelligence (AI) application or system, including an AI system that emulates human behavior and interaction, including conversation. Systems that communicate with one or more AIs may be particularly desirable for users that do not want to deal with an actual human yet do not want to use stored (e.g., prerecorded) interactions. An AI may emulate actual interaction and may provide a way to control the devices realistically that could be an optimal way to deliver interaction in device movement and/or verbal and/or visual stimulation.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A device for mimicking a portion of the male genitalia, the device comprising:
    a tubular body having:
        a shaft,
        a massager sub-assembly coupled to the shaft, the massager sub-assembly being movable relative to the shaft, and
        a sheath covering the shaft and the massager sub-assembly; and
    a twisted-string drive having:
        a string coupled to the massager sub-assembly and configured to twist and untwist around itself to change length and drive movement of the massager sub-assembly relative to the shaft, and
        a motor at one end of the string configured to twist and untwist the string.

2. The device of claim 1, wherein the string is part of a pair of strings coupled to the massager sub-assembly and configured to twist and untwist around each other to change length and drive movement of the massage sub-assembly relative to the shaft.

3. The device of claim 1, wherein the twisted-string drive further comprises a spring member at another end of the string configured to maintain tension on the string.

4. The device of claim 1, wherein the string comprises a nylon string.

5. The device of claim 1, further comprising a position sensor configured to sense a position of the twisted-string drive.

6. The device of claim 1, wherein the massager sub-assembly is configured to expand and contract relative to the diameter of the shaft.

7. The device of claim 1, further comprising an input connected to a controller to drive actuation of the twisted-string drive.

8. The device of claim 1, wherein the sheath has a diameter between about 1 cm to about 3 cm.

9. The device of claim 1, wherein the massager sub-assembly further comprises a rigid core and a balloon portion, wherein the balloon portion is inflatable.

10. The device of claim 1, further comprising control circuitry, wherein the control circuitry comprises a microcontroller, a battery management circuit, and a wireless communication circuit.

11. The device of claim 1, further comprising a user input controlling a motion of the massager sub-assembly.

12. The device of claim 11, wherein the user input comprises a handheld input device configured as a ring or glove.

13. The device of claim 12, wherein the user input is communicated over a network.

14. The device of claim 1, further comprising a clitoral suction cup configured to fit over a clitoris.

15. A device for mimicking a portion of the male genitalia, the device comprising:
- a tubular body having:
  - a curved shaft,
  - a massager sub-assembly coupled to the shaft, the massager sub-assembly being movable relative to the shaft, and
  - a sheath covering the shaft and the massager sub-assembly; and
- a twisted-string drive having:
  - two or more strings coupled to the massager sub-assembly and configured to twist and untwist around themselves to change length and drive movement of the massager sub-assembly relative to the shaft,
  - a spring member at a first end of the two or more strings configured to maintain tension on the two or more strings, and
  - a motor at a second end of the two or more strings configured to twist and untwist the two or more strings.

* * * * *